(12) United States Patent
Song et al.

(10) Patent No.: US 12,419,708 B2
(45) Date of Patent: Sep. 23, 2025

(54) ROBOT ARM FOR SURGERY

(71) Applicant: LIVSMED INC., Seongnam-si (KR)

(72) Inventors: Young Jae Song, Seongnam-si (KR); Jung Joo Lee, Seongnam-si (KR); Hee Jin Kim, Seongnam-si (KR); Dong Kyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/961,003

(22) Filed: Nov. 26, 2024

(65) Prior Publication Data

US 2025/0082422 A1 Mar. 13, 2025

Related U.S. Application Data

(63) Continuation of application No. PCT/KR2023/007380, filed on May 30, 2023.

(51) Int. Cl.
| | |
|---|---|
| *A61B 34/30* | (2016.01) |
| *A61B 17/00* | (2006.01) |
| *A61B 34/00* | (2016.01) |
| *A61B 34/37* | (2016.01) |
| *B25J 9/04* | (2006.01) |
| *B25J 17/02* | (2006.01) |
| *B25J 18/04* | (2006.01) |

(52) U.S. Cl.
CPC .......... *A61B 34/30* (2016.02); *B25J 17/0283* (2013.01)

(58) Field of Classification Search
CPC ............................ A61B 34/30; B25J 17/0283
See application file for complete search history.

(56) References Cited

U.S. PATENT DOCUMENTS

| | | | |
|---|---|---|---|
| 2010/0069920 | A1 | 3/2010 | Naylor et al. |
| 2010/0240989 | A1 | 9/2010 | Stoianovici et al. |
| 2013/0325031 | A1* | 12/2013 | Schena .................. A61B 34/70 606/130 |

FOREIGN PATENT DOCUMENTS

| | | |
|---|---|---|
| EP | 2537483 B1 | 8/2018 |
| KR | 10-2012-0014758 A | 2/2012 |
| KR | 10-2013-0076825 A | 7/2013 |
| KR | 10-2186365 B1 | 12/2020 |
| WO | 2023/014149 A1 | 2/2023 |

* cited by examiner

*Primary Examiner* — Scott Luan
(74) *Attorney, Agent, or Firm* — Bridgeway IP Law Group, PLLC; Sang Ho Lee; Hyun Woo Shin

(57) ABSTRACT

A robot arm for minimally invasive surgery includes a modular structure in which a yaw axis of an active arm rotatable relative to a setup arm is disposed to be inclined with respect to a roll axis of an instrument for surgery and a joint of the active arm and a remote center of motion (RCM) form a parallelogram, thereby preventing a gimbal lock phenomenon, enabling configuration of various RCMs, and having various entry angles.

22 Claims, 92 Drawing Sheets

ROBOT ARM FOR SURGERY

CROSS-REFERENCE TO RELATED APPLICATION

This application is a continuation application of International Application No. PCT/KR2023/007380, filed on May 30, 2023, and claims priority to Korean Application No. 10-2022-0065669, filed on May 27, 2022, in the Korean Intellectual Property Office, the entire disclosures of which are incorporated herein by reference.

TECHNICAL FIELD

The present disclosure relates to a surgical robot arm, and more particularly, to a surgical robot arm for minimally invasive surgery, which is formed in a modular manner for use in a laparoscopic surgery or other various surgeries.

BACKGROUND ART

Medically, surgery refers to the treatment of diseases by cutting, slitting, or manipulating the skin, mucous membranes, or other tissues using medical devices. In particular, open surgery, which cuts and opens the skin of a surgical site and cures, shapes, or removes an organ therein, may cause bleeding, side effects, patient pain, scars, or the like. Accordingly, recently, surgery performed by inserting only a medical device, for example, laparoscopic surgical instrument, microsurgical microscope, and the like by forming a predetermined hole in the skin or surgery using a robot has been spotlighted as an alternative.

Here, a surgical robot refers to a robot that has a function of replacing a surgical action performed by a surgeon. Compared to humans, the surgical robot has the advantage of being able to operate with greater accuracy and precision, as well as being able to operate remotely.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery using a laparoscope and small surgical instruments.

Laparoscopic surgery is a cutting-edge surgery technique that involves perforating a small hole in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, can be obtained and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) equipped on the master robot, a surgical tool coupled to or held by a robot arm equipped on the slave robot may be manipulated to perform surgery.

The aforementioned background technology is technical information possessed by the inventor for derivation of the present disclosure or acquired by the inventor during the derivation of the present disclosure, and is not necessarily prior art disclosed to the public before the application of the present disclosure.

DESCRIPTION OF EMBODIMENTS

Technical Problem

The present disclosure is directed to providing a surgical robot arm capable of preventing a gimbal lock phenomenon, setting remote center of motion (RCM) in various ways, and allowing for various entry angles into the RCM, by forming a yaw axis of an active arm that is rotatable relative to a setup arm in an upper-to-lower direction and positioning the yaw axis to be inclined with respect to a roll axis of a surgical instrument.

Technical Solution to Problem

One aspect of the present disclosure provides a surgical robot arm to which a surgical instrument is mounted, the surgical robot arm including a setup arm including a body and a setup link assembly movably disposed on the body, and an active arm rotatably coupled to one end portion of the setup arm, wherein the active arm includes: a first link coupled to the setup arm by a first joint and formed to be yaw rotatable around a yaw axis with respect to the setup arm, a second link coupled to the first link centered at a second joint, a third link axially coupled to the second link to be rotatable around a third joint with respect to the second link, a fourth link axially coupled to the third link to be rotatable around a fourth joint with respect to the third link, and a fifth link that is axially coupled to the fourth link to be rotatable around a fifth joint with respect to the fourth link, and is formed to allow the surgical instrument to be mounted thereto, wherein a remote center of motion (RCM) is formed at the remaining vertex of a parallelogram with the third joint, the fourth joint, and the fifth joint constituting the other vertices, and the first joint is disposed relatively above the RCM.

In the present disclosure, the yaw axis and a roll axis of the surgical instrument may be configured to be different from each other.

In the present disclosure, in a state in which the roll axis of the surgical instrument is positioned parallel to a horizontal plane, the yaw axis and the roll axis may be configured to form a predetermined angle rather than being parallel to each other.

In the present disclosure, the setup link assembly may include one or more setup links configured to connect the active arm to the body and formed to be rotatable around a Z-axis with respect to the body.

In the present disclosure, the setup link assembly may include a first setup link linearly movable in a height direction on the body, a second setup link rotatably and axially coupled to the first setup link around a first shaft serving as a central axis of rotation, and a third setup link rotatably and axially coupled to the second setup link around a second shaft, which is different from the first shaft and serves as a central axis of rotation.

In the present disclosure, the yaw axis may be configured to be perpendicular to one surface of the third setup link, and the first link may be coupled to be rotatable around the yaw axis with respect to the third setup link.

In the present disclosure, the second shaft may be disposed perpendicular to the first shaft.

In the present disclosure, the setup link assembly may further include one or more setup links disposed between the second setup link and the third setup link, and formed to be rotatable around respective shafts that are substantially parallel to the first shaft.

In the present disclosure, a height, in a Z-axis direction, of a point at which the yaw axis passes through the setup arm may be designed to be higher than a height of the RCM in the Z-axis direction.

In the present disclosure, a height, in a Z-axis direction, of a proximal end of the yaw axis relative to the first joint may be designed to be higher than a height, in the Z-axis direction, of a distal end of the yaw axis relative to the first joint.

In the present disclosure, the setup arm may be formed to be operable only during a setup period in which the surgical robot arm is disposed on one side of a patient.

In the present disclosure, the RCM may be positioned on an extension line of the yaw axis.

In the present disclosure, when the third link rotates around the third joint, the fourth link and a line segment connecting the third joint to the RCM may rotate while maintaining a parallel state, and the third link and a line segment connecting the fifth joint to the RCM may rotate while maintaining a parallel state.

In the present disclosure, the RCM may remain constant in position regardless of the rotation of the third link.

In the present disclosure, the third link and a line segment connecting the fifth joint to the RCM may maintain a parallel state in any state of motion of the surgical robot arm, and the fourth link and a line segment connecting the third joint to the RCM may maintain a parallel state in any state of motion of the surgical robot arm.

In the present disclosure, each of the third link, the fourth link, and the fifth link may be formed to be offset by a certain degree in a direction of a rotational axis thereof.

In the present disclosure, the fourth link may be disposed on one side of the third link in a direction of a rotational axis of the third link.

In the present disclosure, the third link and the fourth link may be formed to allow at least partial overlap with each other in a direction of the yaw axis.

In the present disclosure, the fourth link and the fifth link may each be formed to allow at least partial overlap with each other in a direction of the yaw axis.

In the present disclosure, in a state in which the surgical instrument coupled to the fifth link is horizontal and an end tool of the surgical instrument is disposed in a direction away from the body, a first surface of the fifth link, to which the surgical instrument is coupled, may be disposed to face downward in a Z-axis direction.

In the present disclosure, in the state, the surgical instrument may be disposed below the fifth link.

In the present disclosure, in the state, the links may not be disposed between the surgical instrument and a bed.

In the present disclosure, a longitudinal central axis of the yaw axis and a longitudinal central axis of the fifth link may form a predetermined angle.

Another aspect of the present disclosure provides a surgical method using a surgical robot, the surgical method including disposing a body of a surgical robot arm having a modular configuration on one side of a port of a patient, through which a surgical instrument is to be inserted, adjusting a position of a setup arm including the body, disposing a fifth link, to which the surgical instrument is mounted, in a substantially horizontal state in an active arm connected to the setup arm, mounting the surgical instrument to the fifth link of the active arm, moving the surgical instrument mounted to the active arm to insert the surgical instrument into a body of the patient, and performing a surgery by the surgical instrument while maintaining a remote center of motion (RCM).

In the present disclosure, in the disposing of the body of the surgical robot arm on one side of the port of the patient, through which the surgical instrument is to be inserted, the body of the surgical robot arm may be disposed on the same side as the port of the patient relative to a bed.

In the present disclosure, in the disposing of the fifth link, to which the surgical instrument is mounted, in a substantially horizontal state in the active arm, at least some of a plurality of links of the active arm may be formed to overlap each other in an extension direction of each of the links.

In the present disclosure, in the mounting of the surgical instrument to the fifth link of the surgical robot arm, links of the surgical robot arm may not be disposed between the surgical instrument and the patient.

In the present disclosure, the active arm may include a first link coupled to the setup arm by a first joint and formed to be yaw rotatable around a yaw axis with respect to the setup arm, a second link axially coupled to the first link centered at a second joint, a third link axially coupled to the second link to be rotatable around a third joint with respect to the second link, a fourth link axially coupled to the third link to be rotatable around a fourth joint with respect to the third link, and a fifth link that is axially coupled to the fourth link to be rotatable around a fifth joint with respect to the fourth link, and is formed to allow the surgical instrument to be mounted thereto, wherein the RCM may be formed at the remaining vertex of a parallelogram with the third joint, the fourth joint, and the fifth joint constituting the other vertices, and the first joint may be disposed relatively above the RCM.

In the present disclosure, the yaw axis and a roll axis of the surgical instrument may be configured to be different from each other.

In the present disclosure, in a state in which the roll axis of the surgical instrument is positioned parallel to a horizontal plane, the yaw axis and the roll axis may be configured to form a predetermined angle rather than being parallel to each other.

In the present disclosure, the RCM may be positioned on an extension line of the yaw axis.

In the present disclosure, when the third link rotates around the third joint, the third link and a line segment connecting the fifth joint to the RCM may rotate while maintaining a parallel state, and the fourth link and an extension line connecting the third joint to the RCM may rotate while maintaining a parallel state.

In the present disclosure, a height, in a Z-axis direction, of a point at which the yaw axis passes through the setup arm may be designed to be higher than a height of the RCM in the Z-axis direction.

In the present disclosure, a height of a proximal end of the yaw axis in a Z-axis direction may be designed to be higher than a height of a distal end of the yaw axis in the Z-axis direction.

In the present disclosure, each of the third link and the fourth link may be formed to be offset by a certain degree in a direction of a rotational axis thereof.

In the present disclosure, in a state in which the surgical instrument coupled to the fifth link is horizontal and an end tool of the surgical instrument is disposed in a direction away from the body, a first surface of the fifth link, to which the surgical instrument is coupled, may be disposed to face downward in a Z-axis direction.

In the present disclosure, in the state, the surgical instrument may be disposed below the fifth link.

In the present disclosure, in the state, the links may not be disposed between the surgical instrument and a bed.

Other aspects, features, and advantages other than those described above will become apparent from the following views, claims, and detailed description of the disclosure.

Advantageous Effects

According to the present disclosure, by adjusting a position of a setup arm to which an active arm is coupled, a yaw axis can be maintained at a predetermined angle with respect to a horizontal plane, and the yaw axis can be inclined at a predetermined angle with respect to a roll axis of a surgical instrument, thereby preventing the occurrence of a gimbal lock phenomenon, and allowing a fifth link and the surgical instrument coupled thereto to be disposed in a horizontal direction. Furthermore, the surgical instrument can be disposed facing downward from above, beyond the horizontal direction.

In addition, by disposing each of the links to be offset by a certain degree, a rotational motion of each link is not constrained by another link, so that the range of motion of the instrument can be increased, such as a moving direction of the instrument is directed upward beyond the horizontal direction. Accordingly, even in surgeries in which the instrument is frequently disposed in the horizontal direction, an effect of preventing gimbal lock and allowing the instrument to move with a full range of motion can be obtained.

BEST MODE

Figure 1:
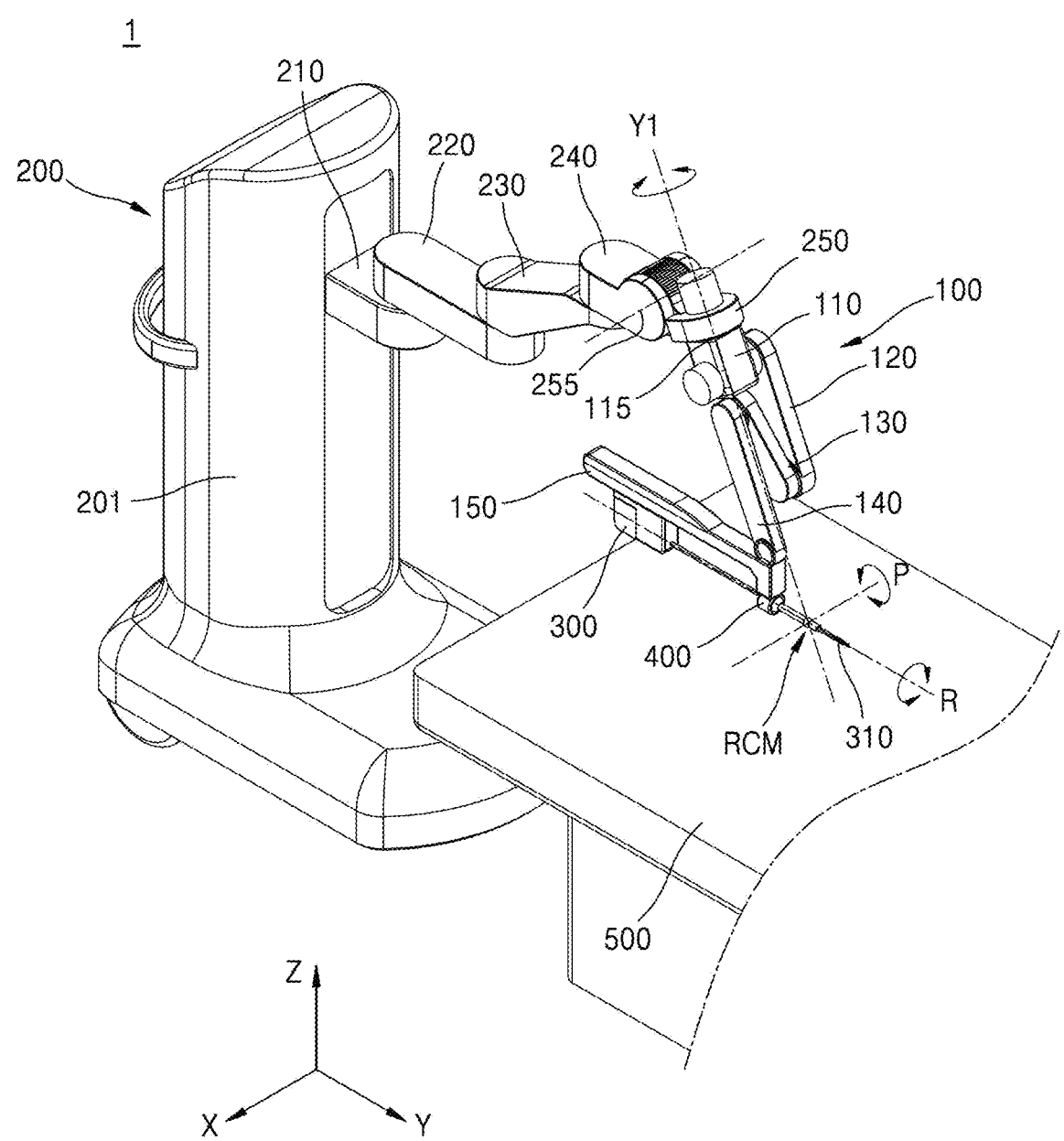
FIG. 1 is a perspective view illustrating a surgical robot arm according to a first embodiment of the present disclosure.

While the present disclosure is susceptible to various modifications and alternative forms, specific embodiments thereof are shown by way of example in the views and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, detailed description of known related arts will be omitted when it is determined that the gist of the present disclosure may be unnecessarily obscured.

Although terms such as "first," "second," and the like may be used to describe various components, such components should not be limited to the above terms. The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise", "comprising", "include", and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawing, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

Hereinafter, the embodiments of the present disclosure will be described with reference to the accompanying drawings.

Figure 91:
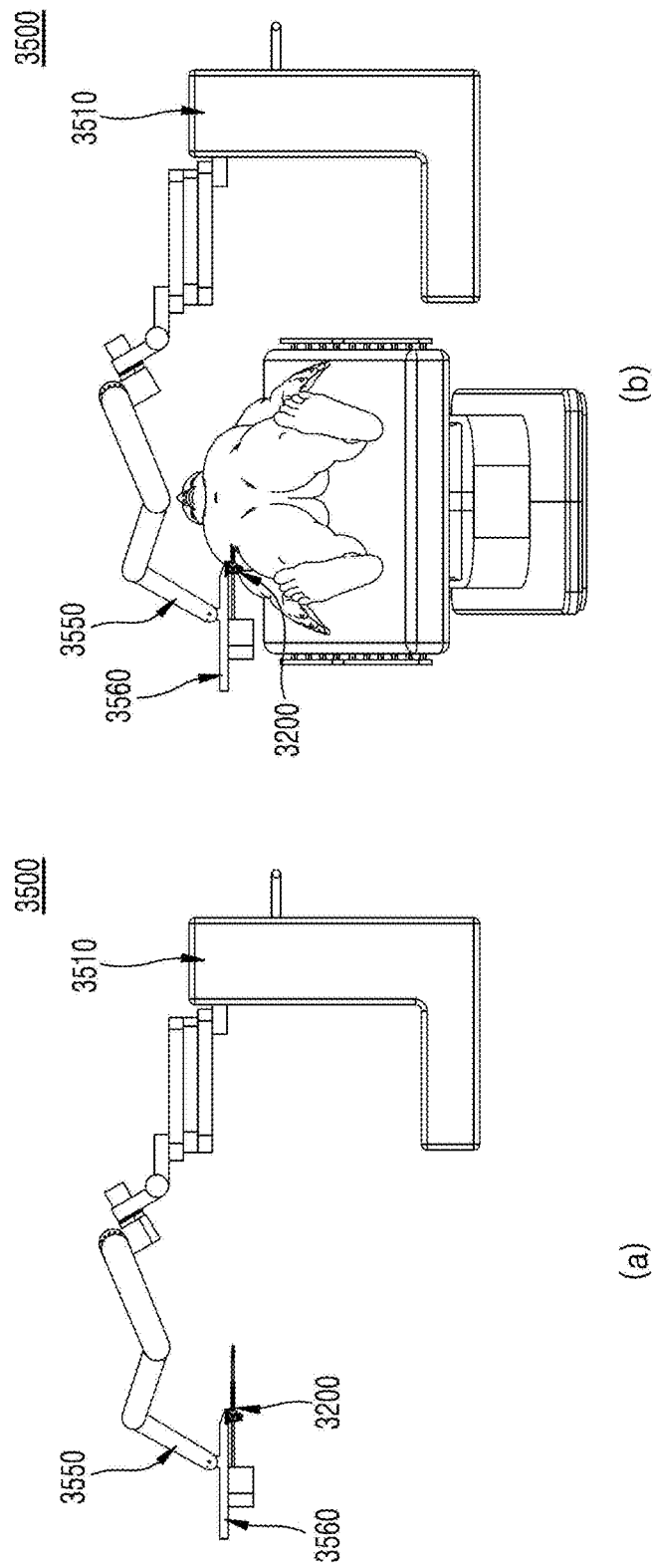
FIGS. 91 and 92 are views illustrating a surgical robot arm.

FIG. 91 is a view illustrating a surgical robot arm.

As shown in FIG. 91, a surgical robot arm 3500 typically operates in a manner in which one or a plurality of robot arms extend away from a single tower.

In such a structure, in the case of surgery that requires a surgical instrument 3200 to be inserted in a direction horizontal to the plane of an operating table on which a patient is lying, it was common that a tower 3510 is positioned across from a patient's surgical site, the surgical robot arm 3500 is deployed to extend away from the tower 3510 as if covering an upper portion of a patient's body, and the surgical instrument 3200 is disposed in a direction opposite to a direction, in which the surgical instrument 3200 extends, so as to face toward the patient again.

Thus, this may result in a disadvantage such as deploying multiple robot arms above the patient, along with other drawbacks like an increase in vibration and a reduction in rigidity occurring due to the way the surgical robot arm 3500 extends away from its support, i.e., the tower 3510.

Figure 92:
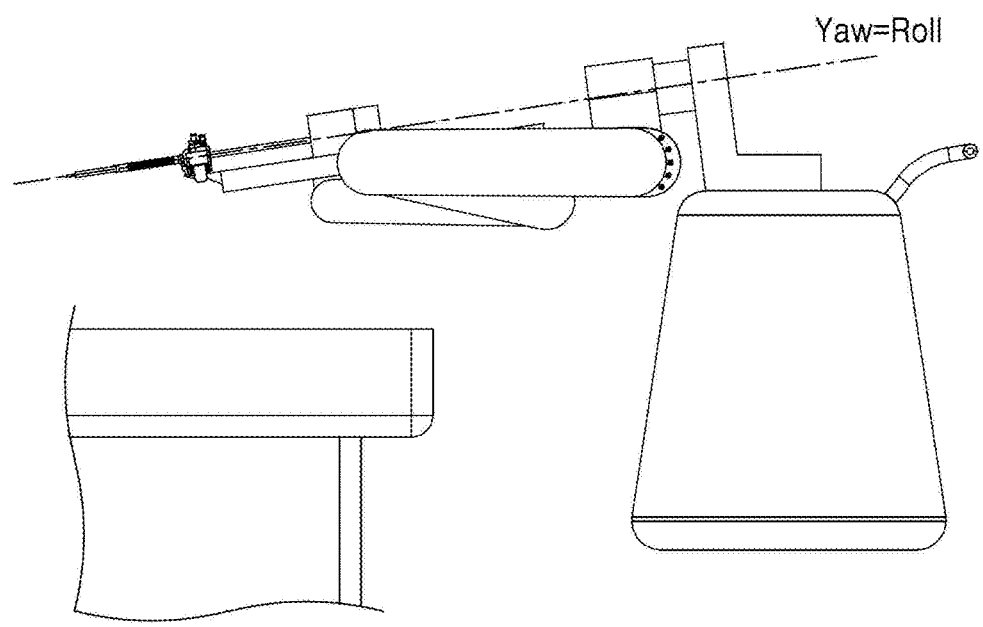

In order to address these issues, as shown in FIG. 92, the robot arm may be formed in a modular manner, allowing multiple robot arms to be disposed near a surgical site, with an instrument directly facing the patient.

However, when one rotational axis (a yaw axis) among multiple rotation axes around which the surgical instrument rotates coincides with an instrument's roll axis, which corresponds to an extension line of the surgical instrument, as shown in FIG. 92, a gimbal lock phenomenon may occur in which a motion (a yaw motion) of the surgical instrument expected when rotating around the one rotational axis (the yaw axis) becomes impossible.

In particular, the surgical instrument is often disposed horizontally during surgery, and when the yaw axis is also formed to be horizontal (or nearly horizontal), situations corresponding to the gimbal lock phenomenon may frequently occur.

In order to address such a problem, in the present disclosure, the yaw axis is positioned in a direction (e.g., a direction inclined with respect to the horizontal plane) other than a horizontal direction to prevent the gimbal lock phenomenon from occurring even when the surgical instrument is horizontally disposed, ensuring that gimbal lock does not occur even in the most commonly used positioning of the surgical instrument, thereby allowing a more compact configuration of the overall surgical robot.

Figure 61:
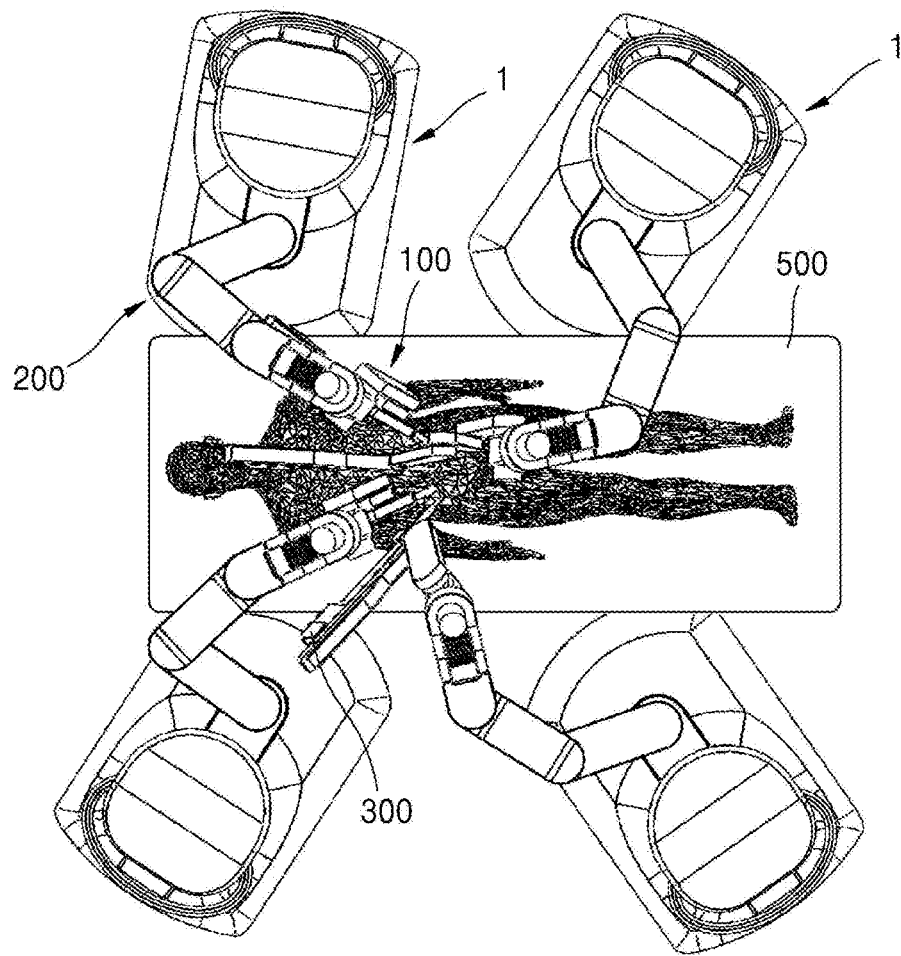
FIGS. 61 to 63 are views illustrating a state in which the surgical robot arm according to the first embodiment of the present disclosure is disposed near a patient's surgical site and the surgical instrument is disposed directly facing a patient.
Figure 62:
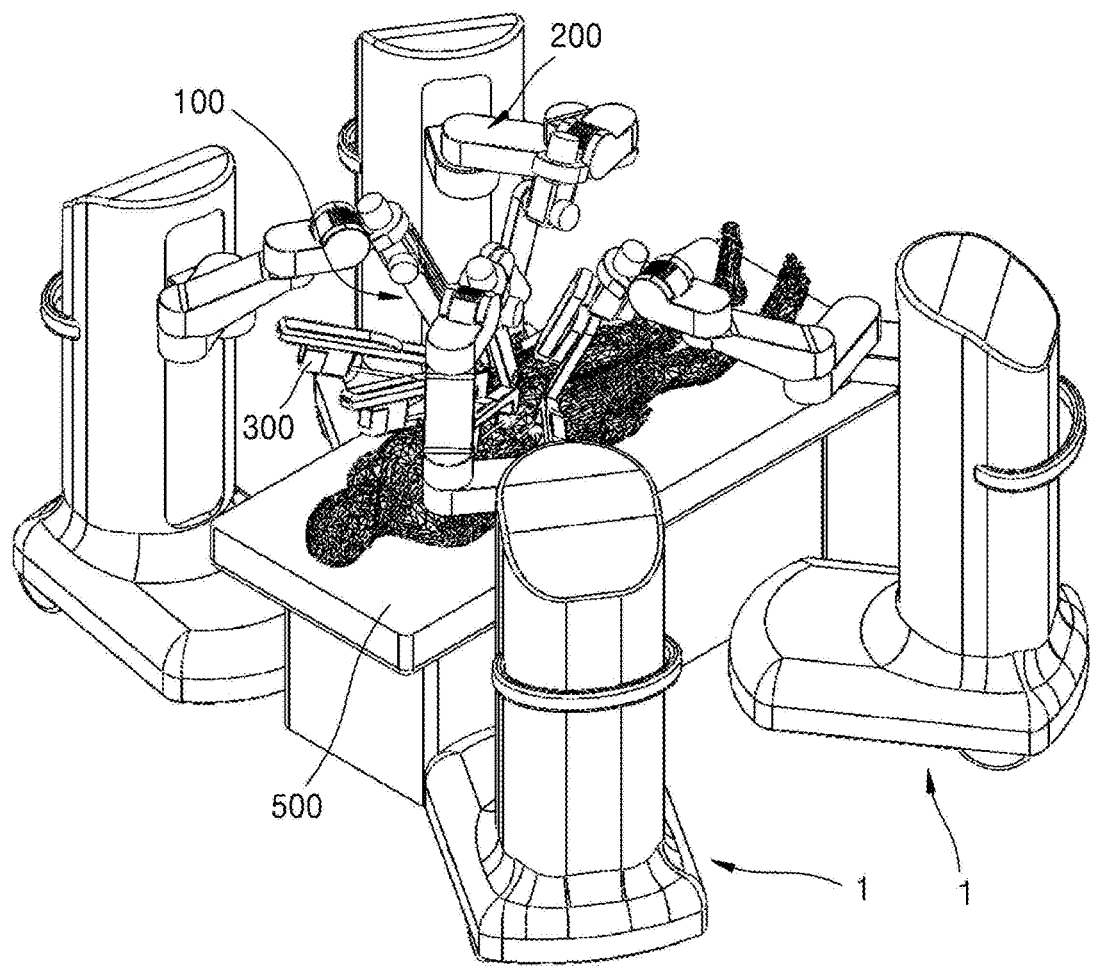
Figure 63:
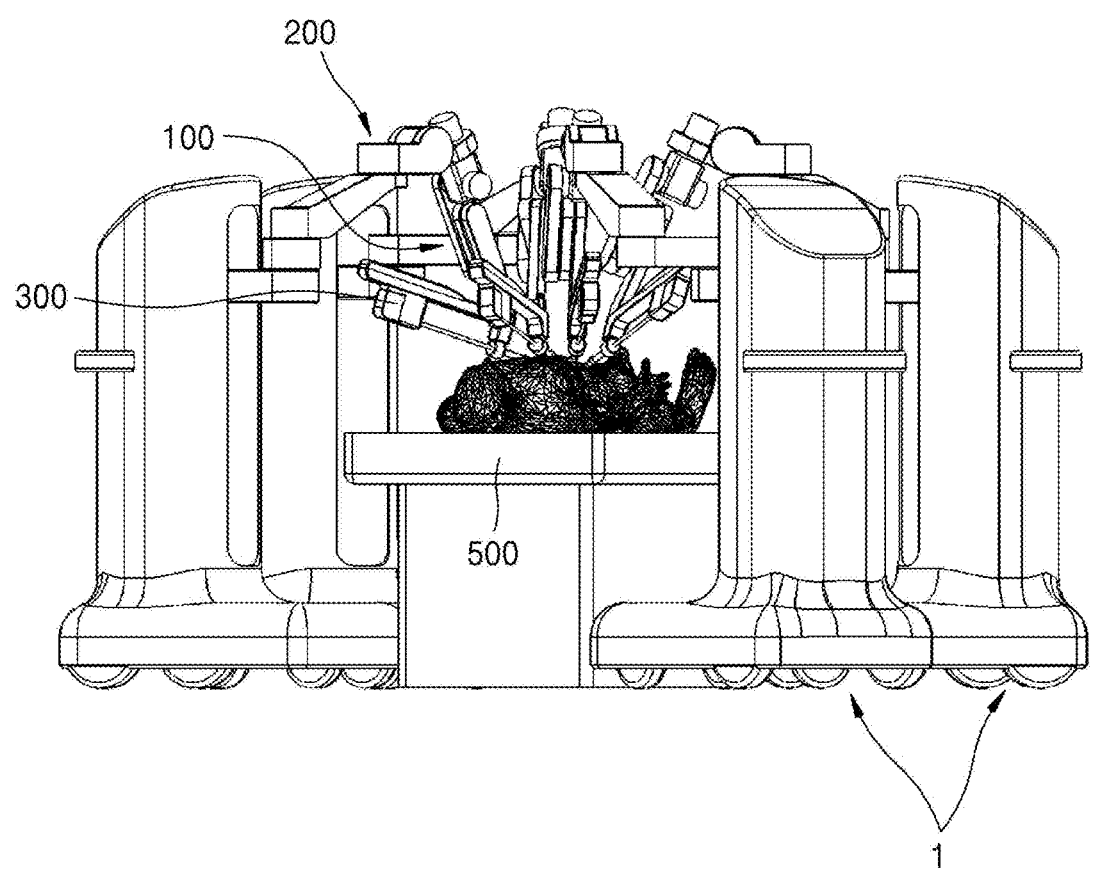

In addition, as illustrated in FIGS. 61 to 63, in the present disclosure, each surgical robot arm is formed in a modular manner, with one surgical instrument being deployed from one surgical robot arm. In addition, a plurality of surgical robot arms, each having a modular configuration and equipped with a single surgical instrument, are provided. In addition, these surgical robot arms are disposed in the vicinities of a plurality of ports of the patient, respectively, so that the overall length of the deployed surgical robot arms is shortened, thereby obtaining an effect of reducing vibration and increasing rigidity. In the present specification, the term "port" refers to a position through which a trocar is inserted and the surgical instrument passes.

A surgical robot arm according to the embodiments of the present disclosure, which is formed in a modular manner and in which one surgical instrument is deployed, will be described in detail later.

First Embodiment of Surgical Robot Arm

Hereinafter, a first embodiment of the present disclosure will be described with reference to the accompanying drawings.

Figure 2:
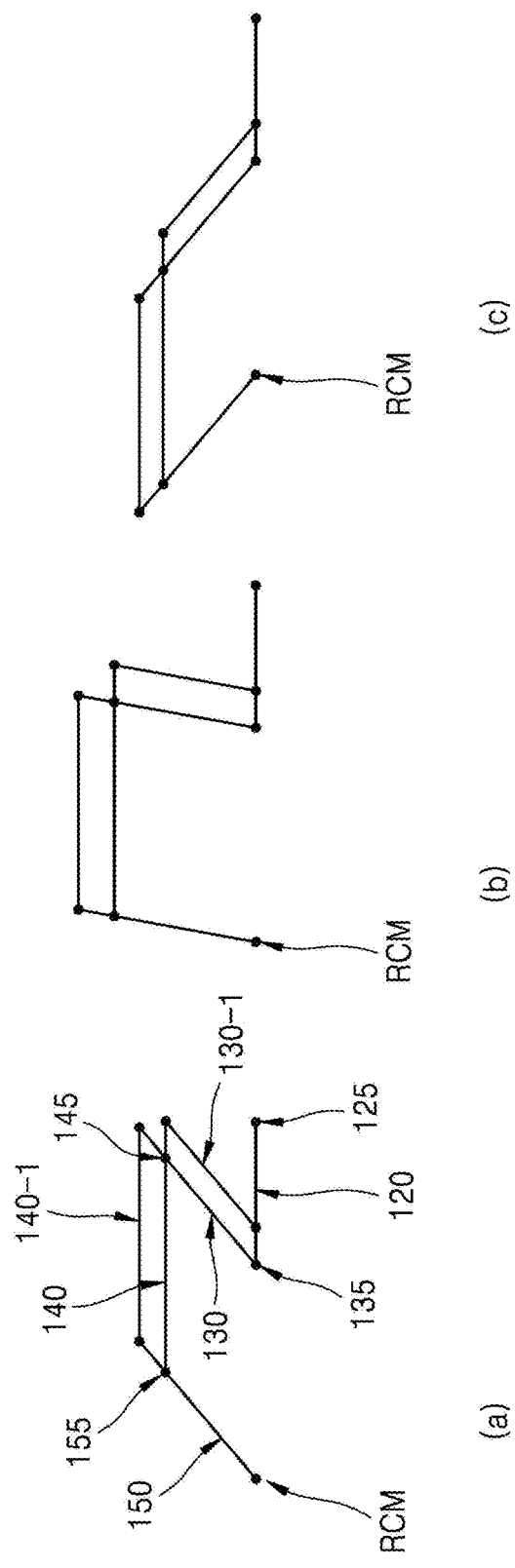
FIG. 2 is a diagram illustrating operational states of a remote center of motion (RCM) mechanism with a linkage structure.
Figure 3:
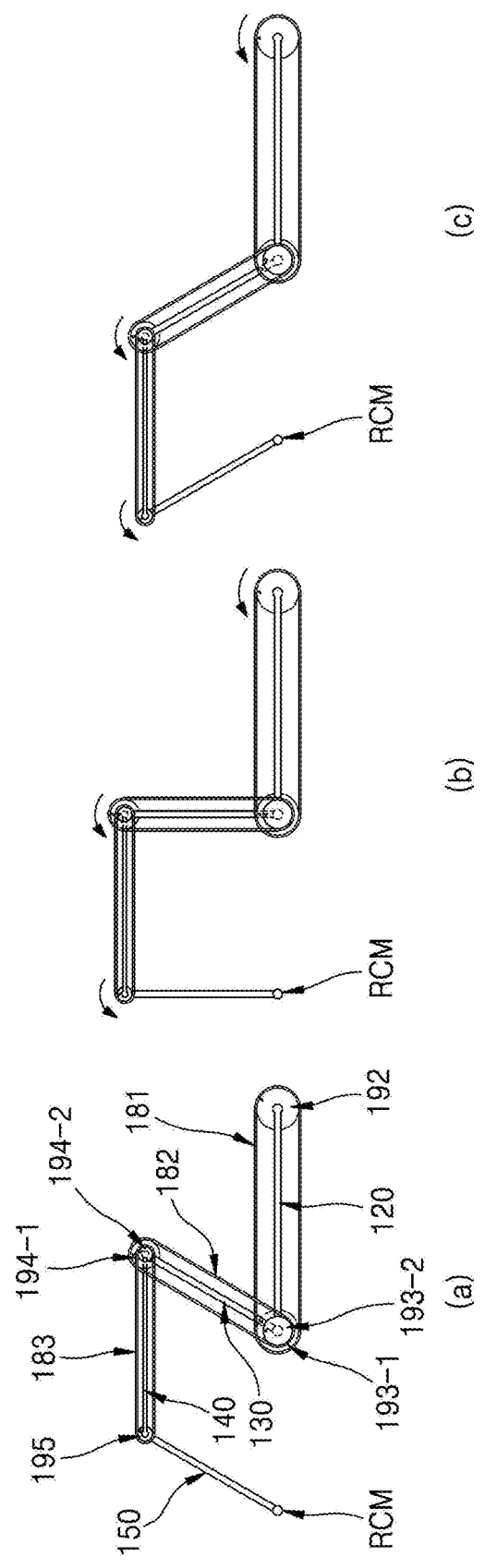
FIG. 3 is a diagram illustrating operational states of an RCM mechanism with a belt structure.
Figure 4:
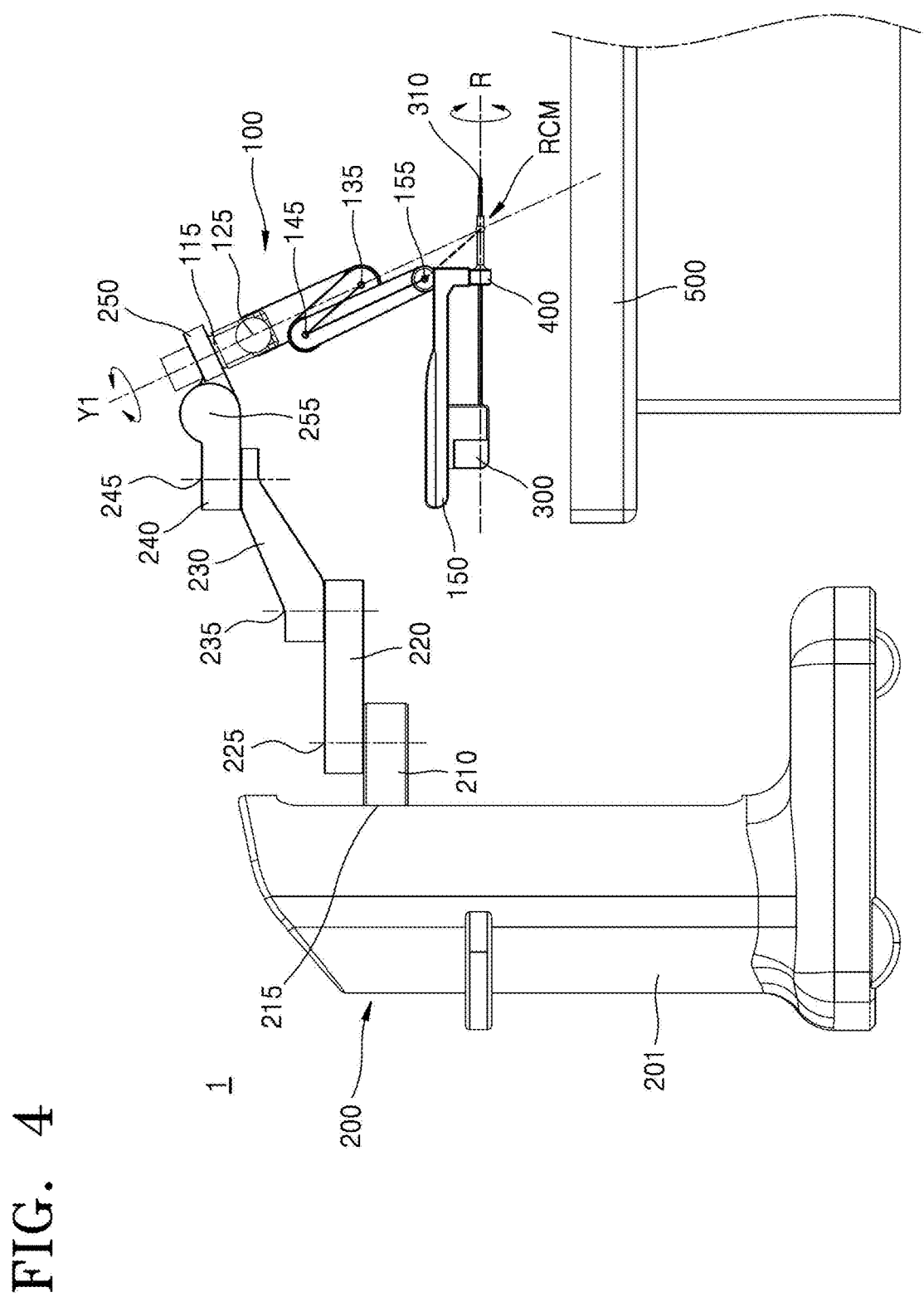
FIG. 4 is a side view illustrating the surgical robot arm of FIG. 1.
Figure 5:
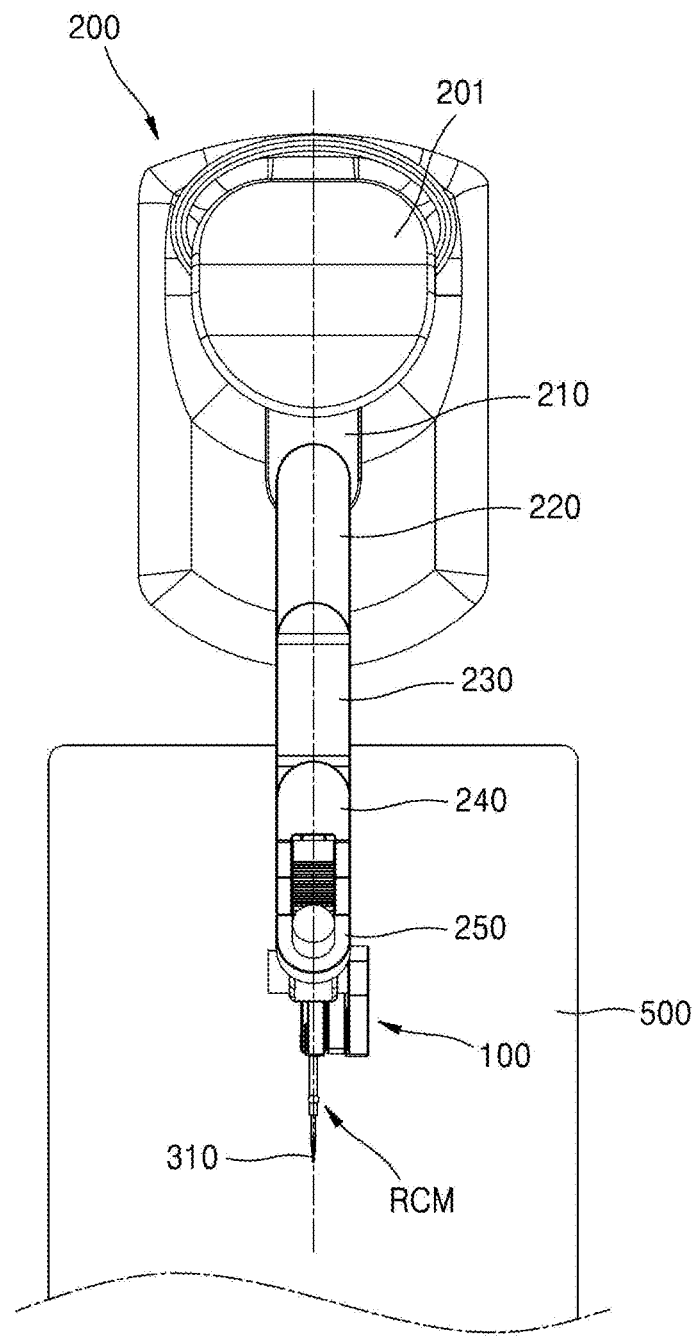
FIG. 5 is a plan view illustrating the surgical robot arm of FIG. 4.
Figure 6:
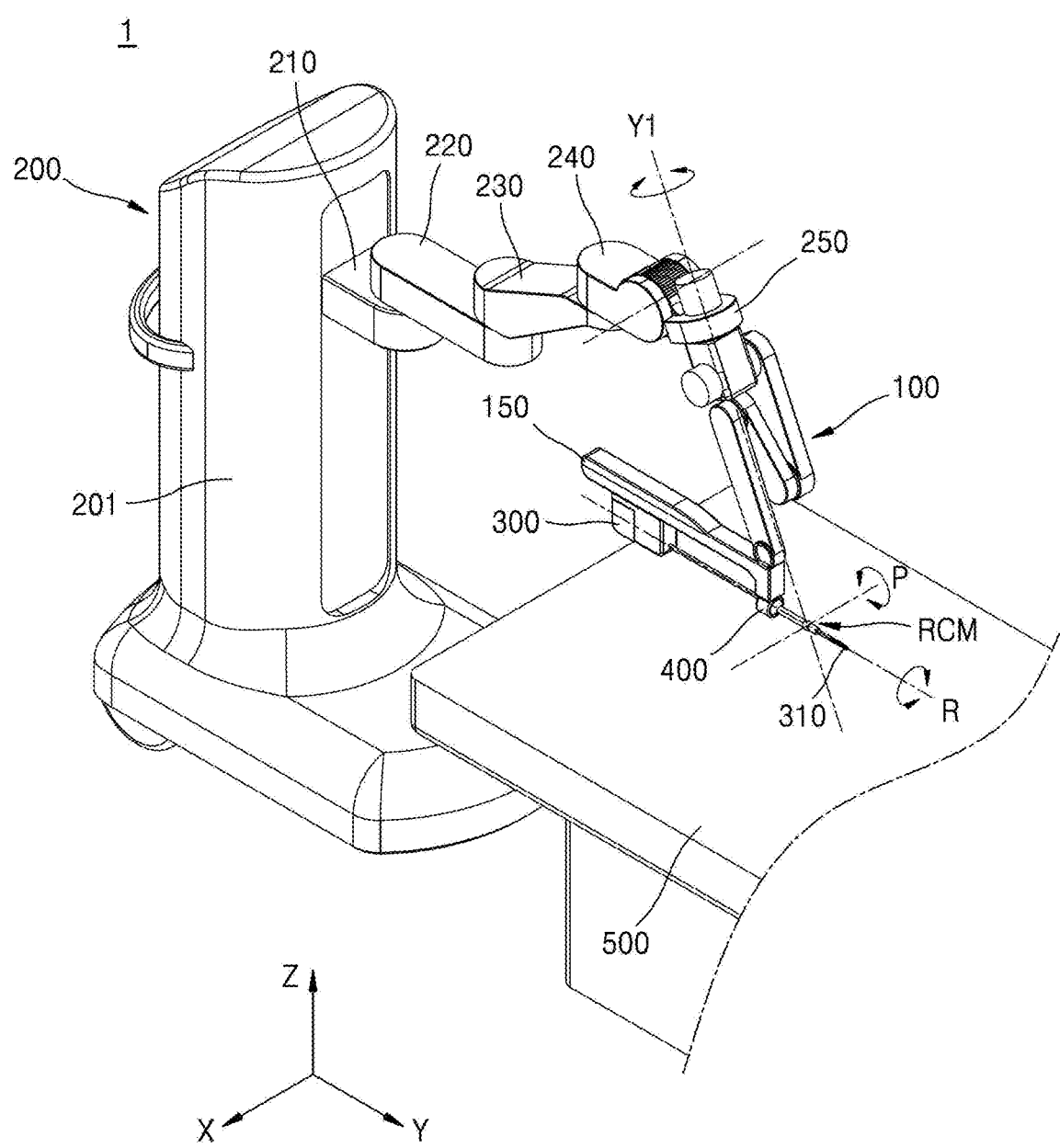
FIG. 6 is a perspective view illustrating an RCM motion (a first pitch motion) of the surgical robot arm of FIG. 4 around a pitch axis.
Figure 7:
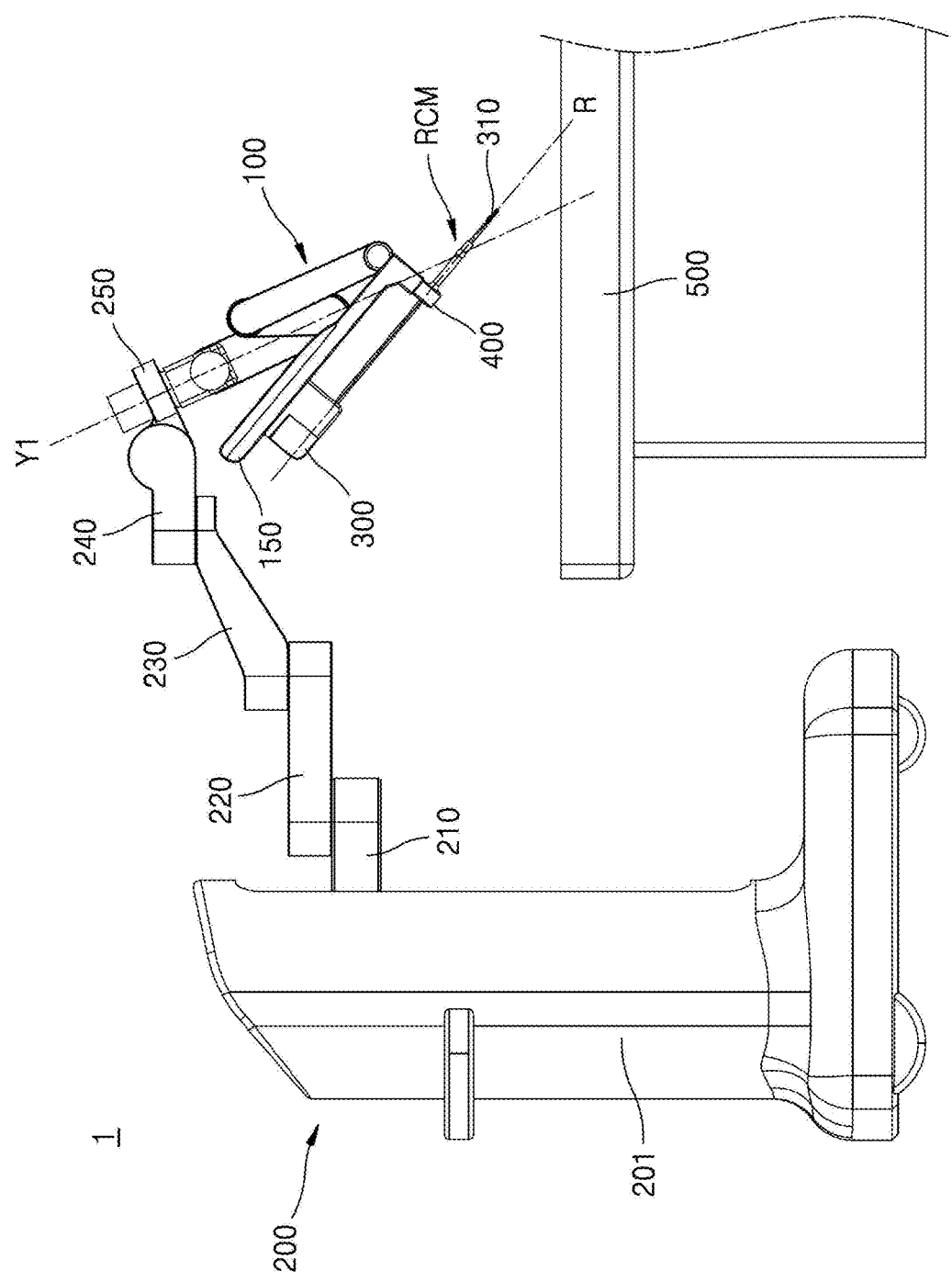
FIG. 7 is a side view illustrating an RCM motion (a second pitch motion) of the surgical robot arm of FIG. 4 around the pitch axis.
Figure 8:
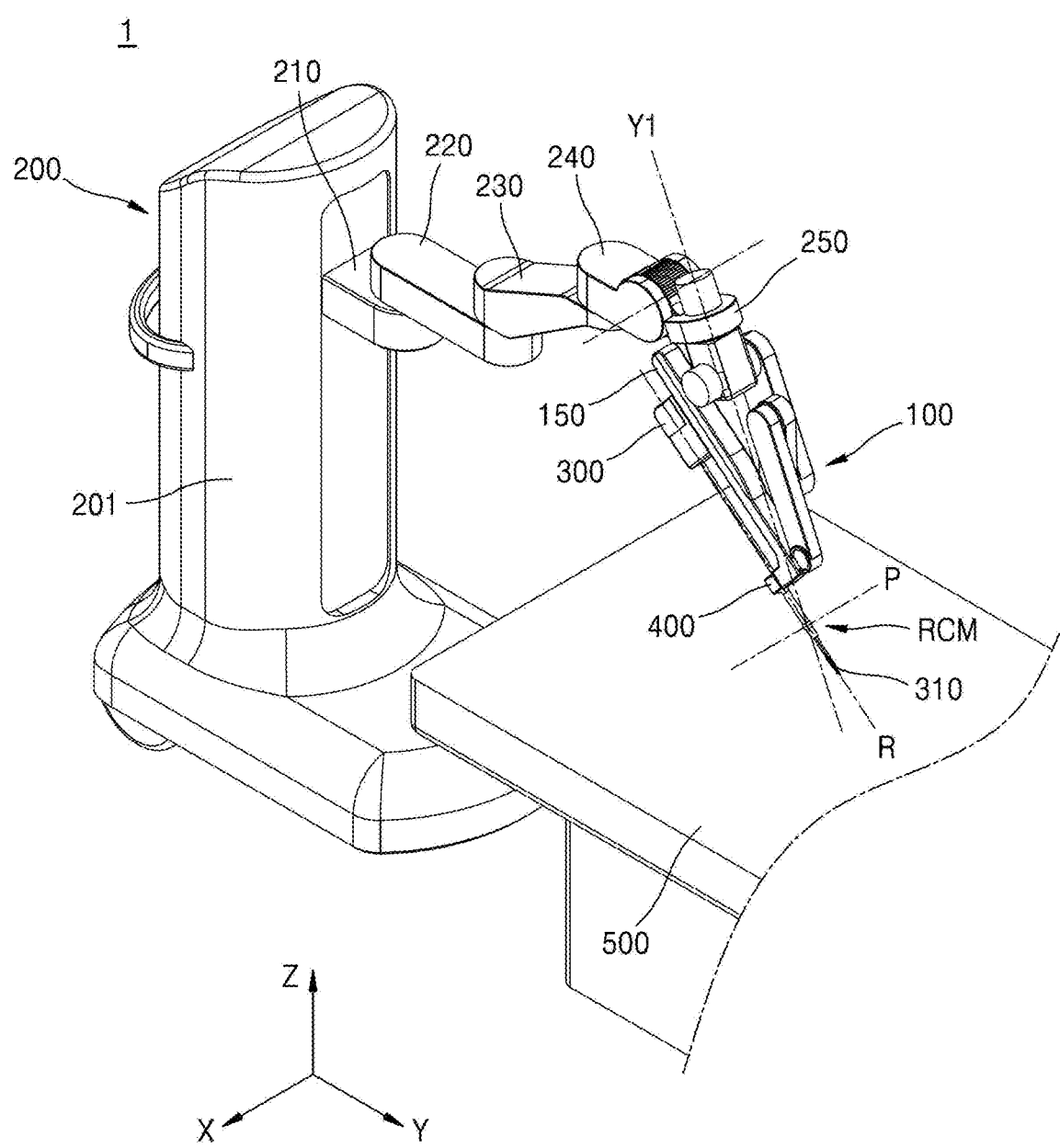
FIG. 8 is a perspective view illustrating the surgical robot arm of FIG. 7.
Figure 9:
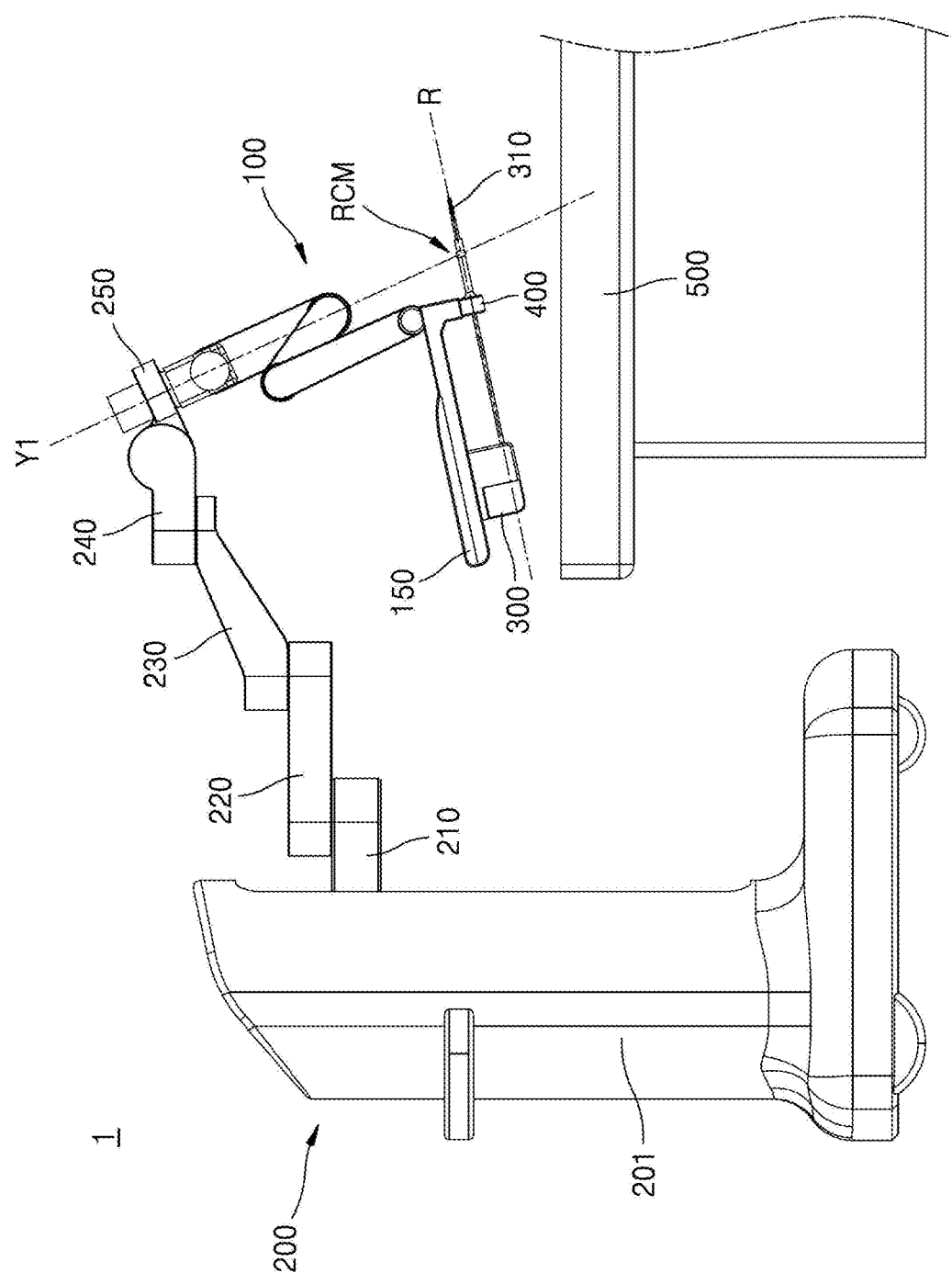
FIG. 9 is a side view illustrating an RCM motion (a third pitch motion) of the surgical robot arm of FIG. 4 around the pitch axis.
Figure 10:
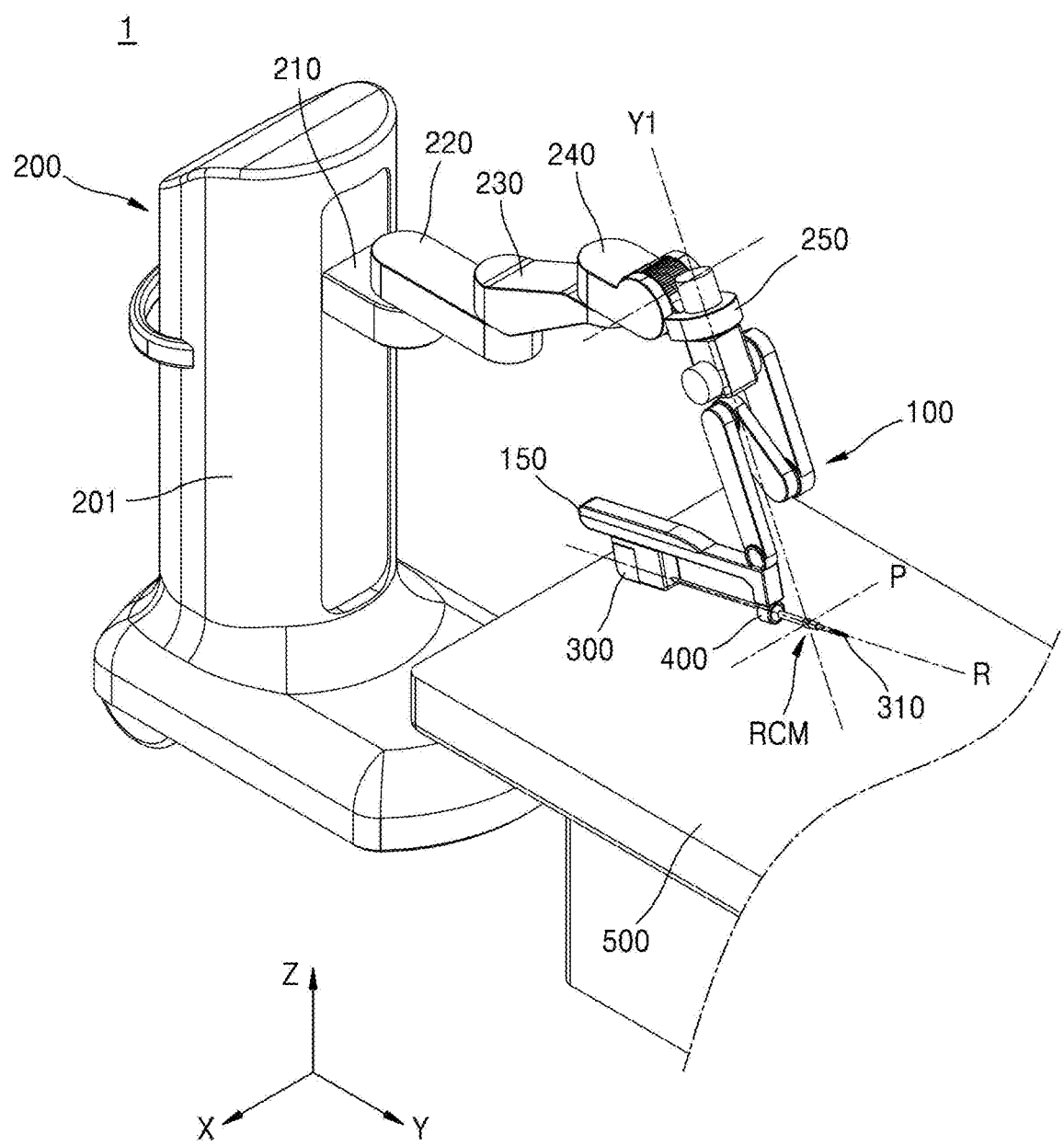
FIG. 10 is a perspective view illustrating the surgical robot arm of FIG. 9.
Figure 11:
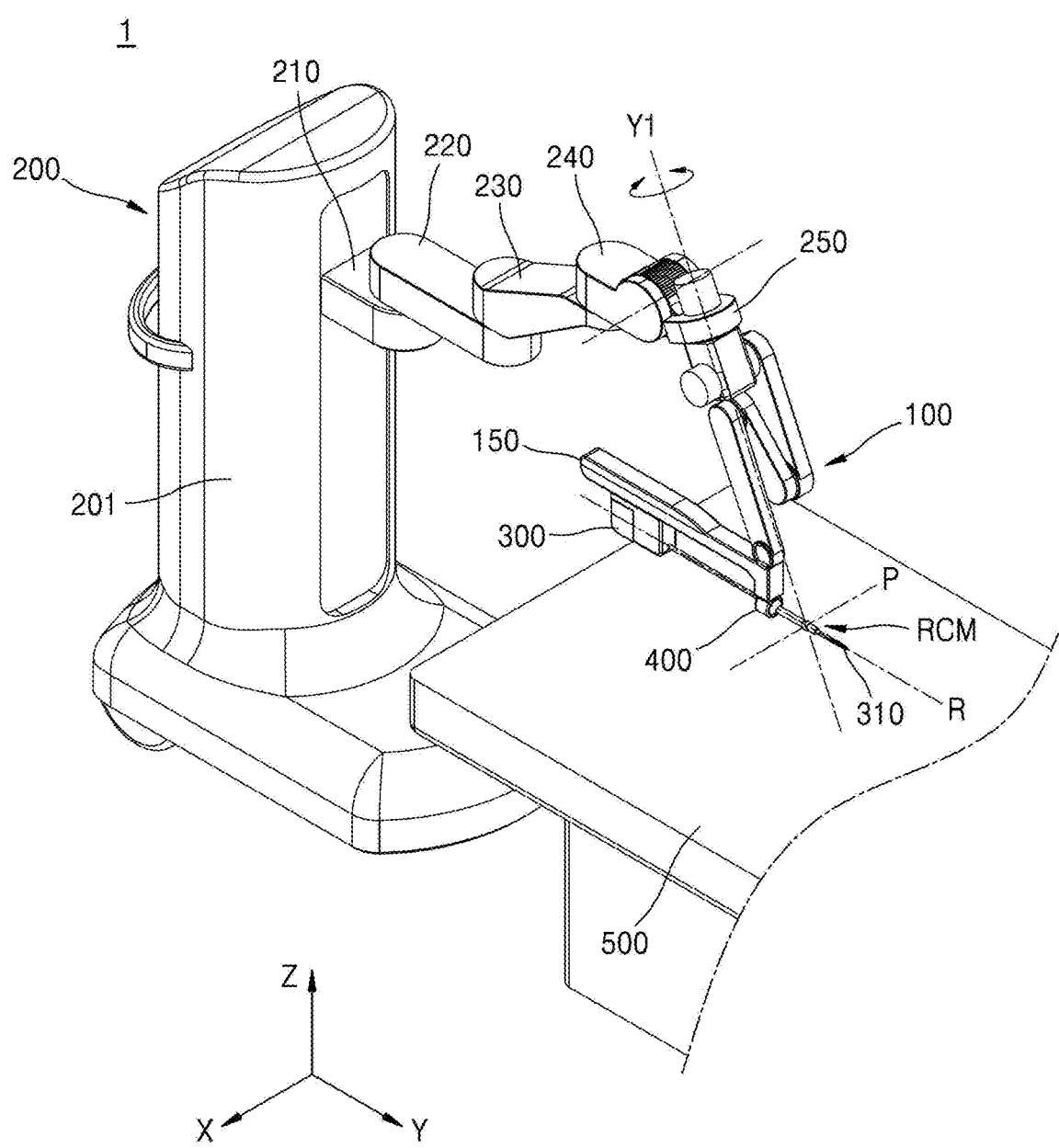
FIG. 11 is a perspective view illustrating an RCM motion (a first yaw motion) of the surgical robot arm according to the first embodiment of the present disclosure around a yaw axis.
Figure 12:
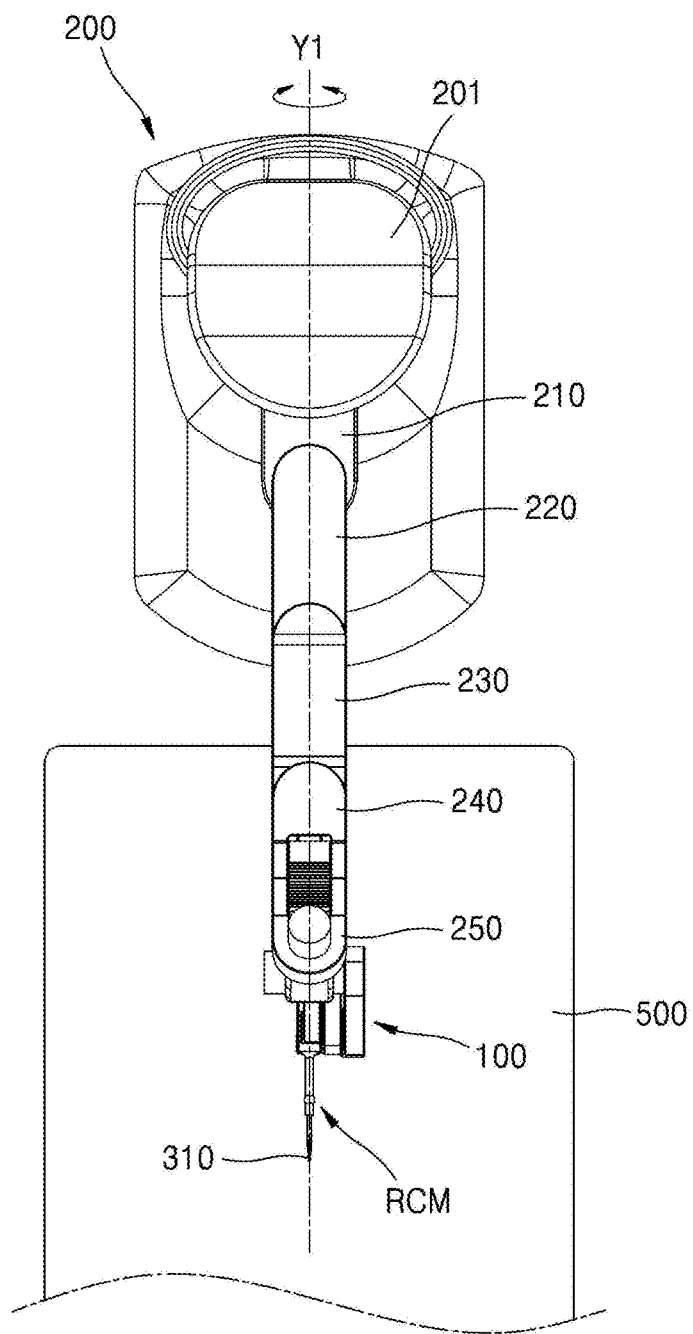
FIG. 12 is a plan view illustrating the surgical robot arm of FIG. 11.
Figure 13:
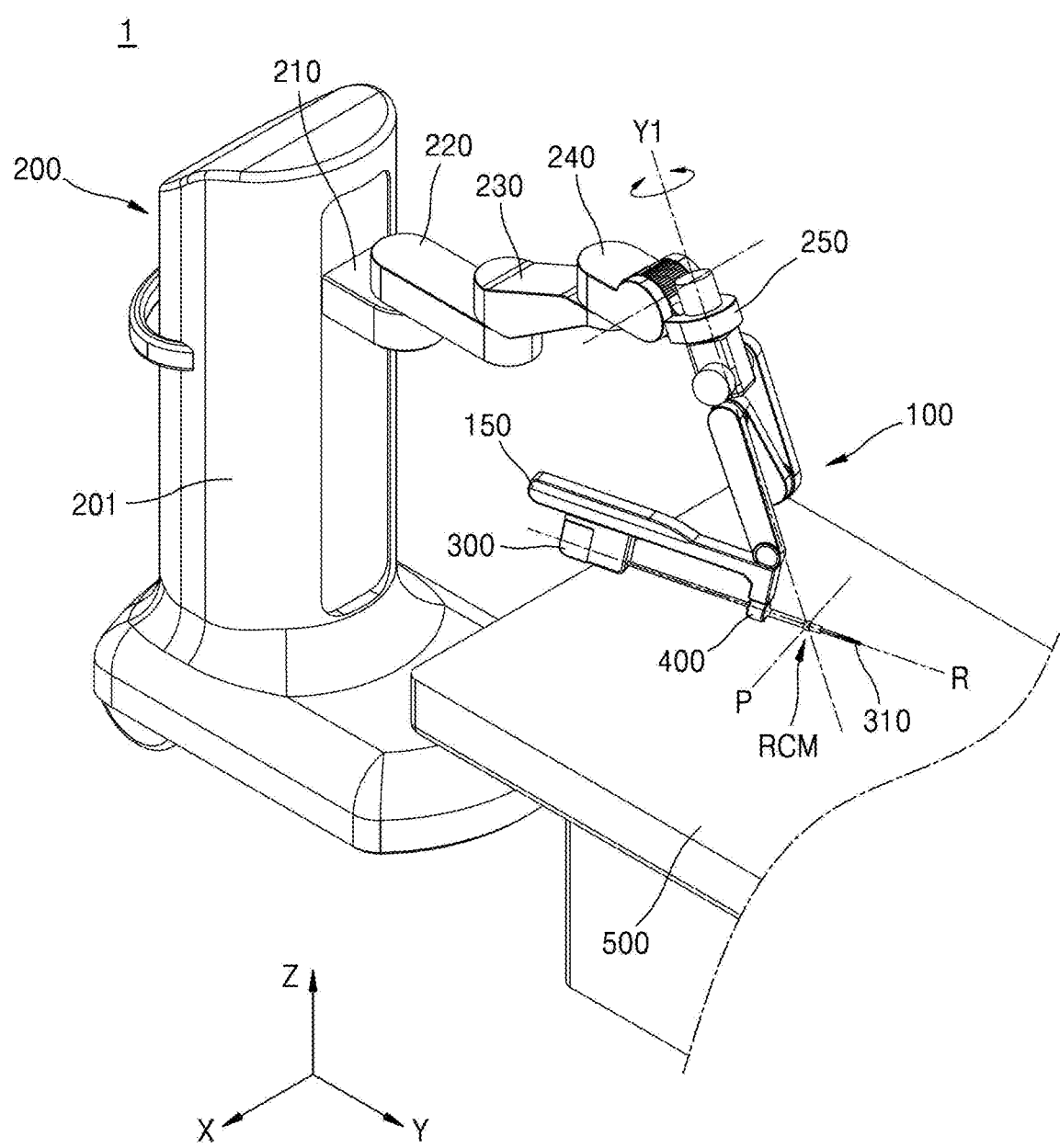
FIG. 13 is a perspective view illustrating an RCM motion (a second yaw motion) of the surgical robot arm according to the first embodiment of the present disclosure around the yaw axis.
Figure 14:
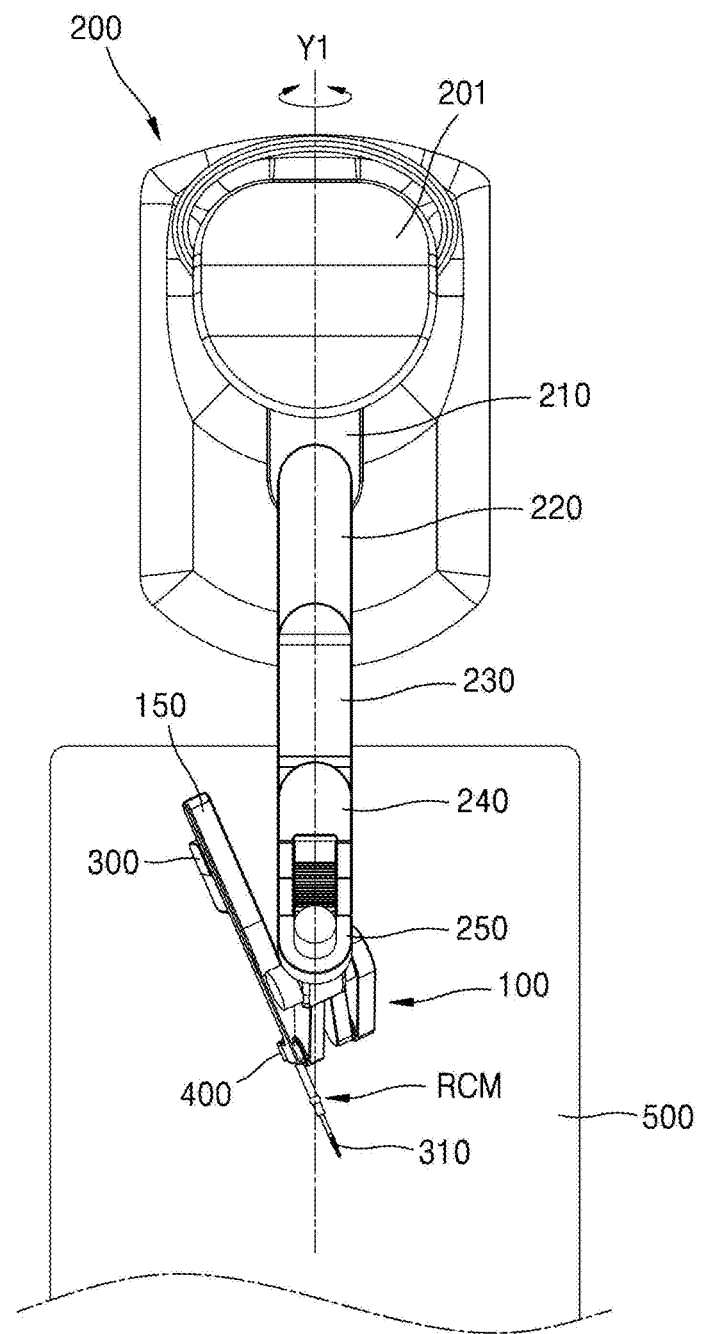
FIG. 14 is a plan view illustrating the surgical robot arm of FIG. 13.
Figure 15:
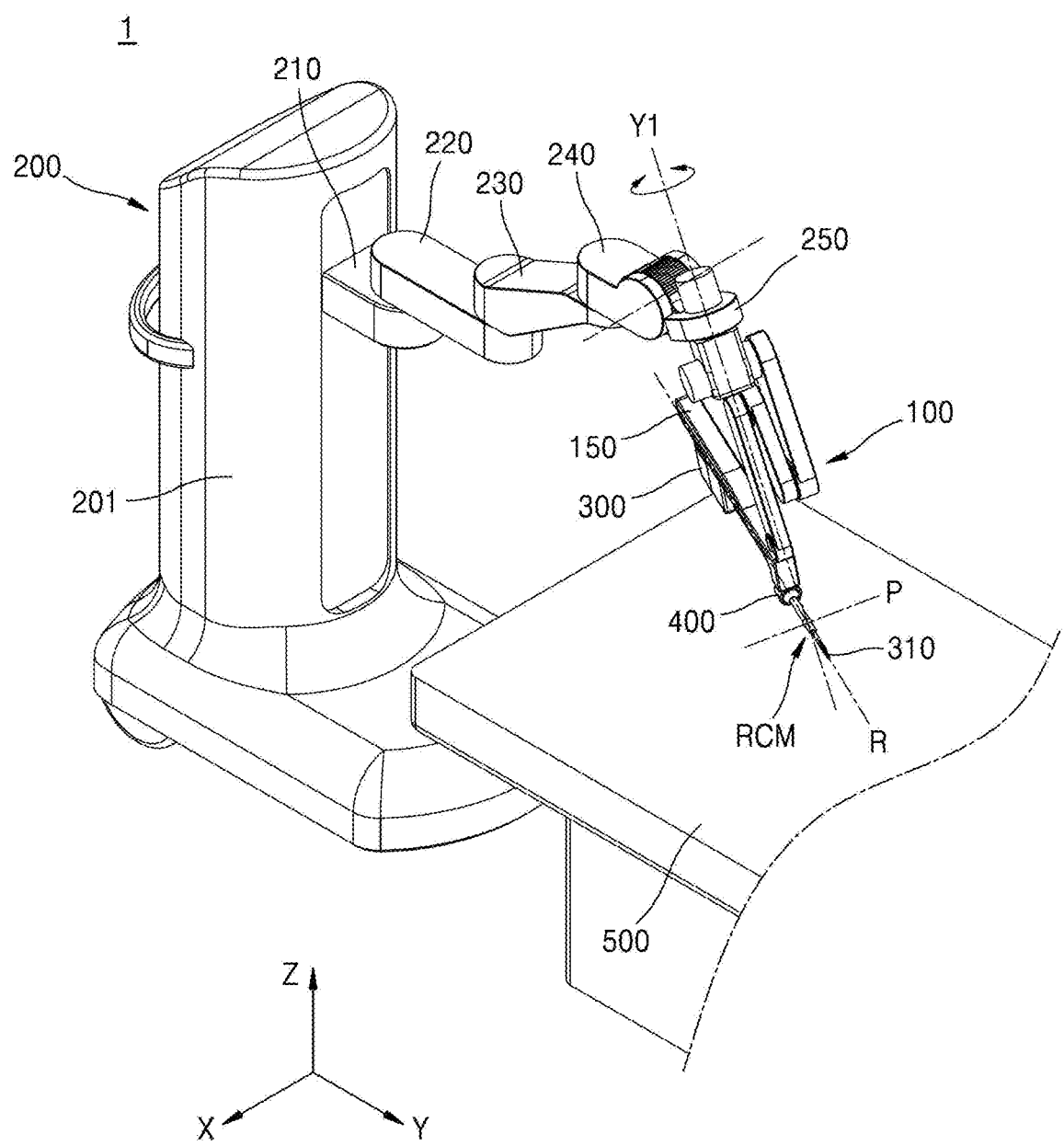
FIG. 15 is a perspective view illustrating an RCM motion (a third yaw motion) of the surgical robot arm according to the first embodiment of the present disclosure around the yaw axis.
Figure 16:
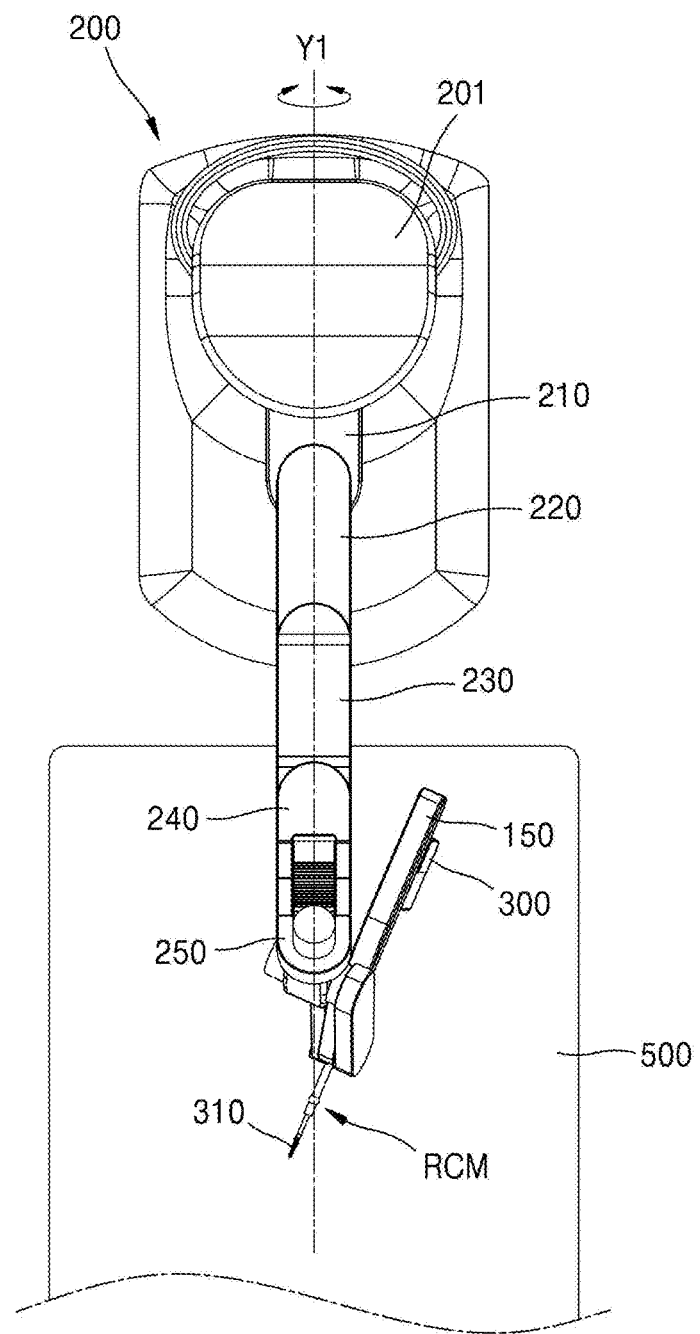
FIG. 16 is a plan view illustrating the surgical robot arm of FIG. 15.

FIG. 1 is a perspective view illustrating a surgical robot arm according to the first embodiment of the present disclosure. FIG. 2 is a diagram illustrating operational states of a remote center of motion (RCM) mechanism with a linkage structure. FIG. 3 is a diagram illustrating operational states of an RCM mechanism with a belt structure. FIG. 4 is a side view illustrating the surgical robot arm of FIG. 1. FIG. 5 is a plan view illustrating the surgical robot arm of FIG. 4. FIG. 6 is a perspective view illustrating an RCM motion (a first pitch motion) of the surgical robot arm of FIG. 4 around a pitch axis P. FIG. 7 is a side view illustrating an RCM motion (a second pitch motion) of the surgical robot arm of FIG. 4 around the pitch axis P. FIG. 8 is a perspective view illustrating the surgical robot arm of FIG. 7. FIG. 9 is a side view illustrating an RCM motion (a third pitch motion) of the surgical robot arm of FIG. 4 around the pitch axis P. FIG. 10 is a perspective view illustrating the surgical robot arm of FIG. 9. FIG. 11 is a perspective view illustrating an RCM motion (a first yaw motion) of the surgical robot arm according to the first embodiment of the present disclosure around a yaw axis Y1. FIG. 12 is a plan view illustrating the surgical robot arm of FIG. 11. FIG. 13 is a perspective view illustrating an RCM motion (a second yaw motion) of the surgical robot arm according to the first embodiment of the present disclosure around the yaw axis Y1. FIG. 14 is a plan view illustrating the surgical robot arm of FIG. 13. FIG. 15 is a perspective view illustrating an RCM motion (a third yaw motion) of the surgical robot arm according to the first embodiment of the present disclosure around the yaw axis Y1. FIG. 16 is a plan view illustrating the surgical robot arm of FIG. 15.

Referring to FIG. 1, a surgical robot arm 1 according to the first embodiment of the present disclosure may include an active arm 100 and a setup arm 200.

Here, the setup arm 200 is a part that is (manually) manipulated to position a surgical instrument 300 in place according to a patient's surgical site before surgery begins, and may be a part that remains stationary during an actual surgery. Meanwhile, the active arm 100 may be a part that moves in real time in response to a surgeon's manipulation during surgery.

The setup arm 200 according to an embodiment of the present disclosure may include a body 201 and a setup link assembly having a plurality of setup links 210, 220, 230, 240, and 250.

Specifically, the setup arm 200 may include a first setup link 210, a second setup link 220, a third setup link 230, a fourth setup link 240, and a fifth setup link 250. In addition, the setup arm 200 may include a first setup joint 215, a second setup joint 225, a third setup joint 235, a fourth setup joint 245, and a fifth setup joint 255.

The active arm 100 according to an embodiment of the present disclosure, to which the surgical instrument 300 is mounted, may be connected to the setup arm 200 and may include a first link 110, a second link 120, a third link 130, a fourth link 140, and a fifth link 150. In addition, the active arm 100 may include a first joint 115, a second joint 125, a third joint 135, a fourth joint 145, and a fifth joint 155. In addition, a trocar 400 and the surgical instrument 300 are coupled to the fifth link 150 of the surgical robot arm 1.

Referring to FIG. 1, the first link 110 is connected to the fifth setup link 250 and specifically rotates around the first joint 115 serving as a rotation center, and a central axis of rotation thereof may be configured as the yaw axis Y1 of the surgical robot arm 1.

Referring to FIG. 1, the fifth setup link 250 in the setup arm 200 of the surgical robot arm 1 according to the first embodiment of the present disclosure rotates around the fifth setup joint 255 serving as a rotation center, and a central axis of rotation thereof may be configured parallel to the pitch axis P of the active arm 100. However, when the active arm 100 rotates around the yaw axis Y1 by a certain degree, the central axis of rotation of the fifth setup link 250 and the pitch axis P may no longer be parallel to each other.

Referring to FIG. 1, the first link 110 in the active arm 100 of the surgical robot arm 1 according to the first embodiment of the present disclosure is rotatable around the first joint 115 with respect to the fifth setup link 250. That is, the first link 110 is rotatable around the yaw axis Y1, which passes through the rotation center of the first joint 115, with respect to the fifth setup link 250.

Here, the third link 130, the fourth link 140, and the fifth link 150 may form a parallelogram, and configure a kind of RCM mechanism.

In detail, a surgical robot (not shown) may include one or more surgical robot arms for surgical manipulation, and a surgical instrument is mounted on a front-end portion of the surgical robot arm.

In general, a robot arm refers to a device having a function similar to that of the arm and/or the wrist of a human being and having a wrist portion to which a predetermined tool may be attached. In the present specification, the robot arm may be defined as a concept that encompasses all of components, such as an upper arm, a lower arm, a wrist, and an elbow, and a surgical instrument coupled to the wrist portion. The above-described surgical robot arm may be implemented to have multiple° of freedom.

When a surgery is performed by mounting the surgical instrument to the front end of the surgical robot arm as described above, the movement of the surgical instrument along with the movement of the surgical robot arm may cause unnecessary damage to the patient's skin in the process of performing the surgery by making a small puncture in a patient's skin and inserting a surgical instrument into the puncture. In addition, when a surgical site is large, there is a concern that the advantages of robotic surgery may be halved due to the need to cut the skin by as much as a moving path of the surgical instrument or the need to puncture the skin at each surgical site.

Accordingly, a virtual rotation center point is set at a certain position (mainly a pivot point through which the trocar penetrates the patient's skin) with respect to the surgical instrument mounted at the front end of the surgical robot arm, and the robot arm is controlled so that the surgical instrument rotates around the certain position, which is referred to as a "remote center" or "remote center of motion" (RCM). The RCM mechanism of the present disclosure will be described in more detail later.

Hereinafter, each component of the surgical robot arm 1 according to the first embodiment of the present disclosure will be described in more detail.

Motions of Setup Arm of Surgical Robot Arm

Referring to FIGS. 1, 4, and 5, the surgical robot arm 1 according to the first embodiment of the present disclosure may include the active arm 100 and the setup arm 200. The setup arm 200 is positioned on an outer side of a bed 500 on which a patient is placed, and may be connected to the active arm 100.

Referring to FIG. 1, in the present embodiment, for convenience, a width direction of the bed 500 on which the patient lies is defined as an X-axis, a length direction of the bed is defined as a Y-axis, and a direction perpendicular to the ground is defined as a Z-axis.

The setup arm 200 functions to set the position and posture of the active arm 100 so that the surgical instrument 300 coupled to the active arm 100 can be disposed appropriately for surgery, and operates only in a pre-surgery stage to set the position, and once the surgery begins, the setup arm 200 remains stationary and is fixed in position.

That is, the setup arm 200 may be formed to be operable only during a setup period during which the surgical robot arm is disposed on one side of the patient.

The position of the setup arm 200 may be changed by being manually manipulated by a user, such as medical staff.

In an optional embodiment, the setup arm 200 may include a driving part (not shown), and various modifications are possible, such as allowing the user to change the position of the setup arm 200 externally with a device (not shown) such as a controller.

Referring to FIG. 1, the active arm 100 may be rotatably and movably connected to one side of the setup arm 200. The active arm 100 will be described in detail later.

Referring to FIGS. 1 and 4, the setup arm 200 according to the first embodiment of the present disclosure may include the body 201, the setup link assembly having a plurality of setup links, and a plurality of setup joints 215, 225, 235, 245, and 255.

The plurality of setup joints 215, 225, 235, 245, and 255 may connect the body 201 to one of the plurality of setup links or connect the plurality of setup links to each other, and form a reference point for rotation and movement.

Referring to FIGS. 1 and 4, the body 201 may serve as a base of the entire surgical robot arm 1. A moving device (no reference number is assigned) such as a wheel is formed on a lower surface of the body 201, and thus the body 201 may also serve as a kind of moving member.

In an optional embodiment, a position fixing device (not shown) may be further formed on the body 201 to fix the position of the surgical robot arm 1 including the body 201 during surgery.

However, the concept of the present disclosure is not limited thereto, and various modifications may be possible, such as forming the body 201 in a shape that can be detachably attached to the bed 500 or to a wall surface.

The setup link assembly may include the first setup link 210, the second setup link 220, the third setup link 230, the fourth setup link 240, and the fifth setup link 250. In addition, the setup arm 200 may include the first setup joint 215, the second setup joint 225, the third setup joint 235, the fourth setup joint 245, and the fifth setup joint 255.

The first setup joint 215 may be formed to allow vertical movement (the movement in a Z-axis direction based on FIG. 1) with respect to the body 201.

Figure 20:
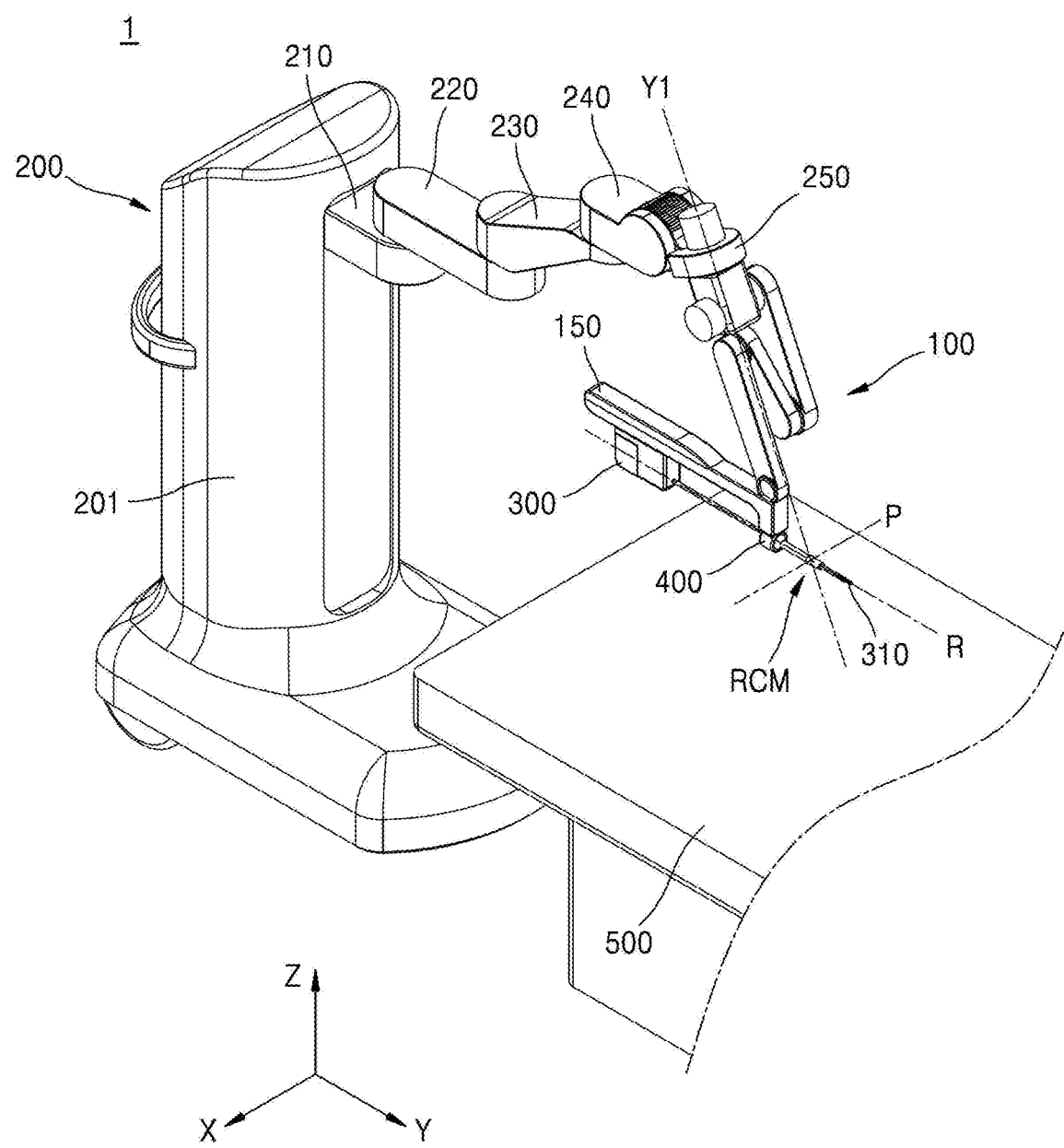
FIG. 20 is a perspective view illustrating a state in which a setup arm of the surgical robot arm according to the first embodiment of the present disclosure is raised on the body.

Specifically, referring to FIGS. 20 to 23, the first setup link 210 on the body 201 is reciprocatingly movable in a preset direction (in a vertical direction based on FIG. 20). This will be described in more detail later.

In addition, the first setup joint 215 may rotate around a central axis of rotation, which is configured parallel to the Y-axis (based on FIG. 1), with respect to the body 201.

Referring to FIGS. 1 and 4, the second setup link 220 may be coupled to the first setup link 210 so as to be rotatable around the second setup joint 225, which serves as a rotation center, with respect to the first setup link 210. Here, the second setup joint 225 may include one or more pulleys. Here, the second setup link 220 may rotate around an axis parallel to the Z-axis with respect to the first setup link 210.

The third setup link 230 may be coupled to the second setup link 220 so as to be rotatable around the third setup joint 235 with respect to the second setup link 220. Here, the third setup joint 235 may include one or more pulleys. Here, the third setup link 230 may rotate around an axis parallel to the Z-axis with respect to the second setup link 220.

The fourth setup link 240 may be coupled to the third setup link 230 so as to be rotatable around the fourth setup joint 245 with respect to the third setup link 230. Here, the fourth setup joint 245 may include one or more pulleys. Here, the fourth setup link 240 may rotate around an axis parallel to the Z-axis with respect to the third setup link 230.

The fifth setup link 250 may be coupled to the fourth setup link 240 so as to be rotatable around the fifth setup joint 255 with respect to the fourth setup link 240. Here, the fifth setup joint 255 may include one or more pulleys. Here, the fifth setup link 250 may rotate around an axis parallel to the X-axis with respect to the fourth setup link 240.

That is, the central axis of rotation of the fifth setup link 250 with respect to the fourth setup link 240 may be configured differently from a central axis of rotation of the second setup link 220 with respect to the first setup link 210. Specifically, the central axis of rotation of the fifth setup link 250 with respect to the fourth setup link 240 may be positioned perpendicular to the central axis of rotation of the second setup link 220 with respect to the first setup link 210.

A central axis of rotation of the third setup link 230 with respect to the second setup link 220 and a central axis of rotation of the fourth setup link 240 with respect to the third setup link 230 may be configured parallel to the central axis of rotation of the second setup link 220 with respect to the first setup link 210.

FIG. 1 and FIGS. 4 to 41 are views illustrating a state in which the fifth setup link 250 is rotated by 20° with respect to the fourth setup link 240. In other words, an angle formed by the horizontal plane and the fifth setup link 250 is 20°.

Referring to FIGS. 1 and 4, the above-described first link 110 of the active arm 100 may be coupled to the setup arm 200, specifically, to the fifth setup link 250 according to the first embodiment of the present disclosure.

The first joint 115 may rotatably couple the fifth setup link 250 to the first link 110. Here, the first link 110 may be formed to be rotatable around the yaw axis Y1 with respect to the fifth setup link 250.

Referring to FIG. 1 and FIGS. 4 to 41, in this case, the first link 110 of the active arm 100 may be coupled perpendicularly to the setup arm 200, specifically to the fifth setup link 250, which forms an angle of 20° with the horizontal plane, and the yaw axis Y1, which is the central axis of rotation of the first link 110, forms an angle of 70° with the horizontal plane.

That is, the yaw axis Y1 and a roll axis R are configured to be different from each other, and when the roll axis R of the surgical instrument 300 is positioned parallel to the horizontal plane, the yaw axis Y1 and the roll axis R are configured to form a predetermined angle therebetween rather than being parallel to each other.

That is, when the roll axis R of the surgical instrument 300 coupled to the fifth link 150 is positioned parallel to the horizontal plane, the yaw axis Y1 of the surgical robot arm 1 may be positioned to be inclined to form an angle of 70° with the roll axis R.

Accordingly, a gimbal lock phenomenon can be prevented, which may occur when the roll axis R and the yaw axis Y1 are positioned parallel or nearly parallel to each other when the surgical instrument 300 is disposed parallel to the horizontal plane.

The surgical robot arm 1 according to the first embodiment of the present disclosure allows the RCM to be positioned at various locations and enables the surgical instrument 300 to be disposed at various arbitrary angles, by the setup arm 200, which includes the plurality of setup links 210, 220, 230, 240, and 250.

That is, by the rotation of the plurality of setup links 210, 220, 230, 240, and 250 and the yaw rotation of the active arm 100, the RCM can be positioned in various locations, the active arm 100 can be disposed at various angles in various positions, and an entry angle of the surgical instrument 300 can be adjusted in various ways.

In other words, the presence of the setup arm 200 allows a distance between the body 201 and the surgical instrument 300 to be adjusted in various ways.

Referring to FIGS. 1 and 4, the surgical instrument 300 connected to the fifth link 150 may be disposed closer to the patient than the fifth link 150 of the active arm 100.

Accordingly, by ensuring that the fifth link 150 is not positioned between the patient and the surgical instrument 300, and arranging a plurality of surgical robot arms to surround the bed 500 on which the patient is lying, it is possible to prevent interference between the active arms 100 provided on different plurality of surgical robot arms 1.

Referring to FIGS. 1 and 4, among the plurality of setup links according to the first embodiment of the present disclosure, the setup links 210, 220, 230, and 240 that rotate around respective axes parallel to the Z-axis may be disposed at progressively higher levels as a distance from the body 201 to the active arm 100 increases.

Specifically, the second setup link 220 may be coupled to an upper surface (based on FIG. 4) of the first setup link 210 to be rotatable around the second setup joint 225, the third setup link 230 may be coupled to an upper surface of the second setup link 220 to be rotatable around the third setup joint 235, and the fourth setup link 240 may be coupled to an upper surface of the third setup link 230 to be rotatable around the fourth setup joint 245.

Accordingly, the fifth setup link 250 that rotates around the axis parallel to the X-axis is coupled to the fourth setup link 240 that is disposed relatively higher than the first setup link 210, the second setup link 220, and the third setup link 230, and the active arm 100, specifically the first link 110 is coupled to the fifth setup link 250 to be rotatable around the yaw axis Y1, and the RCM is formed on another side of the active arm 100, which is opposite to one side of the active arm 100 coupled to the fifth setup link 250, so that the yaw axis Y1 can be formed from top to bottom (based on FIG. 1).

Accordingly, the yaw axis Y1 and the roll axis R of the surgical instrument 300 coupled to the active arm 100, which will be described later, may be configured to be inclined at a relatively large angle, which may lead to the effect of preventing a gimbal lock phenomenon that may occur when the yaw axis Y1 and the roll axis R of the surgical instrument 300 are positioned parallel or nearly parallel to each other.

In addition, as the yaw axis Y1, which is positioned from the upper side to the lower side, and the roll axis R of the surgical instrument 300 form a predetermined angle with respect to each other, and the active arm 100 is disposed from the upper side to the lower side, the range of motion required for the surgical robot arm 1 to perform certain motions can be reduced.

Figure 21:
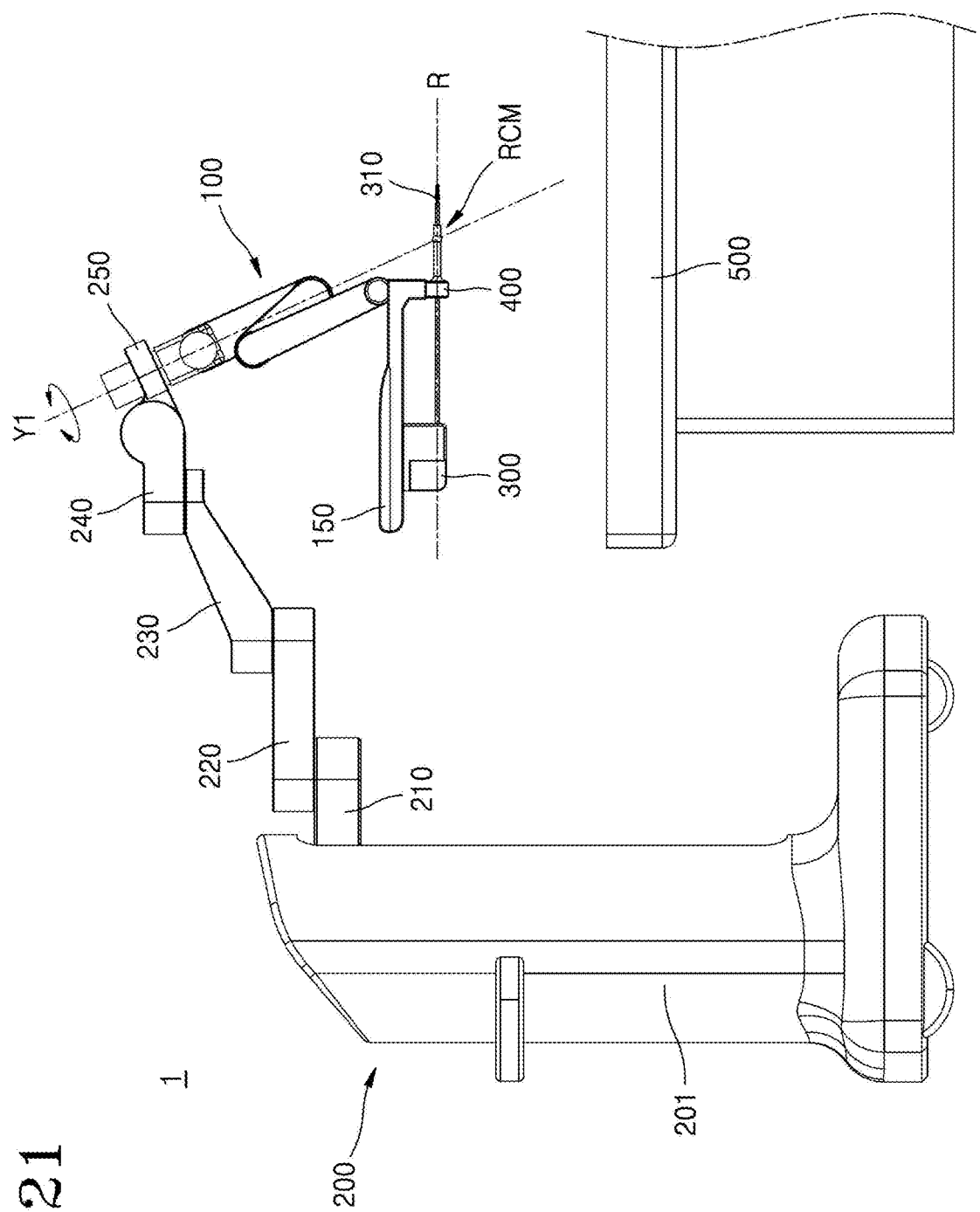
FIG. 21 is a side view illustrating the surgical robot arm of FIG. 20.
Figure 22:
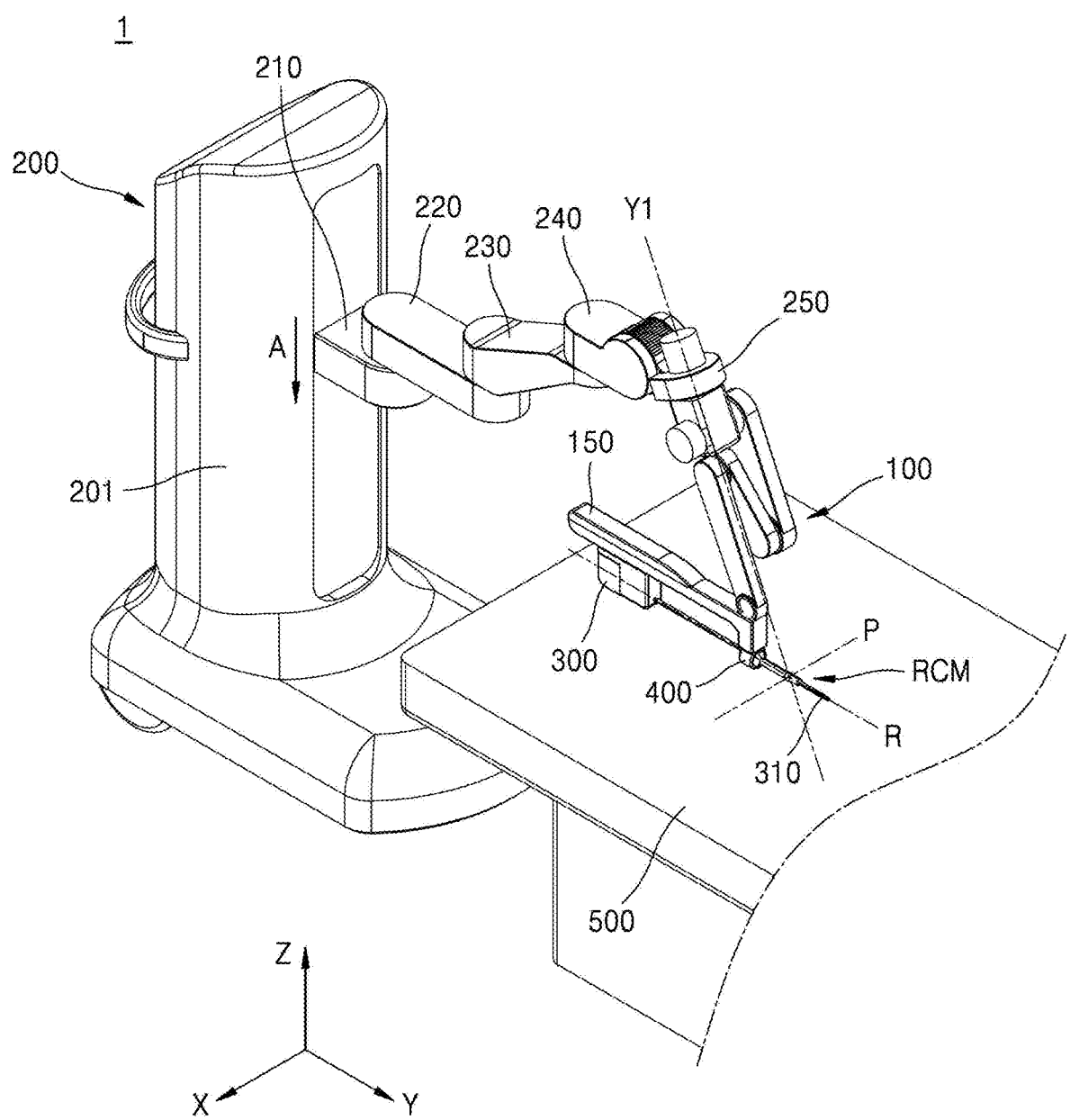
FIG. 22 is a perspective view illustrating a state in which the setup arm of the surgical robot arm according to the first embodiment of the present disclosure is lowered on the body.
Figure 23:
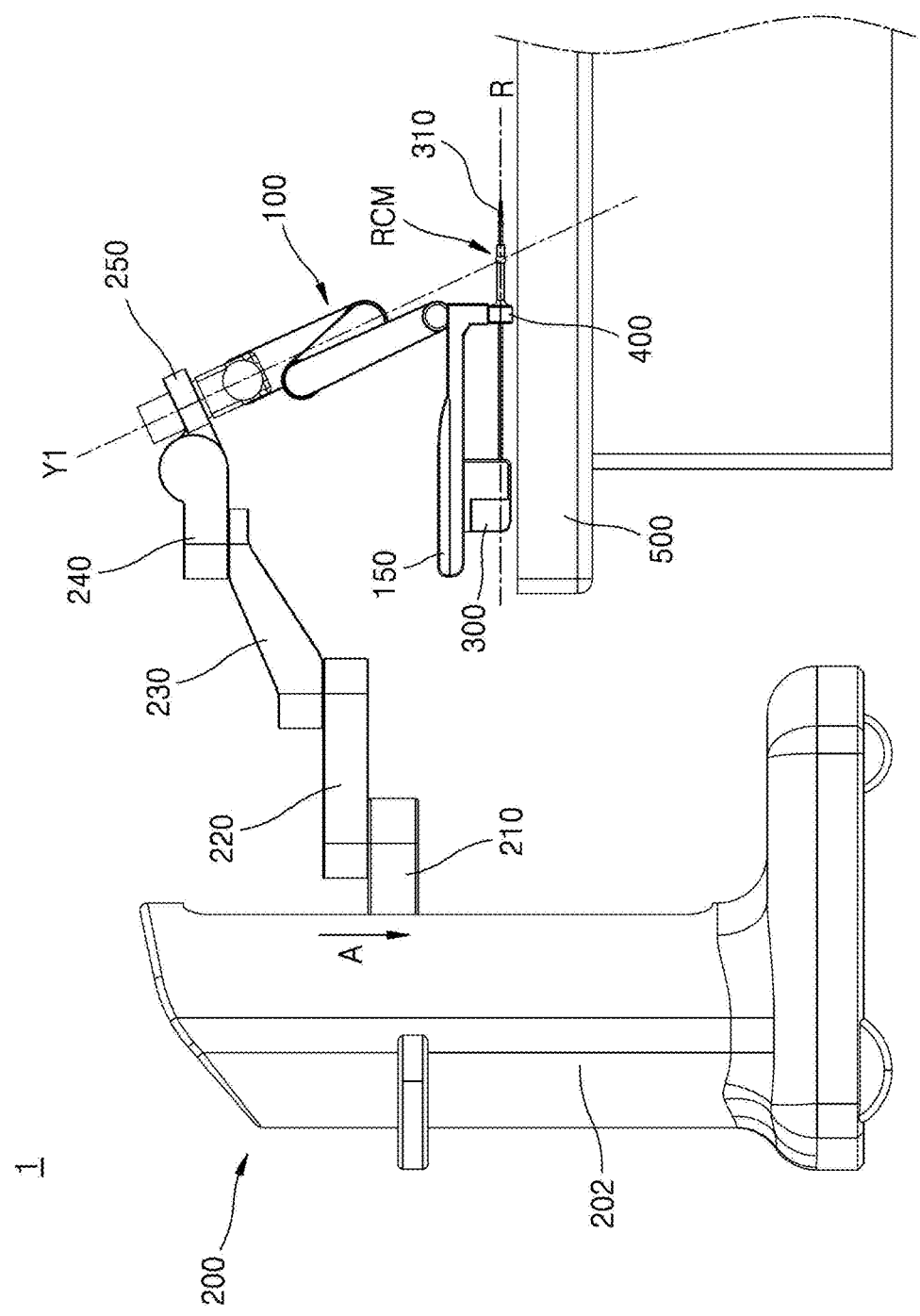
FIG. 23 is a side view illustrating the surgical robot arm of FIG. 22.

FIG. 20 is a perspective view illustrating a state in which the setup arm of the surgical robot arm according to the first embodiment of the present disclosure is raised on the body. FIG. 21 is a side view illustrating the surgical robot arm of FIG. 20. FIG. 22 is a perspective view illustrating a state in which the setup arm of the surgical robot arm according to the first embodiment of the present disclosure is lowered on the body. FIG. 23 is a side view illustrating the surgical robot arm of FIG. 22.

Referring to FIG. 20, the setup arm 200 according to the first embodiment of the present disclosure may include the body 201, the first setup link 210, the second setup link 220, the third setup link 230, the fourth setup link 240, and the fifth setup link 250.

The first setup link 210 is coupled to the body 201, and specifically by the first setup joint 215. The first setup joint 215 may be formed to allow vertical movement (movement in a Z-axis direction based on FIG. 20) with respect to the body 201.

Referring to FIG. 20, the fifth setup link 250 may rotate around the central axis of rotation, which is parallel to the X-axis, with respect to the fourth setup link 240, and may rotate with respect to the fourth setup link 240 to make a predetermined angle with the horizontal plane.

Specifically, in FIG. 4, the fifth setup link 250 is in a state of being rotated by 20° with respect to the horizontal plane relative to the fourth setup link 240.

Although not shown in the drawings, an elevation motor (not shown) may be provided in the body 201, and the elevation motor is connected to the first setup joint 215. When the elevation motor is driven, the first setup joint 215 and the first setup link 210 connected thereto may be raised and lowered in the Z-axis direction.

Referring to FIGS. 20 and 21, as the first setup link 210 is raised, the second setup link 220 connected to the first setup link 210, the third setup link 230 connected to the second setup link 220, the fourth setup link 240 connected to the third setup link 230, the fifth setup link 250 connected to the fourth setup link 240, and the active arm 100 connected to the fifth setup link 250 may move upward in the Z-axis direction (based on FIG. 20).

In this case, since the angle of the fifth setup link 250 with respect to the fourth setup link 240 is maintained at the predetermined angle, the position of the active arm 100 in the Z-axis direction may be changed while maintaining the angle formed between the yaw axis Y1, which is the central axis of rotation of the first link 110 to which the fifth setup link 250 is coupled, and the horizontal plane.

Referring to FIGS. 22 and 23, in contrast to FIGS. 20 and 21, the first setup link 210 moves from the upper side to the lower side (based on FIG. 22) in an A direction on the body 201, and during this movement, the angle between the yaw axis Y1 and the horizontal plane is maintained.

Figure 24:
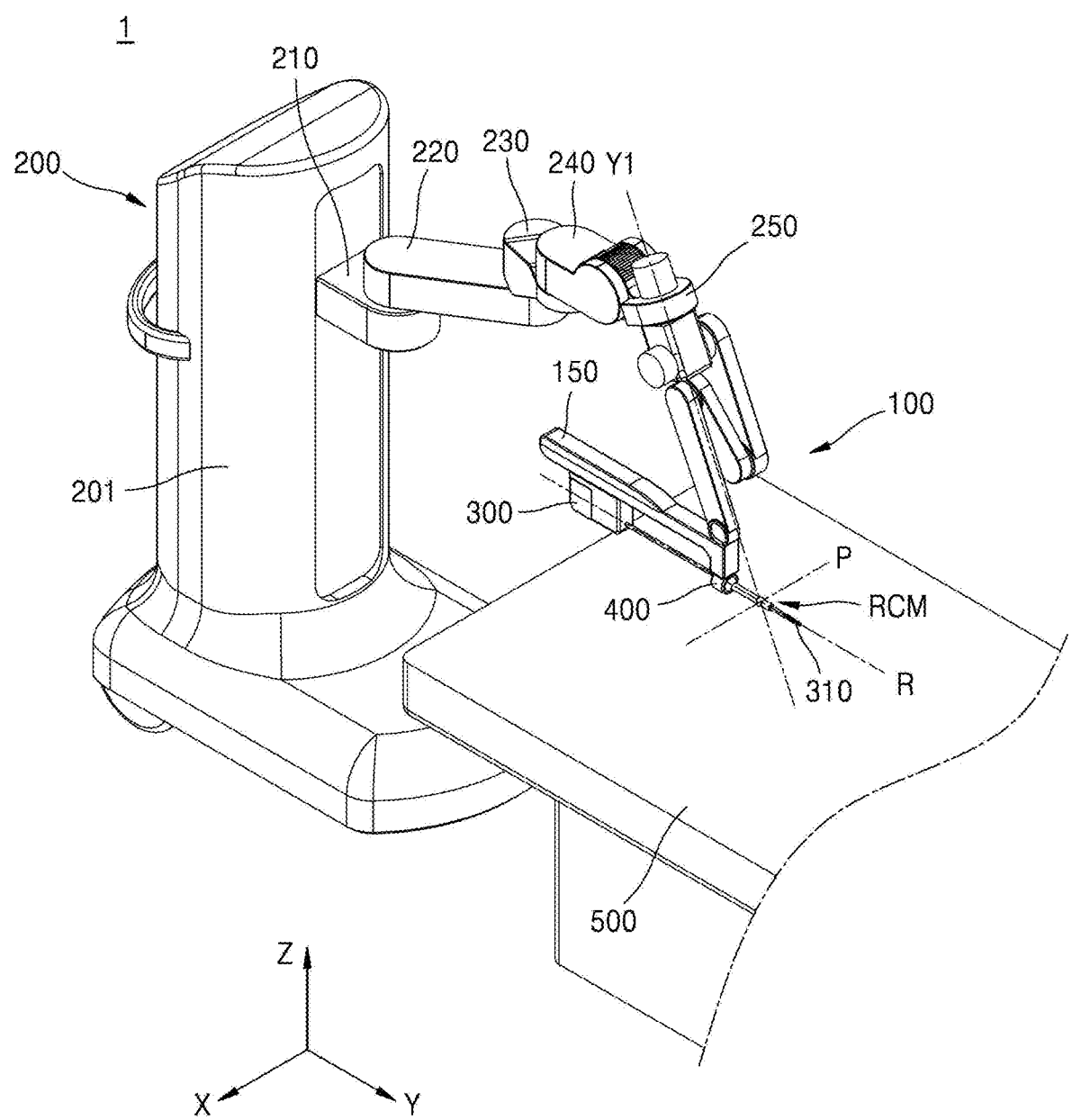
FIGS. 24 to 26 are views illustrating a first rotation state of the setup arm of the surgical robot arm according to the first embodiment of the present disclosure.
Figure 25:
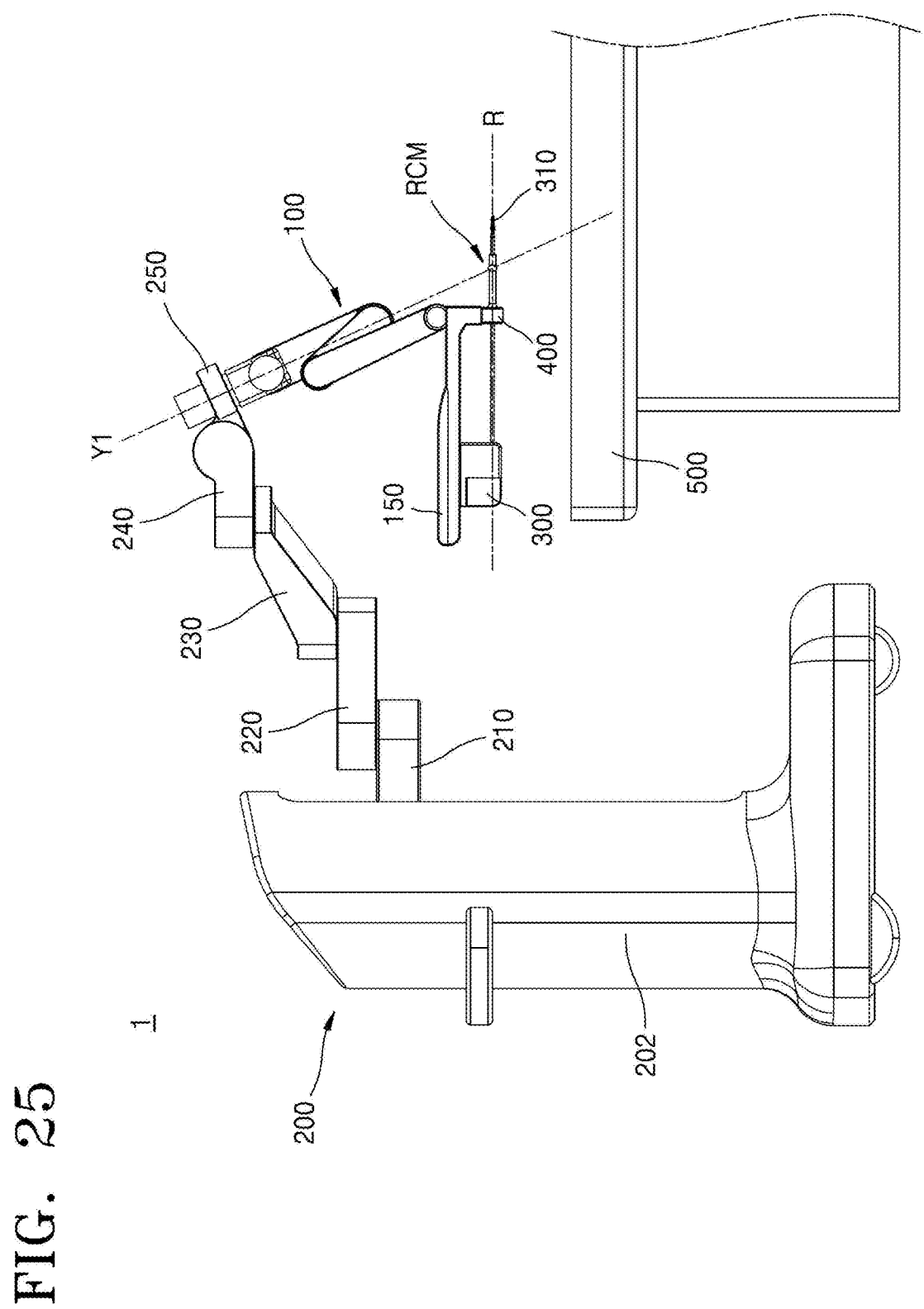
Figure 26:
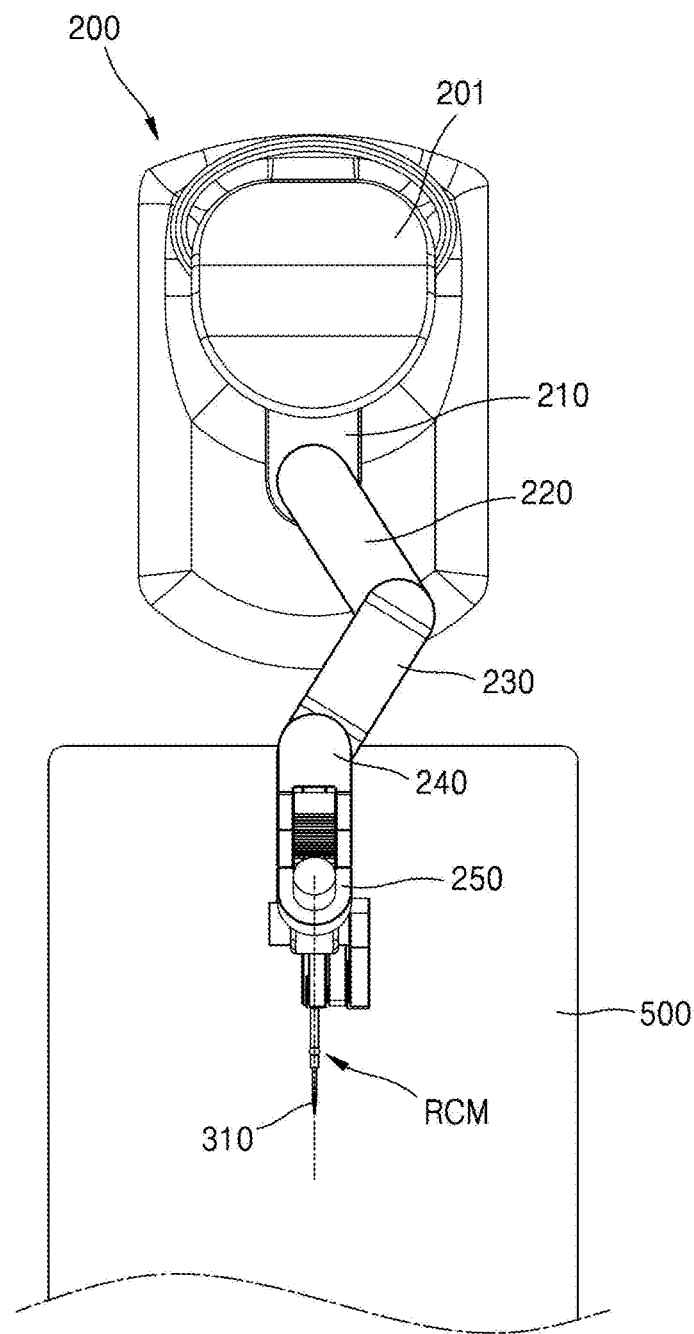

FIGS. 24 to 26 are views illustrating a first rotation state of the setup arm of the surgical robot arm according to the first embodiment of the present disclosure.

Referring to FIG. 24, the setup arm 200 according to the first embodiment of the present disclosure may include the body 201, the first setup link 210, the second setup link 220, the third setup link 230, the fourth setup link 240, and the fifth setup link 250.

The first setup link 210 is coupled to the body 201 by the first setup joint 215, the second setup link 220 is axially coupled to the first setup link 210 by the second setup joint 225, the third setup link 230 is axially coupled to the second setup link 220 by the third setup joint 235, the fourth setup link 240 is axially coupled to the third setup link 230 by the fourth setup joint 245, and the fifth setup link 250 is axially coupled to the fourth setup link 240 by the fifth setup joint 255.

The fifth setup link 250 is axially coupled to the fourth setup link 240, with an axis parallel to the pitch axis P of the active arm 100 (or parallel to the X-axis) as the central axis of rotation. Referring to FIG. 20, the fifth setup link 250 is coupled to the fourth setup link 240, forming a predetermined angle therebetween, for example, 20°. However, when the active arm 100 rotates around the yaw axis Y1 by a certain degree, the central axis of rotation of the fifth setup link 250 and the pitch axis P may no longer be parallel to each other.

FIG. 24 illustrates a state in which the second setup link 220, the third setup link 230, and the fourth setup link 240 are rotated around the respective central axes of rotation, allowing the RCM formed by the active arm 100 to move parallel in a preset direction (along the Y-axis based on FIG. 24).

That is, in a state as shown in FIG. 5, when the second setup link 220 is rotated by a predetermined angle with respect to the first setup link 210, the third setup link 230 is rotated by a predetermined angle with respect to the second setup link 220, and the fourth setup link 240 is rotated by a predetermined angle with respect to the third setup link 230, since the position between the second setup link 220 and the third setup link 230 is adjusted while the surgical instrument 300 is disposed in the direction shown in FIG. 5, the RCM is moved parallel along the Y-axis, specifically towards the body 201, Accordingly, the RCM can be positioned at various locations by the rotation of the plurality of setup links according to the first embodiment of the present disclosure. In addition, by rotating the first link 110 of the active arm 100 around the yaw axis Y1, the entry angle of the surgical instrument 300 can be changed in various ways while maintaining the RCM.

Figure 27:
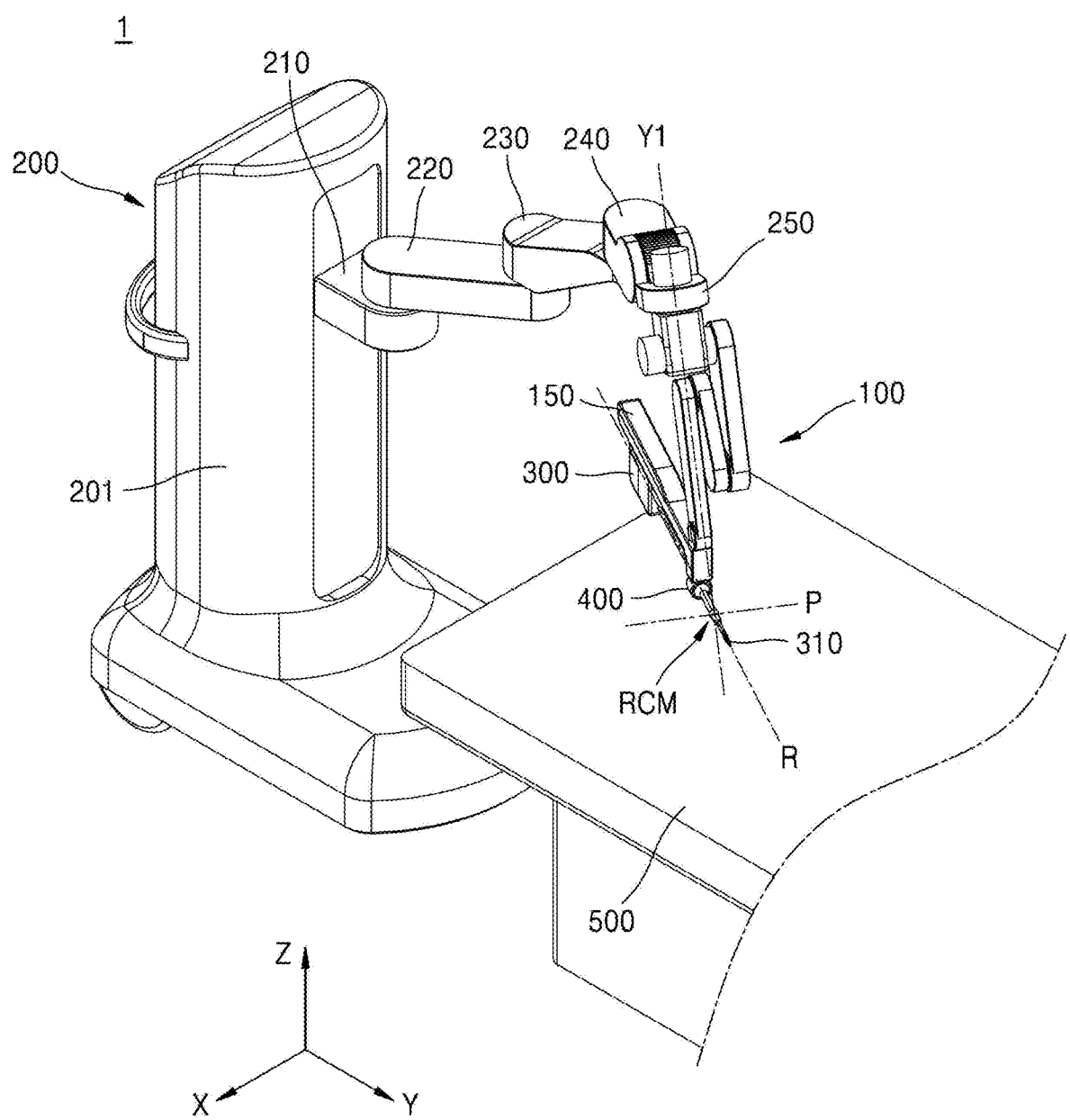
FIGS. 27 to 29 are views illustrating a second rotation state of the setup arm of the surgical robot arm according to the first embodiment of the present disclosure.
Figure 28:
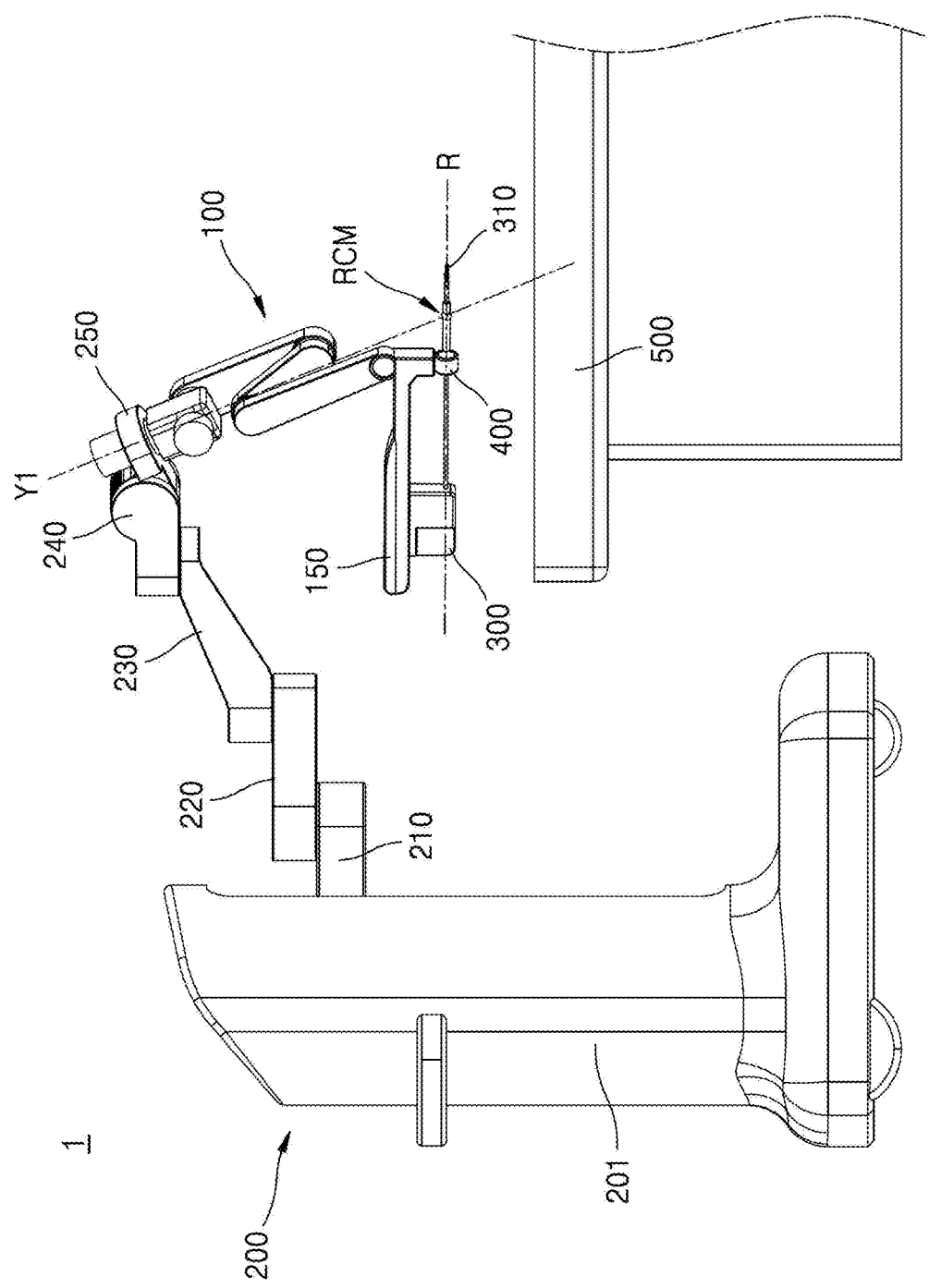
Figure 29:
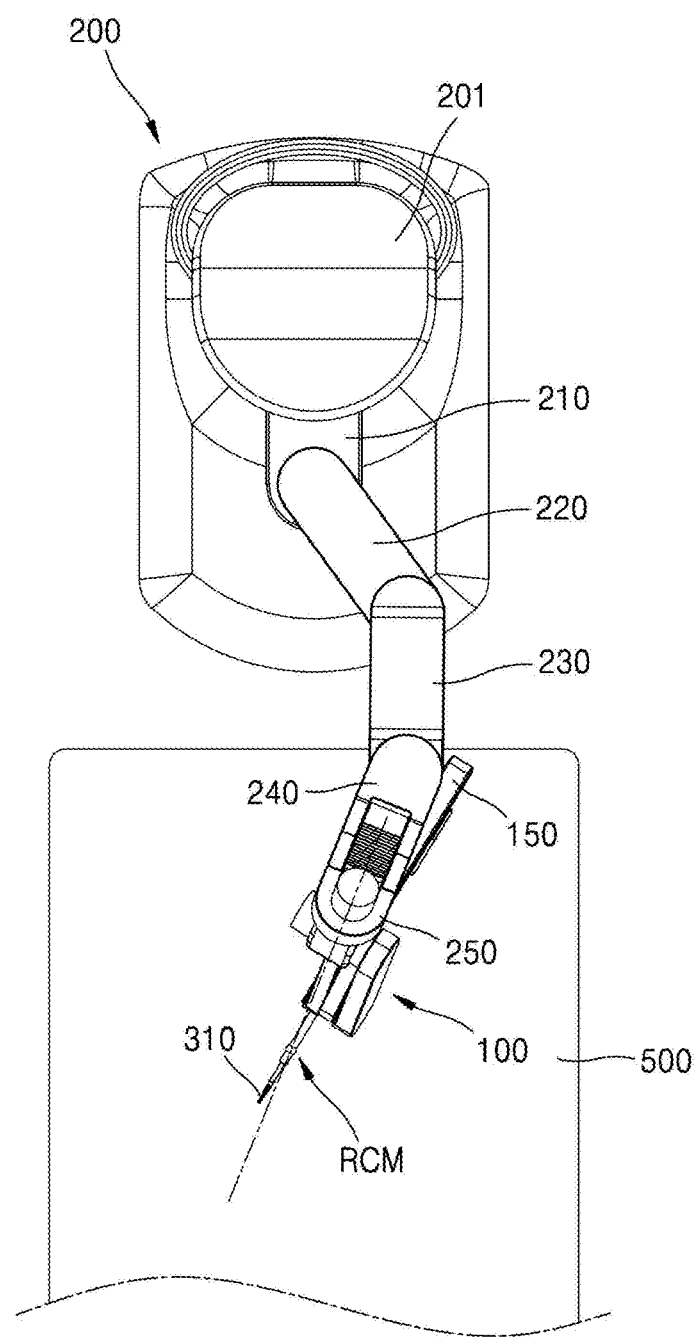

FIGS. 27 to 29 are views illustrating a second rotation state of the setup arm of the surgical robot arm according to the first embodiment of the present disclosure.

FIG. 27 illustrates a state in which the second setup link 220, the third setup link 230, and the fourth setup link 240 are each rotated to a certain degree, while the angle of the fifth setup link 250 with respect to the fourth setup link 240 remains fixed at a predetermined angle of 20°, as shown in FIG. 5.

FIGS. 27 to 29 illustrate that the second setup link 220, the third setup link 230, and the fourth setup link 240 can rotate while maintaining the RCM, and unlike in FIGS. 24 to 26, the direction of the surgical instrument 300 may be changed.

Referring to FIG. 29, as the position of the active arm 100 changes, the position of the surgical instrument 300 may also be changed, and accordingly, the entry angle of the surgical instrument 300 may change, while the position of the RCM remains the same as in FIG. 26.

Accordingly, in the first embodiment of the present disclosure, the entry angle of the instrument can be changed in various ways while maintaining the same RCM position through the rotation of the plurality of setup links.

In addition, by rotating the first link 110 of the active arm 100 around the yaw axis Y1, the entry angle of the surgical instrument 300 can be changed in more various ways while maintaining the RCM.

Figure 30:
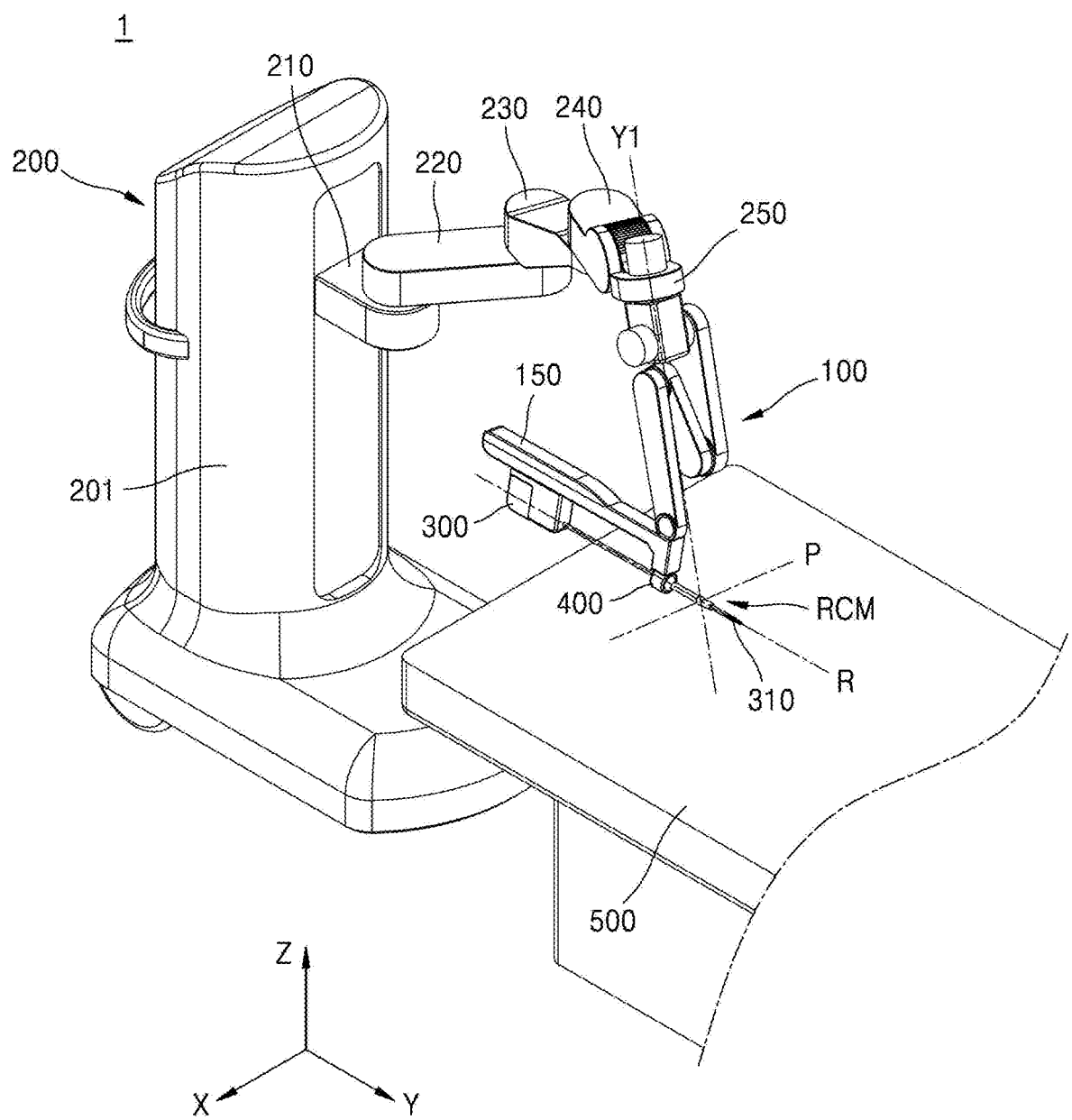
FIGS. 30 to 32 are views illustrating a third rotation state of the setup arm of the surgical robot arm according to the first embodiment of the present disclosure.
Figure 31:
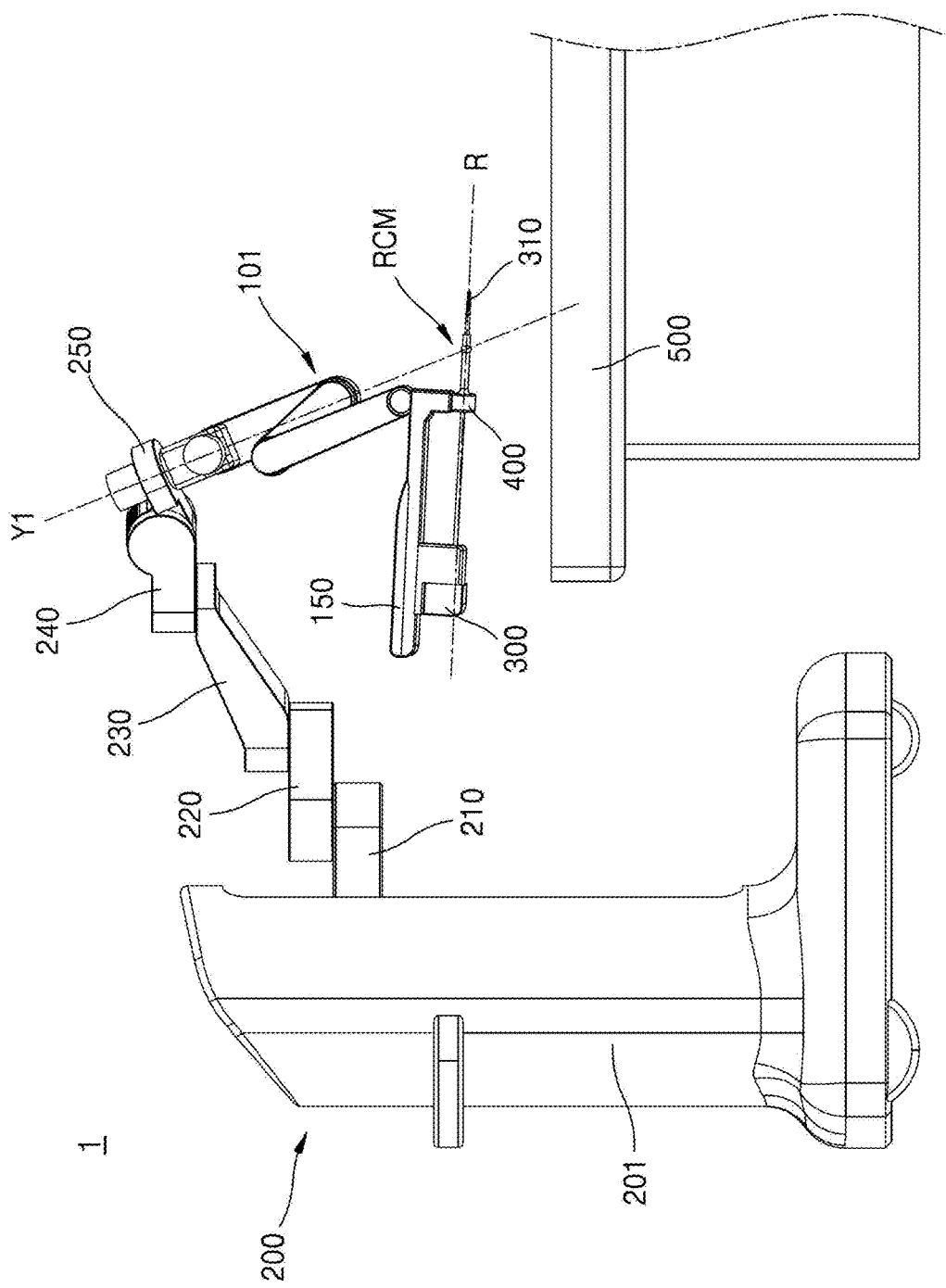
Figure 32:
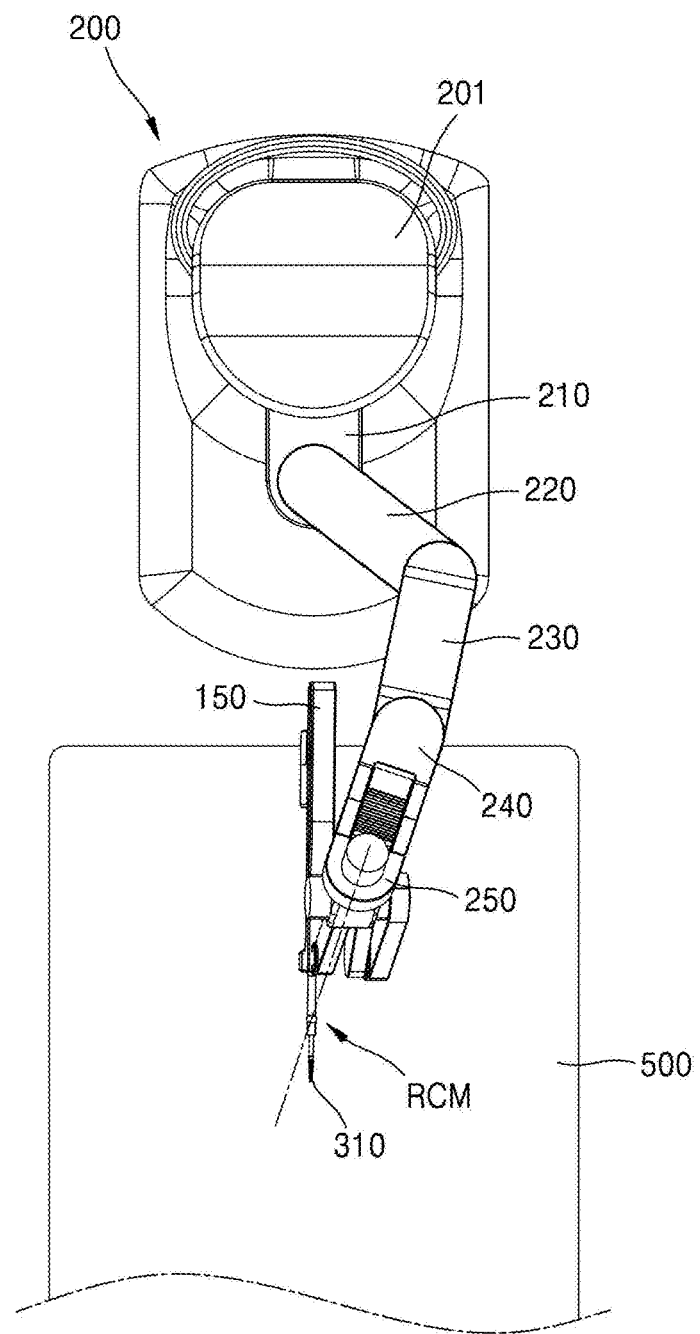

FIGS. 30 to 32 are views illustrating a third rotation state of the setup arm of the surgical robot arm according to the first embodiment of the present disclosure.

FIG. 30 illustrates a state in which the second setup link 220, the third setup link 230, and the fourth setup link 240 are rotated to a certain degree while the angle of the fifth setup link 250 with respect to the fourth setup link 240 is fixed at a predetermined angle of 20°, as shown in FIG. 5, and in addition thereto, the first link 110 of the active arm 100 is also rotated by a certain degree around the yaw axis Y1.

Referring to FIGS. 30 to 32, a plurality of setup links 220, 230, and 240 may be rotated while maintaining the RCM, and as the plurality of setup links 220, 230, and 240 rotate relative to each other, positions of a plurality of links 110, 120, 130, 140, and 150 of the active arm 100 coupled to the fifth setup link 250 may be changed.

At this time, a user may rotate the first link 110 of the active arm 100, which is rotatably connected to the fifth setup link 250, around the yaw axis Y1 to change the entry angle of the surgical instrument 300 to be the same as the entry angle before the change.

That is, the user can drive the active arm 100 such that the surgical instrument 300 enters at the same angle into the RCM as before the change even when the positions of the setup links 220, 230, and 240 are changed.

In addition, when performing surgery on a patient using a plurality of different surgical robot arms, changing spacing or forming an additional space between the body 201 and the active arm 100 of any one surgical robotic arm allows for the creation of a path for the surgical instrument coupled to the active arm of another surgical robot arm to enter.

In addition, there is no need to move the setup arm 200, specifically the body 201, to a different location to create the above space, and instead, by rotating the setup arm 200, specifically, the plurality of setup links disposed between the body 201 and the active arm 100, the time required to move surgical instruments, such as the surgical robot arm 1, can be eliminated, thereby reducing the surgery time.

Figure 33:
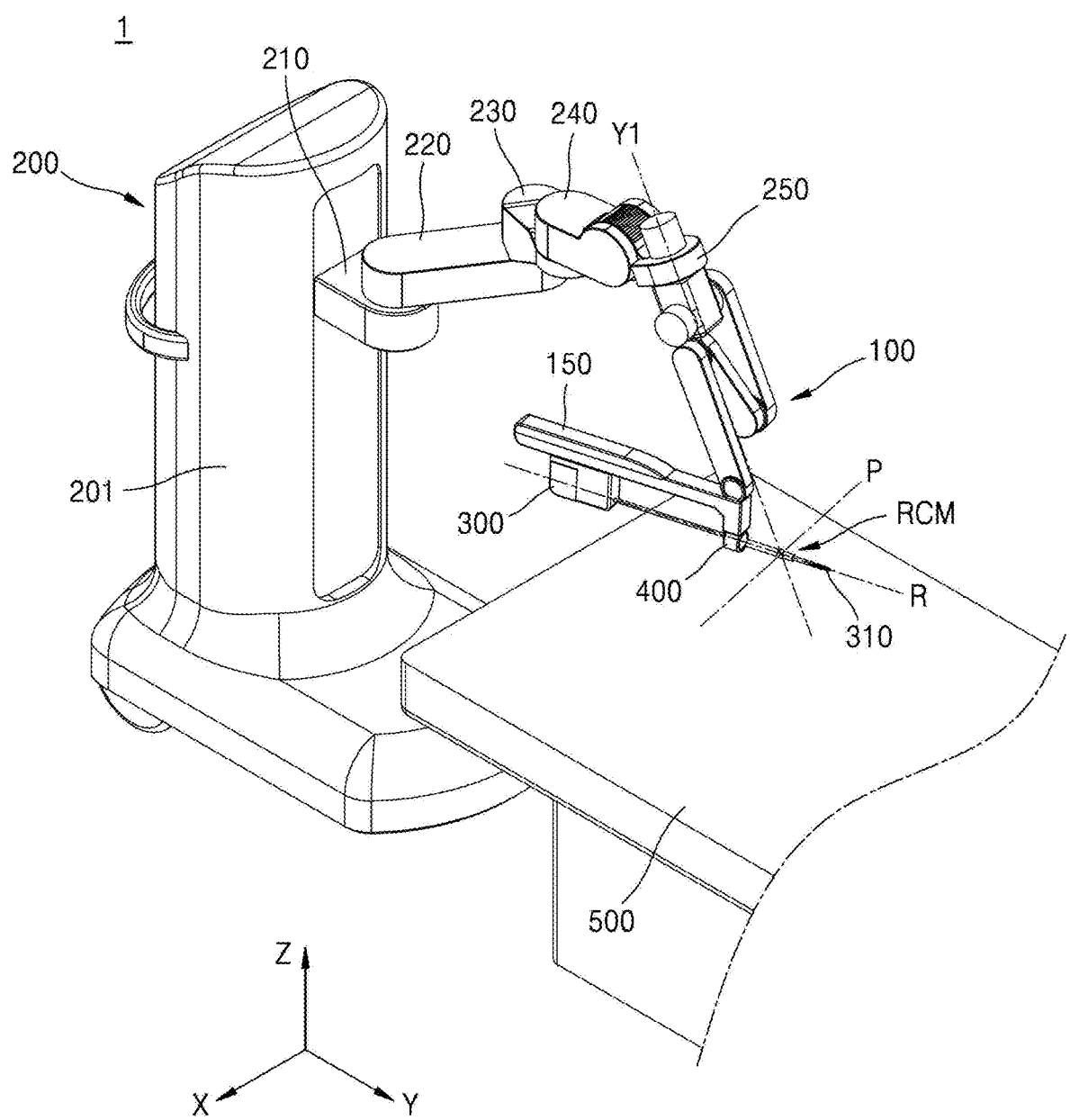
FIGS. 33 to 35 are views illustrating an exemplary first arrangement state of the surgical robot arm according to the first embodiment of the present disclosure.
Figure 34:
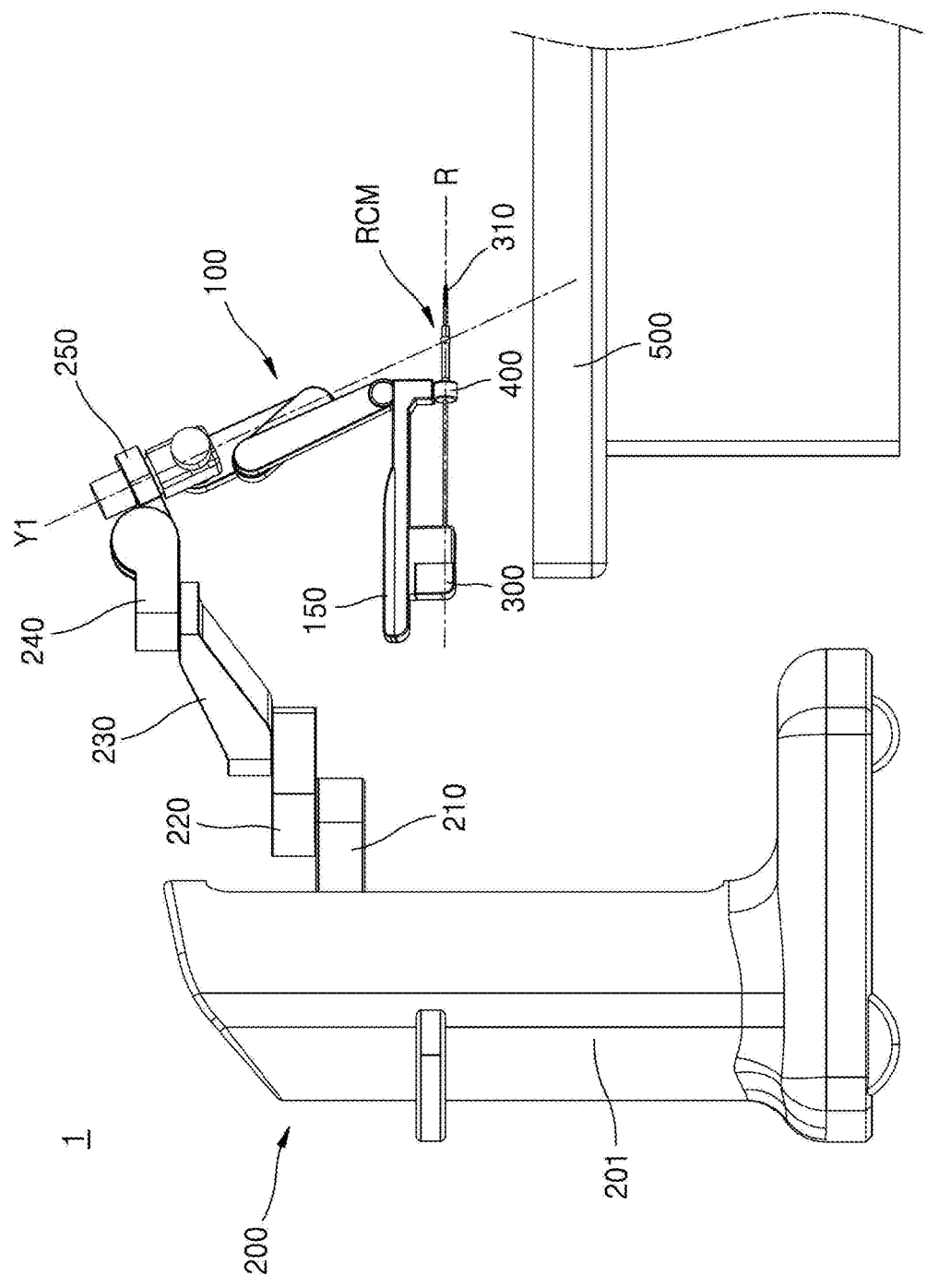
Figure 35:
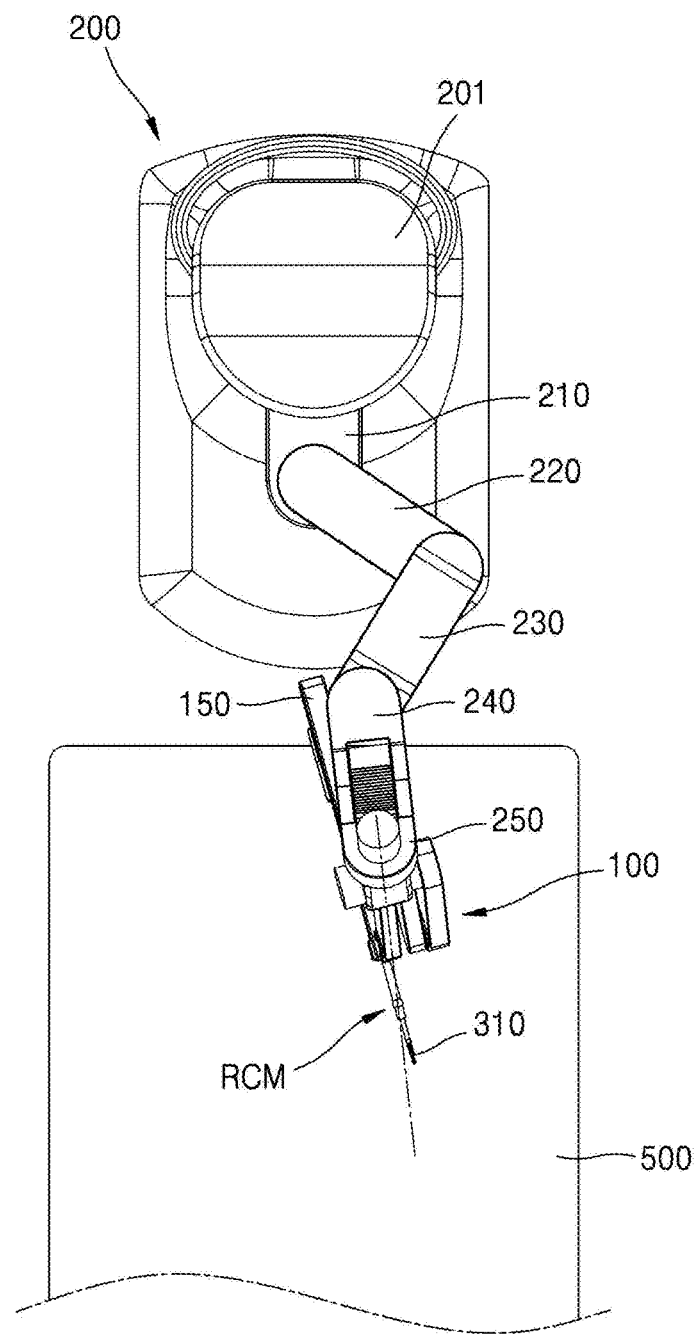
Figure 36:
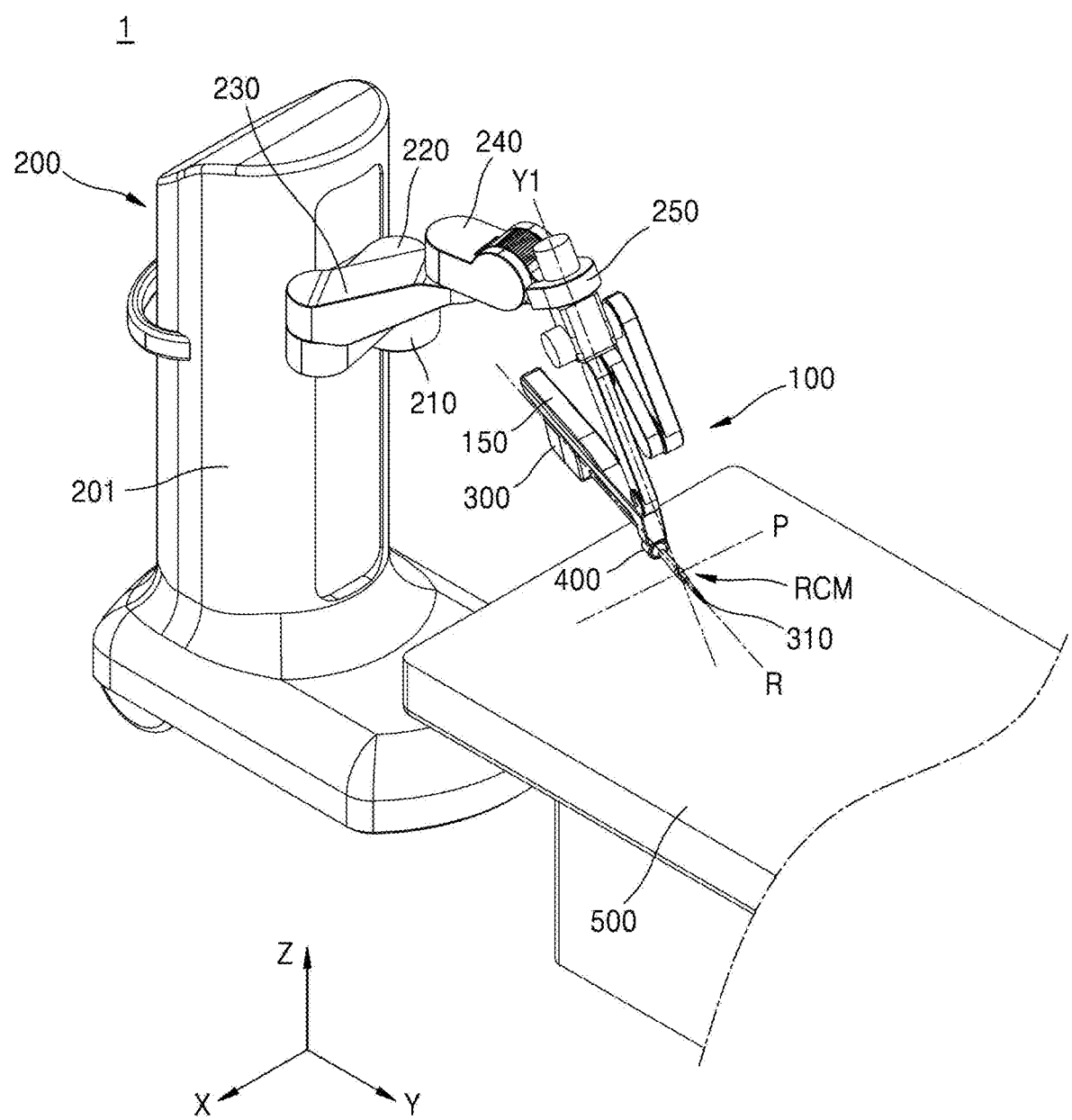
FIGS. 36 to 38 are views illustrating an exemplary second arrangement state of the surgical robot arm according to the first embodiment of the present disclosure.
Figure 37:
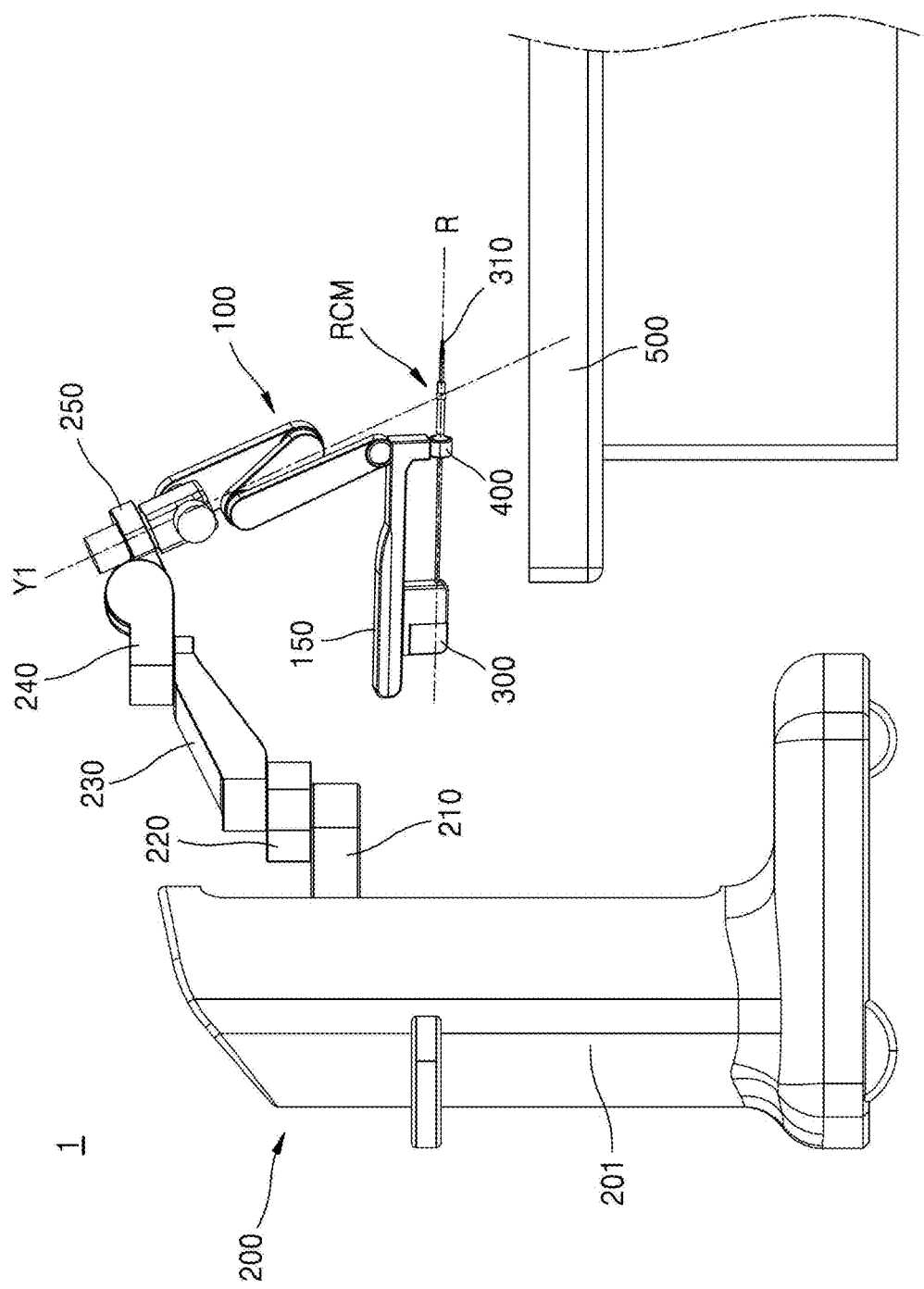
Figure 38:
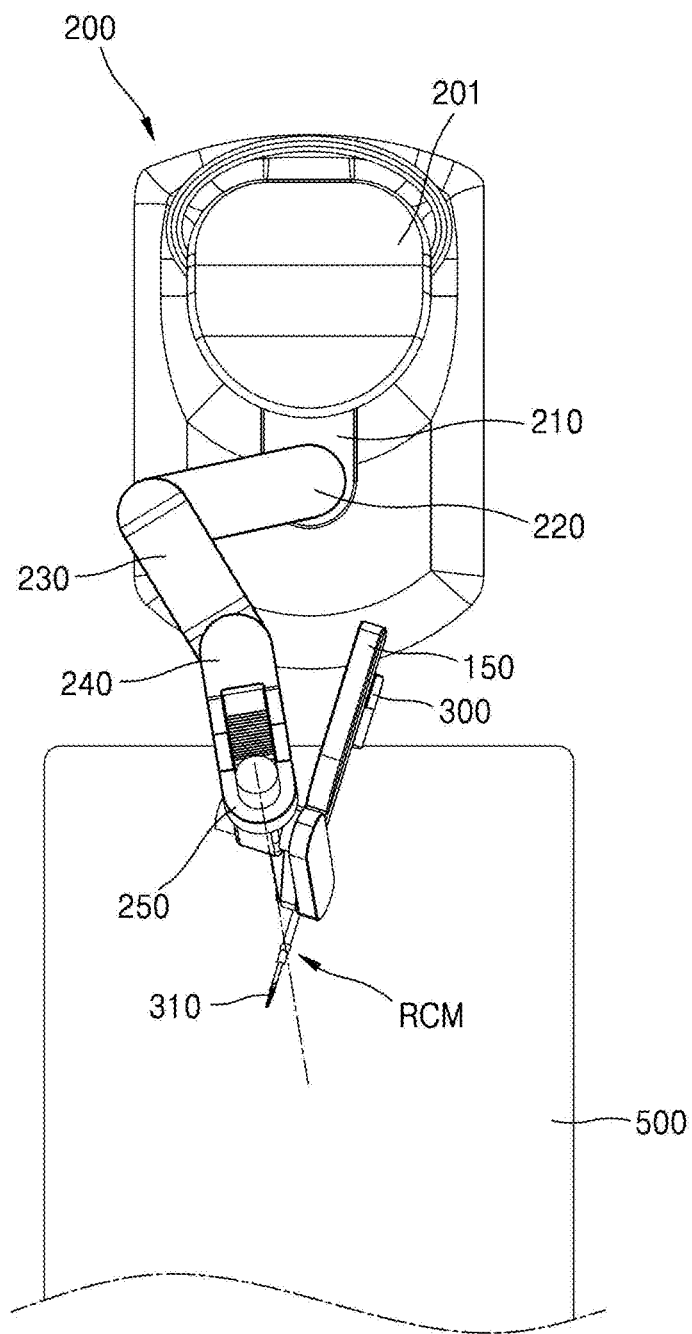
Figure 39:
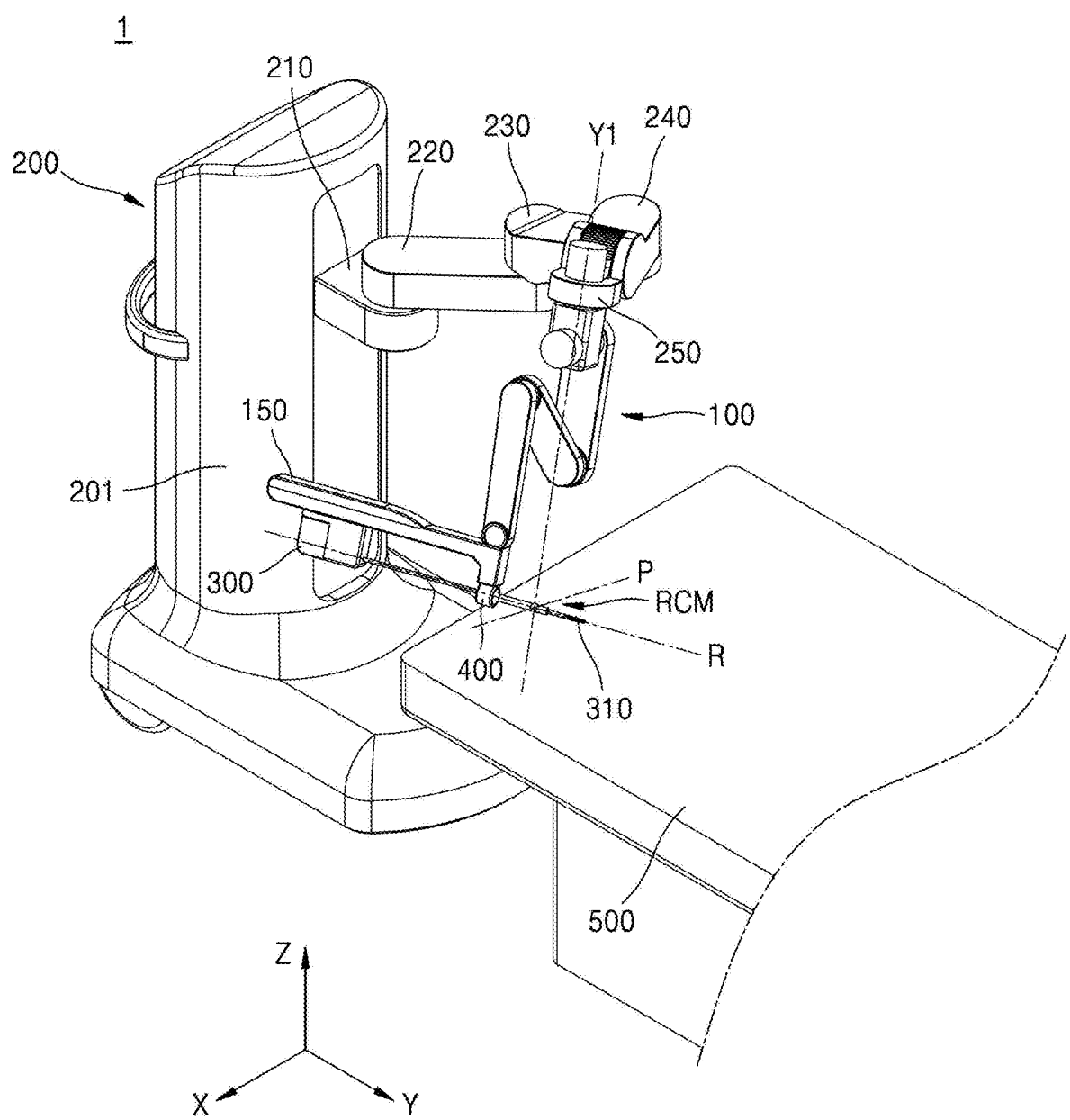
FIGS. 39 to 41 are views illustrating an exemplary third arrangement state of the surgical robot arm according to the first embodiment of the present disclosure.
Figure 40:
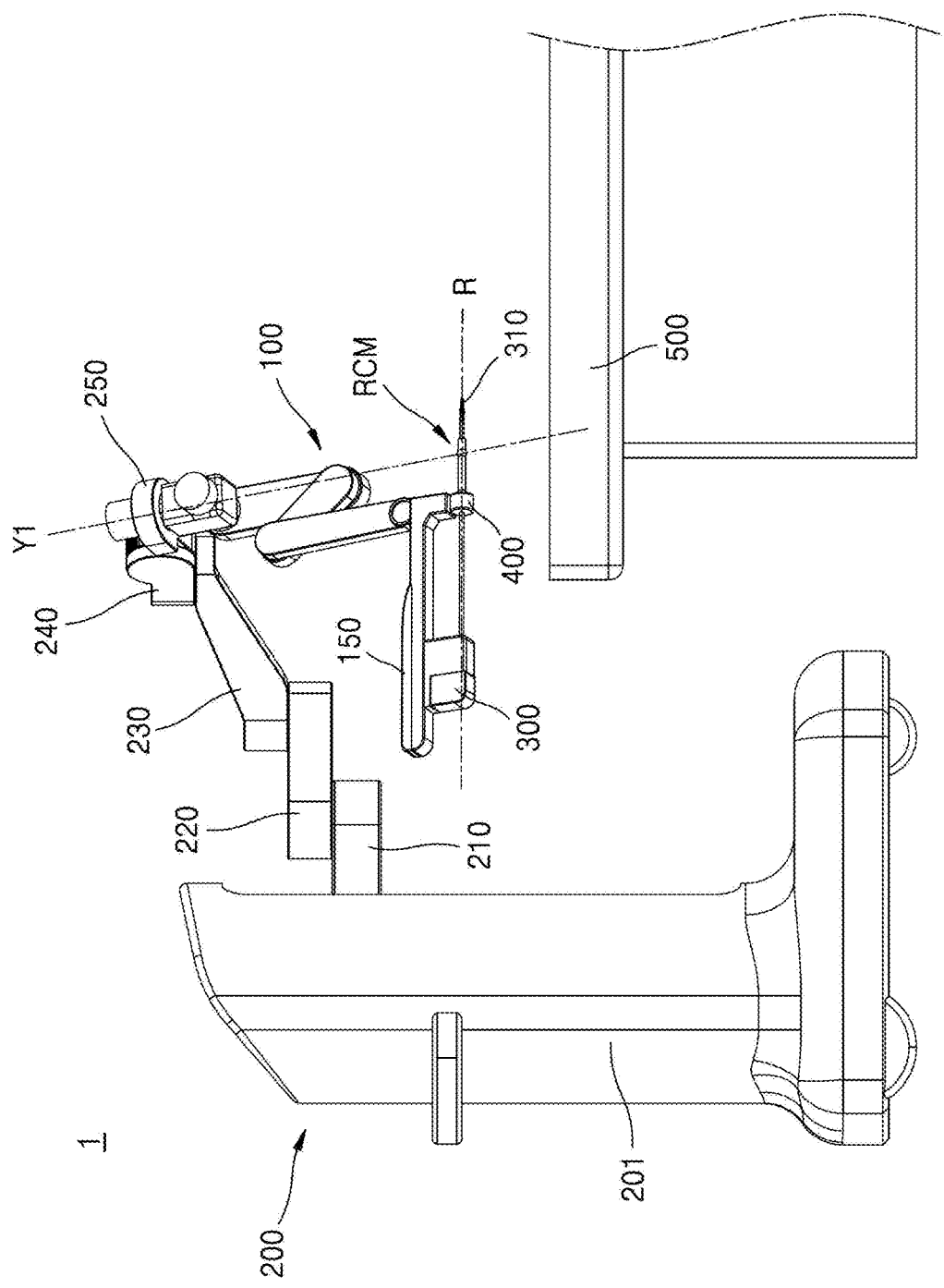
Figure 41:
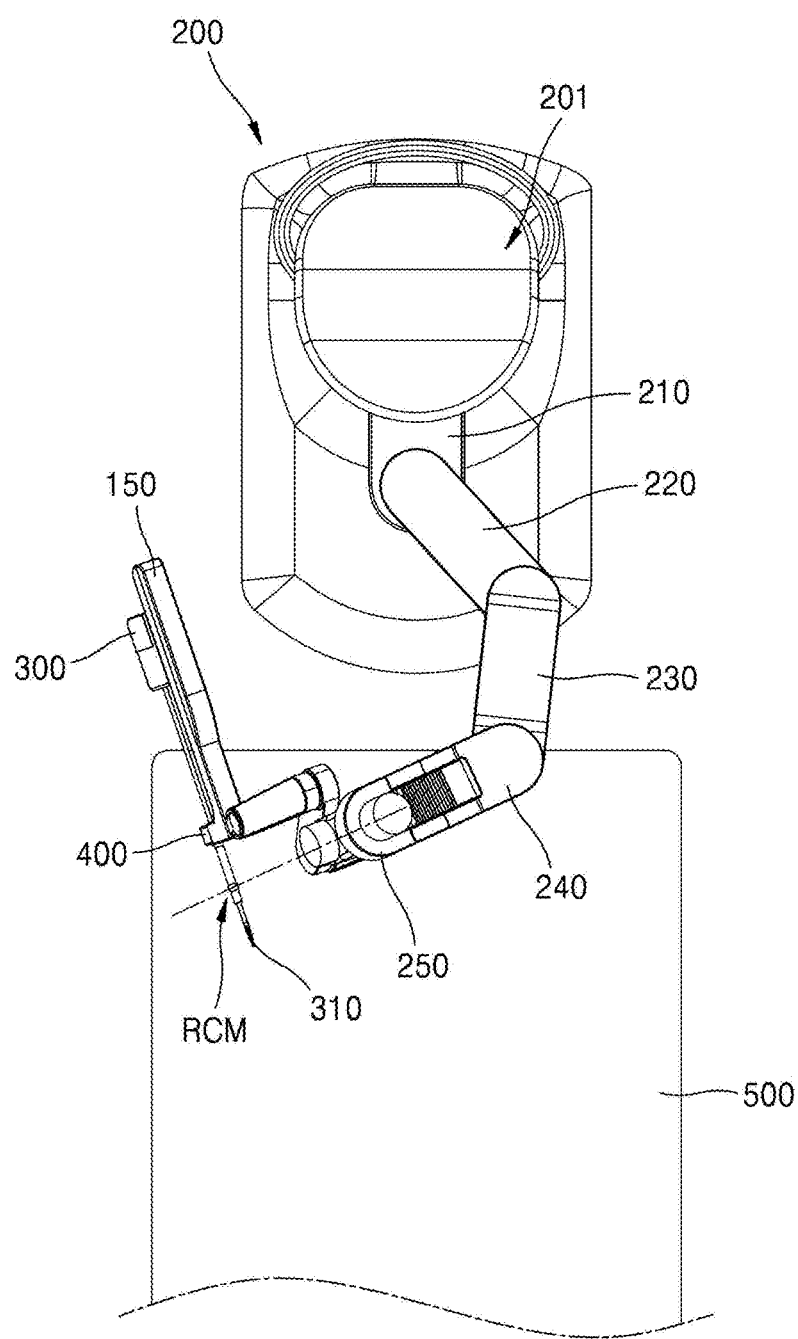

FIGS. 33 to 35 are views illustrating an exemplary first arrangement state of the surgical robot arm according to the first embodiment of the present disclosure. FIGS. 36 to 38 are views illustrating an exemplary second arrangement state of the surgical robot arm according to the first embodiment of the present disclosure. FIGS. 39 to 41 are views illustrating an exemplary third arrangement state of the surgical robot arm according to the first embodiment of the present disclosure.

Referring to FIGS. 33 to 41, the surgical robot arm 1 according to the first embodiment of the present disclosure is in a state in which the position of the first setup link 210 is fixed on the body 201, that is, a height of the setup arm 200 in the Z-axis direction is fixed, and a rotation angle of the fifth setup link 250 with respect to the fourth setup link 240 is also fixed at a predetermined angle of 20°.

At this time, the position of the RCM can be changed in various ways by rotating the second setup link 220 by a predetermined angle with respect to the first setup link 210, rotating the third setup link 230 by a predetermined angle with respect to the second setup link 220, and rotating the fourth setup link 240 by a predetermined angle with respect to the third setup link 230.

In addition, as the active arm 100 coupled to the setup arm 200, specifically the first link 110 coupled to the fifth setup link 250 rotates around the yaw axis Y1 serving as a rotation center, the position of the surgical instrument 300 can be changed while the third joint 135, the fourth joint 145, the fifth joint 155, and the RCM maintain a parallelogram as described above, with the position of the RCM remaining fixed.

As the position of the surgical instrument 300 changes, the roll axis R of the surgical instrument 300 may be changed, the entry angle of the surgical instrument 300 may also be changed, thereby allowing for various arrangements of the surgical instrument 300 at any entry angle.

(Motions of Active Arm of Surgical Robot Arm)

Referring to FIGS. 1 and 4, the active arm 100 is coupled to the setup arm 200, and may have the surgical instrument 300 and the trocar 400 coupled thereto. The active arm 100 may be the part that is adjusted in position in a pre-surgery stage, is coupled to an end portion of the setup arm 200, which is fixed in place and remains stationary, and during surgery, moves in real-time under the manipulation of the surgeon.

In the surgical robot arm 1 according to the first embodiment of the present disclosure, a virtual pivot center point is set at a predetermined position on a distal end of the surgical instrument 300 mounted on the active arm 100, which is coupled to one end portion of the setup arm 200 that is fixed in place, and the active arm 100 is controlled to rotate the surgical instrument 300 around the virtual pivot center point, which is referred to as the RCM.

Before describing the active arm 100, the RCM mechanism will be briefly described below.

(Conceptual View of RCM-Link Structure)

As an example of the RCM mechanism of the present disclosure, a linkage structure may be applied. FIG. 2 is a diagram illustrating operational states of an RCM mechanism with a linkage structure. FIG. 4 is a view illustrating an example in which the RCM mechanism with a linkage structure is applied to the surgical robot arm of FIG. 1.

In the case of such a linkage structure, the active arm 100 of the surgical robot arm 1 according to the first embodiment of the present disclosure may include the first link 110, the second link 120, the third link 130, the fourth link 140, and the fifth link 150.

In addition, the active arm 100 may further include a third-1 link 130-1 and a fourth-1 link 140-1. In addition, the active arm 100 may include the first joint 115, the second joint 125, the third joint 135, the fourth joint 145, and the fifth joint 155.

Referring to FIG. 2, when the third link 130 rotates around the third joint 135 with respect to the second link 120, the third link 130, the fourth link 140, and the third-1 link 130-1, which are links forming a parallelogram, rotate together. At this time, even when the links rotate, the parallelogram is maintained, so that the third link 130 and the third-1 link 130-1 remain parallel in any rotational state.

Meanwhile, when the fourth link 140 rotates around the fourth joint 145 with respect to the third link 130, the third link 130, the fourth link 140, the fifth link 150, and the fourth-1 link 140-1, which form a parallelogram, rotate together.

At this time, even when the links rotate, the parallelogram is maintained, so that the fourth link 140 and the fourth-1 link 140-1 remain parallel in any rotational state.

As described above, as the third link 130 rotates around the third joint 135, the fourth link 140 also rotates with respect to the third link 130 in conjunction therewith, causing an extension line connecting the third joint 135 to the RCM to remain parallel to the fourth link 140.

Similarly, in conjunction with the rotation of the fourth link 140 with respect to the third link 130, the fifth link 150 also rotates with respect to the fourth link 140, so that the third link 130 and the fifth link 150 remain parallel. As a result, the RCM remains constant regardless of the motion state.

(Conceptual View of RCM-Belt Structure)

As an example of the RCM mechanism of the present disclosure, a belt structure may be applied. FIG. 3 is a diagram illustrating operational states of an RCM mechanism with a belt structure.

In the case of such a belt structure, the active arm 100 of the surgical robot arm 1 according to the first embodiment of the present disclosure may include the first link 110, the second link 120, the third link 130, the fourth link 140, and the fifth link 150. In addition, the active arm 100 of the surgical robot arm 1 may include the first joint 115, the second joint 125, the third joint 135, the fourth joint 145, and the fifth joint 155.

Here, the second joint 125 may include a pulley 192, the third joint 135 may include a pulley 193-1 and a pulley 193-2, the fourth joint 145 may include a pulley 194-1 and a pulley 194-2, and the fifth joint 155 may include a pulley 195.

Here, each of the pulley 192, the pulley 193-1, the pulley 194-1, and the pulley 195 may be a rotational pulley that rotates around a central axis thereof. Meanwhile, the pulley 193-2 and the pulley 194-2 may be fixed pulleys that do not rotate.

Further, the active arm 100 of the surgical robot arm 1 may further include a first belt 181, a second belt 182, and a third belt 183.

Here, the first belt 181 may connect the pulley 192 to the pulley 193-1. The second belt 182 may connect the pulley 193-2 to the pulley 194-1. The third belt 183 may connect the pulley 194-2 to the pulley 195.

Referring to FIG. 3, the pulley 192, which is a rotational pulley, may be connected to a motor (not shown) and may be formed to be rotatable with respect to the second link 120. In addition, it may be assumed that each pulley and each belt are fixedly coupled at one or more points so that no slippage occurs.

First, the pulley 193-1, which is a rotational pulley, is formed to be rotatable with respect to the second link 120, and is integrally formed with the third link 130. Thus, when the pulley 193-1 rotates with respect to the second link 120, the third link 130, which is integrally formed with the pulley 193-1, rotates with respect to the second link 120.

Meanwhile, the pulley 193-2, which is a fixed pulley, is integrally formed with the second link 120.

Meanwhile, the pulley 194-1, which is a rotational pulley, is formed to be rotatable with respect to the third link 130, and is integrally formed with the fourth link 140. Thus, when the pulley 194-1 rotates with respect to the third link 130, the fourth link 140, which is integrally formed with the pulley 194-1, rotates with respect to the third link 130.

Meanwhile, the pulley 194-2, which is a fixed pulley, is integrally formed with the third link 130.

Meanwhile, the pulley 195, which is a rotational pulley, is formed to be rotatable with respect to the fourth link 140, and is integrally formed with the fifth link 150. Thus, when the pulley 195 rotates with respect to the fourth link 140, the fifth link 150, which is integrally formed with the pulley 195, rotates with respect to the fourth link 140.

In this case, the two pulleys belted together must have diameters equal to each other so that the RCM is maintained. That is, {diameter of pulley 192=diameter of pulley 193-1}, {diameter of pulley 193-2=diameter of pulley 194-1}, and {diameter of pulley 194-2=diameter of pulley 195} should be satisfied.

Operations of the above-described belt-structured RCM mechanism will be described.

First, when the pulley 192 connected to the motor (not shown) rotates, the pulley 193-1 connected to the pulley 192 through the belt 181 also rotates.

In addition, when the pulley 193-1 rotates, the third link 130 integrally formed with the pulley 193-1 rotates with respect to the second link 120.

In this case, since the third link 130 rotates with respect to the second link 120 in a state in which the pulley 193-2 is fixed to the second link 120, the belt 182 rotates relative to the pulley 193-2.

In addition, when the belt 182 rotates, the pulley 194-1 rotates with respect to the third link 130, and when the pulley 194-1 rotates, the fourth link 140 integrally formed with the pulley 194-1 rotates with respect to the third link 130.

As described above, as the third link 130 rotates around the third joint 135, the fourth link 140 also rotates with respect to the third link 130 in conjunction therewith, causing the extension line connecting the third joint 135 to the RCM to remain parallel to the fourth link 140.

In addition, since the fourth link 140 rotates with respect to the third link 130 in a state in which the pulley 194-2 is fixed to the third link 130, the belt 183 rotates relative to the pulley 194-2.

In addition, when the belt 183 rotates, the pulley 195 rotates with respect to the fourth link 140, and when the pulley 195 rotates, the fifth link 150 integrally formed with the pulley 195 rotates with respect to the fourth link 140.

As described above, in conjunction with the rotation of the fourth link 140 with respect to the third link 130, the fifth link 150 also rotates with respect to the fourth link 140, so that the third link 130 and the fifth link 150 remain parallel.

As a result, the RCM remains constant regardless of the motion state.

Hereinafter, the active arm 100 of the surgical robot arm 1 according to the first embodiment of the present disclosure will be described.

Referring to FIGS. 1, 4 to 17, the active arm 100 of the surgical robot arm 1 according to the first embodiment of the present disclosure may include the first link 110, the second link 120, the third link 130, the fourth link 140, and the fifth link 150.

In addition, the active arm 100 may include the first joint 115, the second joint 125, the third joint 135, the fourth joint 145, and the fifth joint 155.

Referring to FIGS. 1 and 4, the first joint 115 rotatably couples the fifth setup link 250 to the first link 110. In detail, the first joint 115 is formed to allow the first link 110 to yaw-rotate around the yaw axis Y1, which serves as a rotation center and is formed to pass through the RCM.

As a result, regardless of the degree to which the first link 110 yaw-rotates with respect to the fifth setup link 250, the position and orientation of the RCM with respect to the fifth setup link 250 remain constant.

The second joint 125 connects the second link 120 to the first link 110. In this case, since the second link 120 is fixedly coupled to the first link 110, a relative position of the second link 120 with respect to the first link 110 may be constant.

In this case, the second joint 125 may include a motor (not shown) and may be connected to the third joint 135 by a belt, wire, or the like. Accordingly, a driving force of the second joint 125 can be transmitted to the third joint 135.

Although not shown in the drawing, various modifications are possible, such as having the second joint 125 without a motor, while the third joint 135 includes a motor so that a driving force of the third joint 135 can be transmitted to the second joint 125.

The third link 130 is axially coupled to the second link 120 so as to be rotatable around the third joint 135 with respect to the second link 120. Here, the third joint 135 may include one or more pulleys.

The fourth link 140 is axially coupled to the third link 130 so as to be rotatable around the fourth joint 145 with respect to the third link 130. Here, the fourth joint 145 may include one or more pulleys.

The fifth link 150 is axially coupled to the fourth link 140 so as to be rotatable around the fifth joint 155 with respect to the fourth link 140. Here, the fifth joint 155 may include one or more pulleys.

Referring to FIGS. 1 and 4, the surgical instrument 300 is coupled to the fifth link 150. At this time, at least a portion of the surgical instrument 300 may be formed to be rotatable around the roll axis R (i.e., a shaft axis).

In addition, the surgical instrument 300 may be formed to allow reciprocating linear motion along the roll axis R with respect to the fifth link 150. Here, the roll axis R of the surgical instrument 300 coupled to the fifth link 150 is configured to pass through the RCM.

Referring to FIG. 4, the third joint 135, the fourth joint 145, the fifth joint 155, and the RCM may be four vertices of a parallelogram. That is, the third joint 135, the fourth joint 145, the fifth joint 155, and the RCM may form a single parallelogram.

In such a structure, once the surgical robot arm 1 is set up by manipulating the setup arm 200, which will be described later, the RCM will always remain in its position. In addition, as each link rotates around the RCM, the parallelogram is maintained regardless of the position of each link.

In order to maintain the RCM as described above, the fourth joint 145 and the fifth joint 155 are connected to each other to be rotatable around the third joint 135. Various power transmission devices, such as belts, wires, and links, may be used to connect the third joint 135, the fourth joint 145, and the fifth joint 155 to each other.

For example, a rotation of the third joint 135 and a rotation of the fourth joint 145 may be interlocked by a belt, so that a rotation of the third link 130 with respect to the second link 120 may cause a rotation of the fourth link 140 with respect to the third link 130.

At the same time, the rotation of the fourth joint 145 and a rotation of the fifth joint 155 may be interlocked by a belt, so that the rotation of the fourth link 140 with respect to the third link 130 may cause a rotation of the fifth link 150 with respect to the fourth link 140.

As a result, with this configuration, a line segment connecting the third joint 135 to the fourth joint 145 and a line segment connecting the fifth joint 155 to the RCM may always remain parallel. In addition, a line segment connecting the third joint 135 to the RCM, and a line segment connecting the fourth joint 145 to the fifth joint 155 may also always remain parallel.

The active arm 100 of the surgical robot arm will be described in more detail.

Referring to FIG. 1, the first link 110 may be connected to the fifth setup link 250 by the first joint 115 and is formed to allow yaw rotation around the yaw axis Y1 with respect to the fifth setup link 250. The second link 120 has one end portion fixedly coupled to the first link 110, and another end portion coupled to the third link 130.

The first joint 115 couples the fifth setup link 250 to the first link 110 so that the fifth setup link 250 and the first link 110 are rotatable relative to each other. Specifically, the first joint 115 is formed to allow the first link 110 to rotate around the yaw axis Y1, which is configured to pass through the RCM. Although not shown in the drawings, the first joint 115 may include a motor for rotating the first link 110.

Referring to FIGS. 1 and 4, the yaw axis Y1 may be configured in an oblique direction that is not parallel to the X-axis/Y-axis/Z-axis (based on FIG. 1). In detail, the extension line connecting the third joint 135 to the RCM and the yaw axis Y1 may be positioned to have the same angle with respect to the horizontal plane.

Referring to FIGS. 1 and 4, the first link 110 is coupled to the fifth setup link 250, which is one end portion of the setup arm 200, by the first joint 115 so as to be rotatable around the yaw axis Y1 serving as a central axis of rotation, and thus, the yaw axis Y1, which is an extension line connecting the first joint 115 to the RCM, may extend from the upper side to the lower side when viewed in relation to a patient placed on the bed 500.

In other words, it may be said that heights of points (i.e., the first joint 115) at which the yaw axis Y1 passes through the fifth setup link 250 and the first link 110 are higher than a height of the RCM in the Z-axis direction.

In other words, it may be said that a height of the yaw axis Y1 in the Z-axis direction at a proximal end of the active arm 100 is higher than a height of the yaw axis Y1 in the Z-axis direction at the distal end of the active arm 100.

Here, in terms of the position of the active arm 100 of the surgical robot arm 1, a region connected to the setup arm 200 (specifically the fifth setup link 250) can be defined as the proximal end, and an end portion opposite to the proximal end, such as the RCM formed at the fifth link 150, may be defined as the distal end.

In other words, it may be said that a longitudinal central axis or the central axis of rotation of the first link 110 is configured to be inclined at a predetermined angle with the horizontal plane, so that the central axis of the first link 110 is configured coincide with the yaw axis Y1.

Referring to FIG. 1, the first link 110 may be connected to the fifth setup link 250 by the first joint 115 so as to be rotatable around the yaw axis Y1, and as described above, the fifth setup link 250 may be coupled so as to be rotatable relative to the fourth setup link 240.

The fifth setup link 250 may be connected to the fourth setup link 240 at a predetermined angle. The fourth setup link 240 may be disposed parallel to the horizontal plane, and the angle formed by the fifth setup link 250 and the fourth setup link 240 may be the same as an angle formed by the fifth setup link 250 and the horizontal plane.

For example, when the fifth setup link 250 is positioned at an angle of α° with respect to the fourth setup link 240, the central axis of rotation of the first link 110, which is rotatably coupled to the fifth setup link 250, that is, the yaw axis Y1, is configured to be perpendicular to the fifth setup link 250 and to form an angle of 90-α° with the horizontal plane.

It may be described that the first link 110 is formed to be inclined at a predetermined angle with the horizontal plane, so that the central axis of the first link 110 is formed to coincide with the yaw axis Y1.

As a result, even when the surgical instrument 300 coupled to the active arm 100 is positioned in the horizontal direction parallel to the bed 500, that is, to the horizontal plane on which the patient is placed, the roll axis R, which is formed in the horizontal direction, and the yaw axis Y1, which is positioned to be inclined to a certain degree, maintain a certain degree of angle therebetween, and accordingly, this arrangement prevents the gimbal lock phenomenon that occurs due to the roll axis R of the surgical instrument 300 coinciding with the yaw axis Y1 of the active arm 100.

Referring to FIG. 1, by configuring the RCM to be positioned on the extension line of the yaw axis Y1, the position and orientation of the RCM with respect to the fifth setup link 250 remains constant regardless of the degree of yaw rotation of the first link 110 relative to the fifth setup link 250.

Here, when the first link 110 rotates around the yaw axis Y1 with respect to the fifth setup link 250, the second link 120, the third link 130, the fourth link 140, and the fifth link 150, which are connected to the first link 110, and the surgical instrument 300 connected to the fifth link 150 rotate around the yaw axis Y1 together with the first link 110.

Accordingly, a coordinate system of the surgical instrument 300 and each of the links is not fixed but is relatively continuously changed according to the rotation of the first link 110.

Meanwhile, the second joint 125 connects the second link 120 to the first link 110. In this case, since the second link 120 is fixedly coupled to the first link 110, a relative position of the second link 120 with respect to the first link 110 may be constant.

That is, the second link 120 and the first link 110 may operate together as one body. Here, the second link 120 and the first link 110 are illustrated as being formed as separate members and fixedly coupled to each other, but the concept of the present disclosure is not limited thereto, and it would also be possible that the second link 120 and the first link 110 are integrally formed and function as a yaw drive assembly (no reference number is assigned).

Here, the second link 120 of the first embodiment of the present disclosure may be formed parallel to the yaw axis Y1 of the active arm 100 of the surgical robot arm 1, which is the central axis of rotation of the first link 110. Alternatively, the second link 120 may be formed substantially parallel to the fourth link 140. Alternatively, the second link 120 may also be disposed on or parallel to the extension line of the third joint 135 and the RCM.

Here, the second joint 125 may include a motor, and may be connected to the third joint 135 by a belt, a wire, or the like. Accordingly, a driving force of the second joint 125 can be transmitted to the third joint 135. Alternatively, the second joint 125 may not include a motor, and the third joint 135 may be formed to include a motor.

The third link 130 is axially coupled to the second link 120 so as to be rotatable around the third joint 135 with respect to the second link 120. Here, the third joint 135 may include one or more pulleys.

The fourth link 140 is axially coupled to the third link 130 so as to be rotatable around the fourth joint 145 with respect to the third link 130. Here, the fourth joint 145 may include one or more pulleys.

The fifth link 150 is axially coupled to the fourth link 140 so as to be rotatable around the fifth joint 155 with respect to the fourth link 140. Here, the fifth joint 155 may include one or more pulleys.

The surgical instrument 300 is coupled to the fifth link 150. In this case, at least a portion of the surgical instrument 300 is formed to be rotatable around the roll axis R (i.e., a shaft axis), and is formed to be linearly reciprocally movable along the roll axis R with respect to the fifth link 150. Here, the roll axis R of the surgical instrument 300 is configured to pass through the RCM.

Meanwhile, although not shown in the drawings, an instrument mounting part (not shown) and a guide rail (not shown) may be formed in the fifth link 150, which is a mounting link for the surgical instrument 300, and the instrument mounting part may linearly move along the guide rail, which is formed in a direction of the roll axis R, in a state in which the surgical instrument 300 is mounted on the instrument mounting part. In order to implement such a linear movement, a driving part, such as a linear actuator (not shown), may be provided in the instrument mounting part (not shown). In addition, the surgical instrument 300 may be mounted on the above-described instrument mounting part (not shown) formed on the fifth link 150 of the active arm 100.

Meanwhile, an interface part (not shown) coupled to the surgical instrument 300 and configured to control the movement of the surgical instrument 300 may be further formed in the instrument mounting part (not shown).

In the interface part (not shown), a component for coupling with a driving part of the surgical instrument 300 and a motor for transmitting a driving force from the surgical robot arm to the surgical instrument 300 may be provided. Due to the interface part (not shown), the end tool of the surgical instrument 300 may perform pitch, yaw, and actuation motions. Furthermore, due to the interface part (not shown), the shaft and end tool of the surgical instrument 300 may perform a roll motion around the roll axis R.

Meanwhile, the trocar 400 serving as an insertion path, through which the surgical instrument 300 inserted into a patient's body, may be coupled to the fifth link 150, which is a mounting link to which the surgical instrument 300 is mounted, and the surgical instrument 300 may be inserted into the patient's body through the trocar 400 while the trocar 400 is inserted into the body. In addition, the RCM may be formed at a predetermined position on the above-described trocar 400.

In addition, as described above, the yaw axis Y1, which is the central axis of rotation of the first link 110 rotatably coupled to the fifth setup link 250, may be configured to pass through the RCM.

In addition, the surgical instrument 300 may further include a driving part (not shown). In the driving part (not shown), a component for coupling with the interface part (not shown), a driving wheel operated by being engaged with the motor, and the like may be formed. In addition, a coupling member and a drive transmission member may be correspondingly formed on the interface part (not shown) and the driving part (not shown), respectively, which allows the surgical instrument 300 to operate by receiving a driving force from the surgical robot arm 1, specifically the active arm 100, while mounted on the fifth link 150.

Here, the third joint 135, the fourth joint 145, the fifth joint 155, and the RCM may be four vertices of a parallelogram. That is, the third joint 135, the fourth joint 145, the fifth joint 155, and the RCM may form a single parallelogram.

In detail, when three vertices, which are the third joint 135, the fourth joint 145, and the fifth joint 155, are established, the position of the RCM in the parallelogram including these three vertices is automatically defined.

In addition, when the third link 130 rotates around the third joint 135 while the position of the third joint 135 is fixed, due to the RCM mechanism involving links/belts, which will be described later, the third link 130 and the fifth link 150 rotate while maintaining the parallel state in any operational state of the surgical robot arm 1, and the extension line connecting the third joint 135 to the RCM and the fourth link 140 also rotate while maintaining the parallel state in any operational state of the surgical robot arm 1. Accordingly, the RCM may remain constant in position regardless of the rotation angle of the third link 130 with respect to the second link 120. Referring to FIG. 4, the parallel state between the third link 130 and the fifth link 150 indicates that the third link and the line segment connecting the fifth joint 155 to the RCM remain parallel.

In this structure, once the surgical robot arm 1 is set up, the RCM always remains in its position. In addition, whenever each of the links rotates around the RCM, regardless of its position, the links maintain the parallelogram.

That is, during the set-up process, in a state in which the position of the setup arm 200 is determined, the positions of the body 201 and the plurality of setup links 210, 220, 230, 240, and 250, which are sequentially connected to the body 201, are fixed, and the first link 110 coupled to the setup link, specifically the fifth setup link 250, is fixed, the position of the RCM does not change regardless of the positions of the third link 130 to the fifth link 150, and, the third joint 135, the fourth joint 145, the fifth joint 155, and the RCM maintain a parallelogram.

In order to maintain the RCM as described above, the fourth joint 145 and the fifth joint 155 are connected to each other to be rotatable around the third joint 135. Various power transmission devices, such as belts, wires, and links, may be used to connect the third joint 135, the fourth joint 145, and the fifth joint 155 to each other.

For example, a rotation of the third joint 135 and a rotation of the fourth joint 145 may be interlocked by a belt, so that a rotation of the third link 130 with respect to the second link 120 may cause a rotation of the fourth link 140 with respect to the third link 130. At the same time, the rotation of the fourth joint 145 and a rotation of the fifth joint 155 may be interlocked by a belt, so that the rotation of the fourth link 140 with respect to the third link 130 may cause a rotation of the fifth link 150 with respect to the fourth link 140.

As a result, with this configuration, a line segment connecting the third joint 135 to the fourth joint 145 and a line segment connecting the fifth joint 155 to the RCM may always remain parallel.

In addition, a line segment connecting the third joint 135 to the RCM, and a line segment connecting the fourth joint 145 to the fifth joint 155 may also always remain parallel.

Although not shown in the drawings, in an optional embodiment, it is also possible to have a configuration in which the first link 110 and the third link 130 are connected directly by the second joint 125, without having the second link 120 and the third joint 135.

Meanwhile, in the first embodiment of the present disclosure, some of the links, particularly the second link 120, the third link 130, the fourth link 140, and the fifth link 150, may be disposed on different planes so as not to intersect each other.

That is, along a central axis of rotation of the third joint 135 through which the second link 120 and the third link 130 are coupled to each other, the second link 120 and the third link 130 may be disposed on different planes perpendicular to the central axis of rotation.

In addition, the third link 130 and the fourth link 140 may be disposed on different planes perpendicular to a central axis of rotation of the fourth joint 145 through which the third link 130 and the fourth link 140 are coupled to each other.

However, the present disclosure is not limited thereto, and various modifications are possible, such as the second link 120, the third link 130, and the fourth link 140 being disposed on the same plane perpendicular to the central axis of rotation within the technical concept of being disposed side by side without overlapping each other.

Meanwhile, in FIG. 1, the fourth link 140 and the fifth link 150 are disposed on the same plane perpendicular to a central axis of rotation of the fifth joint 155 through which the fourth link 140 and the fifth link 150 are coupled to each other, but the present disclosure is not limited thereto, and various modifications are possible, such as arranging the fourth link 140 and the fifth link 150 on different planes.

Accordingly, in the active arm 100 of the surgical robot arm 1 according to the first embodiment of the present disclosure, each link is formed so that when one link rotates with respect to another link, no collisions occur and no interference is caused by the rotation, thereby expanding the driving range of each link.

Figure 19:
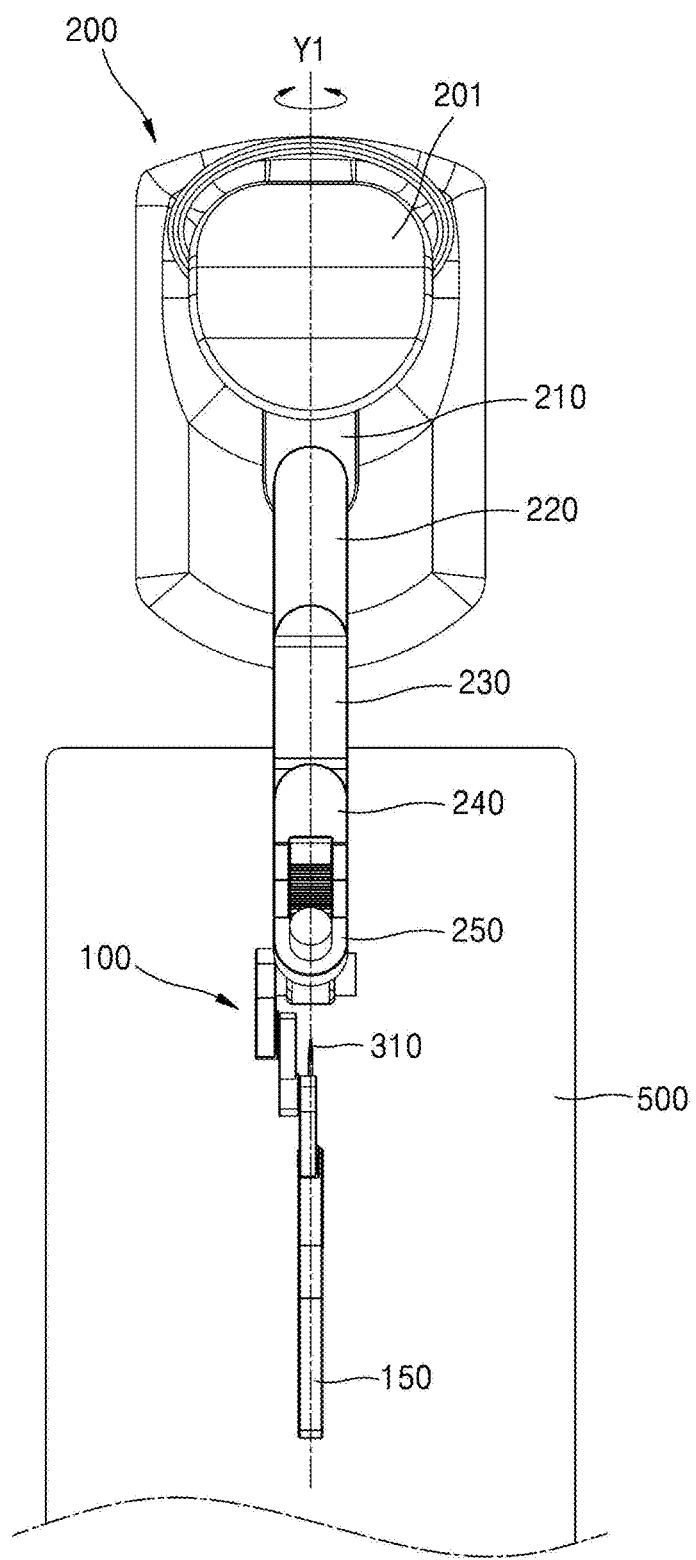
FIG. 19 is a plan view illustrating the surgical robot arm of FIG. 17.

In detail, referring to FIG. 19, which is a plan view of the surgical robot arm 1 according to an embodiment of the present disclosure, when viewed from an XY plane, at least some of the second link 120, the third link 130, and the fourth link 140 are formed to be offset by a certain degree in a direction of the rotation axes thereof (i.e., in a Y-axis direction).

In other words, in the Y-axis direction, the third link 130 may be disposed on one side of the second link 120, and the fourth link 140 may be disposed on one side of the third link 130.

Figure 18:
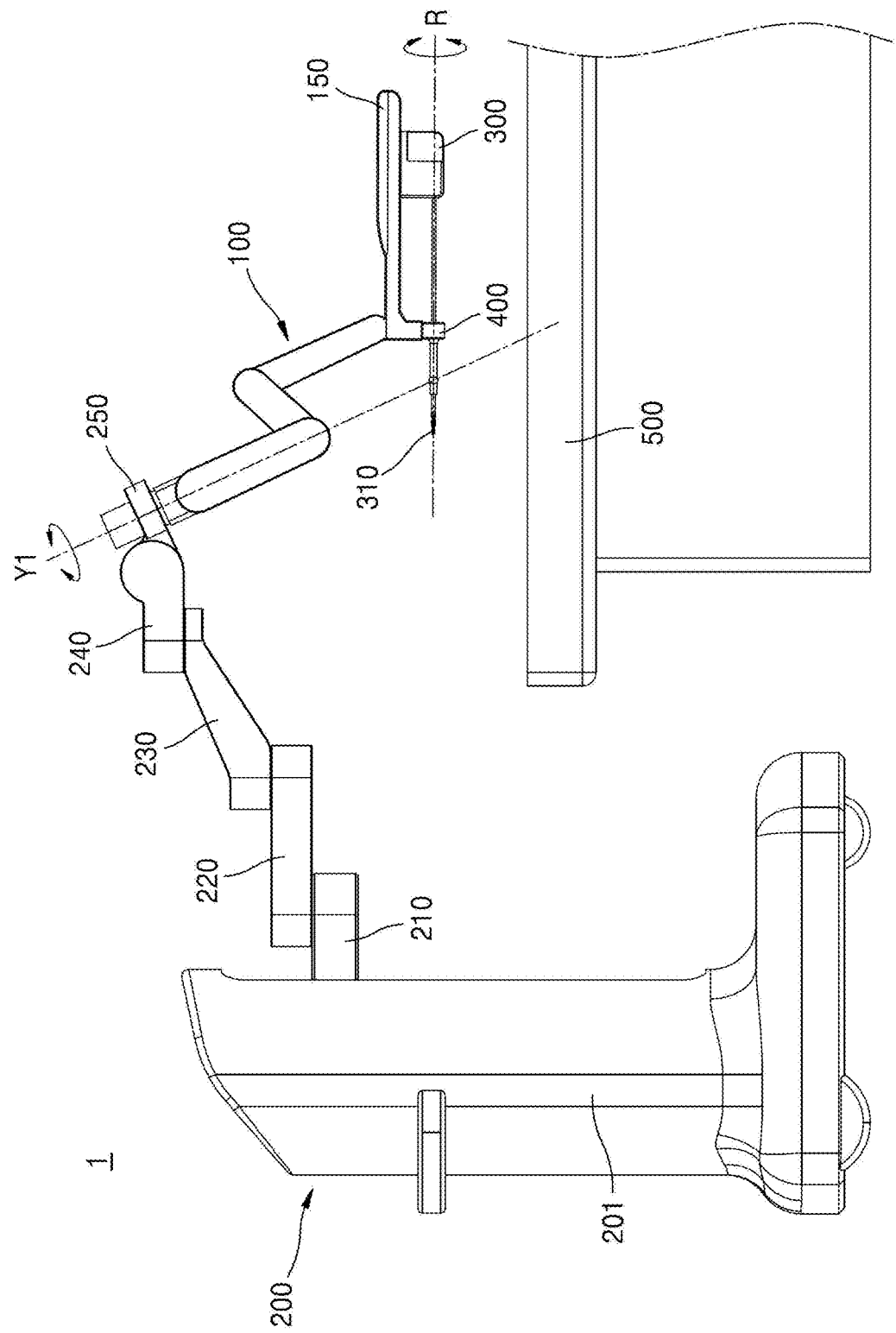
FIG. 18 is a side view illustrating the surgical robot arm of FIG. 17.

Referring to FIG. 18, the yaw axis Y1, which is the central axis of rotation of the first link 110 rotatably coupled to the fifth setup link 250, and the roll axis R of the surgical instrument 300 may intersect at the RCM.

Within this technical concept, the second link 120, the third link 130, the fourth link 140, and the fifth link 150 may be connected to each other on one side of each link in the direction of the rotational axis (i.e., the Y-axis direction), thereby removing the restriction on a rotation range of the third link 130, the fourth link 140, and the fifth link 150, and allowing each of these links to rotate freely.

Meanwhile, from another perspective, it may be said that since the links are formed in such a manner that no one link interferes with the rotation of another link, at least a portion of each of the links may overlap each other in the direction of the yaw axis Y1. That is, in a state in which the active arm 100 of the surgical robot arm 1 is folded to a certain degree as shown in FIG. 19, the second link 120 and the third link 130 may be disposed to overlap to a certain degree in the direction of the yaw axis Y1, and the third link 130 and the fourth link 140 may be disposed to overlap to a certain degree in the direction of the yaw axis Y1.

Referring to FIG. 19, in the active arm 100 according to the first embodiment of the present disclosure, the fourth link 140 and the fifth link 150 are disposed side by side on the same plane and are rotatably coupled to each other. but the present disclosure is not limited thereto, and various modifications are possible, such as arranging the fourth link 140 and the fifth link 150 side by side on different planes along their respective central axes of rotation.

Meanwhile, the fifth link 150 according to the first embodiment of the present disclosure has a first surface (an upper surface based on FIG. 1) rotatably coupled to the fourth link 140, and a second surface (a lower surface based on FIG. 1), which is opposite to the first surface and to which the surgical instrument 300 may be coupled.

Hereinafter, operations of the active arm of the surgical robot arm according to the first embodiment of the present disclosure will be described.

As shown in FIGS. 4 to 6, when the motor (not shown) is driven, the active arm 100, specifically the first link 110, which is coupled to the setup arm 200, specifically, the fifth setup link 250, rotates around the yaw axis Y1 with respect to the fifth setup link 250. At this time, since the yaw axis Y1 passes through the RCM, the RCM remains constant regardless of the angle at which the first link 110 rotates with respect to the fifth setup link 250.

Specifically, during the setup stage of the surgical robot arm 1 before surgery, the fifth setup link 250 is rotated by a predetermined angle (e.g., 20°) relative to the horizontal plane with respect to the fourth setup link 240. In addition, the active arm 100, specifically, the first link 110, may be rotatably coupled to the fifth setup link 250, and the central axis of rotation of the first link 110 may be set as the yaw axis Y1 of the surgical robot arm 1.

The yaw axis Y1 may be positioned at a predetermined angle, specifically, perpendicular to the fifth setup link 250, and accordingly, may be positioned at a predetermined angle (e.g., 70°) with respect to the horizontal plane. The RCM may be positioned on the yaw axis Y1, the second link 120, which is coupled to the first link 110, may be disposed parallel to the yaw axis Y1, and the extension line connecting the RCM to the third joint 135, through which the second link 120 and the third link 130 are axially coupled, may be positioned parallel to the yaw axis Y1.

That is, the extension line connecting the third joint 135 to the RCM may be positioned parallel to the yaw axis Y1, and the yaw axis Y1 is positioned to be inclined at a predetermined angle with the roll axis R of the surgical instrument 300 that is connected to the fifth link, thereby preventing a gimbal lock phenomenon that may occur when the roll axis R and the yaw axis Y1 are positioned parallel or nearly parallel to each other when the surgical instrument 300 is disposed parallel to the horizontal plane.

Referring to FIGS. 4, 5, and 6, as the plurality of setup links are axially coupled to each other and arranged at progressively higher positions as the distance from the body 201 in the Z-axis direction increases, the yaw axis Y1 of the surgical robot arm 1 can be configured to extend from the upper side to the lower side and be inclined at a predetermined angle relative to the horizontal plane, and when the surgical instrument 300 is disposed horizontally, the yaw axis Y1 can be configured to be inclined at a predetermined angle with respect to the roll axis R of the surgical instrument 300, thereby effectively preventing the gimbal lock phenomenon that may occur when the angle between the yaw axis Y1 and the roll axis R becomes small or when the yaw axis Y1 and the roll axis R are disposed parallel to each other.

FIG. 7 is a side view illustrating an RCM motion (the second pitch motion) of the surgical robot arm of FIG. 4 around the pitch axis P. FIG. 8 is a perspective view illustrating the surgical robot arm of FIG. 7.

Referring to FIGS. 7 and 8, it is illustrated that the active arm 100 has rotated by a certain degree around the pitch axis P from the state of the first pitch motion illustrated in FIG. 6.

That is, with the RCM position fixed and the angle of the fifth setup link 250 relative to the fourth setup link 240 unchanged, the surgical robot arm 1 can perform a pitch motion by rotating the third link 130, the fourth link 140, and the fifth link 150.

At this time, since the position of the second link 120 is fixed and the positions of the third joint 135 and the RCM are fixed, the third link 130, the fourth link 140, and the fifth link 150 can move while the third joint 135, the fourth joint 145, the fifth joint 155, and the RCM form a parallelogram.

Referring to FIG. 7 and FIG. 8, the surgical instrument 300 may enter from the upper side to the lower side in the Z-axis direction.

Referring to FIG. 7, although the yaw axis Y1 remains unchanged, and the angle between the yaw axis Y1 and the roll axis R of the surgical instrument 300 is relatively reduced compared to FIGS. 4 to 6, the yaw axis Y1 and the roll axis R can still be configured to be inclined at a predetermined angle, which can prevent a gimbal lock phenomenon that may occur when the angle between the yaw axis Y1 and the roll axis R is small, or when the yaw axis Y1 and the roll axis R are positioned parallel to each other.

FIG. 9 is a side view illustrating an RCM motion (the third pitch motion) of the surgical robot arm of FIG. 4 around the pitch axis P. FIG. 10 is a perspective view illustrating the surgical robot arm of FIG. 9.

Referring to FIG. 9, it is illustrated that the active arm 100 has rotated by a certain degree around the pitch axis P from the state of the first pitch motion illustrated in FIG. 6.

That is, FIG. 9 illustrates a state in which the active arm 100 has been rotated around the pitch axis P in the opposite direction compared to FIG. 7, with the position of the RCM fixed, and the angle between the fifth setup link 250 and the fourth setup link 240 unchanged, and a state in which the pitch motion of the surgical robot arm 1 is performed by rotating the third link 130, the fourth link 140, and the fifth link 150.

At this time, since the position of the second link 120 is fixed and the positions of the third joint 135 and the RCM are fixed, the third link 130, the fourth link 140, and the fifth link 150 can move while the third joint 135, the fourth joint 145, the fifth joint 155, and the RCM form a parallelogram.

Referring to FIG. 9, the yaw axis Y1 remains unchanged and the active arm 100 has been rotated around the pitch axis P in the opposite direction compared to FIG. 7, so that the angle between the yaw axis Y1 and the roll axis R of the surgical instrument 300 is relatively increased, allowing the surgical instrument 300 to enter from the lower side to the upper side in the Z-axis direction.

In addition, the yaw axis Y1 and the roll axis R can be configured to be inclined at a predetermined angle, thereby preventing a gimbal lock phenomenon that may occur when the angle between the yaw axis Y1 and the roll axis R is small, or when the yaw axis Y1 and the roll axis R are positioned parallel to each other.

FIG. 11 is a perspective view illustrating an RCM motion (the first yaw motion) of the surgical robot arm according to the first embodiment of the present disclosure around the yaw axis Y1. FIG. 12 is a plan view illustrating the surgical robot arm of FIG. 11.

As described in FIG. 5 and FIG. 6, the yaw axis Y1 of the surgical robot arm 1 is configured in an upper-to-lower direction, and the yaw axis Y1 is configured to be inclined at a predetermined angle with the roll axis R of the surgical instrument 300 that is disposed parallel to the horizontal plane.

As described above, the yaw axis Y1 of the surgical robot arm 1 may be configured to extend from the upper side to the lower side and to be inclined at a predetermined angle relative to the horizontal plane, and thus when the surgical instrument 300 is disposed horizontally, the yaw axis Y1 can be configured to be inclined at a predetermined angle with respect to the roll axis R of the surgical instrument 300, thereby preventing a gimbal lock phenomenon that may occur when the angle between the yaw axis Y1 and the roll axis R is small, or when the yaw axis Y1 and the roll axis R are positioned parallel to each other.

FIG. 13 is a perspective view illustrating an RCM motion (the second yaw motion) of the surgical robot arm according to the first embodiment of the present disclosure around the yaw axis Y1. FIG. 14 is a plan view illustrating the surgical robot arm of FIG. 13. FIG. 15 is a perspective view illustrating an RCM motion (the third yaw motion) of the surgical robot arm according to the first embodiment of the present disclosure around the yaw axis Y1. FIG. 16 is a plan view illustrating the surgical robot arm of FIG. 15.

Referring to FIG. 13, it is illustrated that the active arm 100 has rotated by a certain degree around the yaw axis Y1 from the state of the first yaw motion illustrated in FIG. 11.

That is, with the RCM position fixed and the angle of the fifth setup link 250 relative to the fourth setup link 240 unchanged, the surgical robot arm 1 may perform a yaw motion by rotating the first link 110 coupled to the fifth setup link 250.

At this time, since the position of the second link 120 is fixed and the positions of the third joint 135 and the RCM are fixed, the state in which the third joint 135, the fourth joint 145, the fifth joint 155, and the RCM form a parallelogram can be maintained.

Referring to FIGS. 13 and 14, when the first joint 115 rotates in a counterclockwise direction (based on FIG. 13) around the yaw axis Y1, the first link 110 rotates in the counterclockwise direction around the yaw axis Y1, which serves as the central axis of rotation, with respect to the fifth setup link 250, and the yaw axis Y1 remains constant, so that the active arm 100 can rotate while the RCM positioned on the yaw axis Y1 also remains constant.

Referring to FIG. 14, compared to FIG. 12, the entry path can be changed to allow the surgical instrument 300 to enter from a relatively left side (based on FIG. 14).

Referring to FIG. 15, it is illustrated that the active arm 100 has rotated by a certain degree around the yaw axis Y1 from the state of the first yaw motion illustrated in FIG. 11. Here, the active arm 100 has been rotated in a direction opposite to the direction of rotation during the second yaw motion shown in FIG. 13.

That is, with the RCM position fixed and the angle of the fifth setup link 250 relative to the fourth setup link 240 unchanged, the surgical robot arm 1 may perform a yaw motion by rotating the first link 110 coupled to the fifth setup link 250.

At this time, since the position of the second link 120 is fixed and the positions of the third joint 135 and the RCM are fixed, the state in which the third joint 135, the fourth joint 145, the fifth joint 155, and the RCM form a parallelogram can be maintained.

Referring to FIGS. 15 and 16, when the first joint 115 rotates in a clockwise direction (based on FIG. 13) around the yaw axis Y1, the first link 110 rotates in the clockwise direction around the yaw axis Y1, which serves as the central axis of rotation, with respect to the fifth setup link 250, and the yaw axis Y1 remains constant, so that the active arm 100 can rotate while the RCM positioned on the yaw axis Y1 also remains constant.

Referring to FIG. 15, compared to FIG. 12, the entry path can be changed to allow the surgical instrument 300 to enter from a relatively left side (based on FIG. 14).

Referring to FIGS. 13 and 15, the yaw axis Y1 remains unchanged, and the yaw axis Y1 and the roll axis R may be configured to be inclined at a predetermined angle, thereby preventing a gimbal lock phenomenon that may occur when the angle between the yaw axis Y1 and the roll axis R is small, or when the yaw axis Y1 and the roll axis R are positioned parallel to each other.

Figure 17:
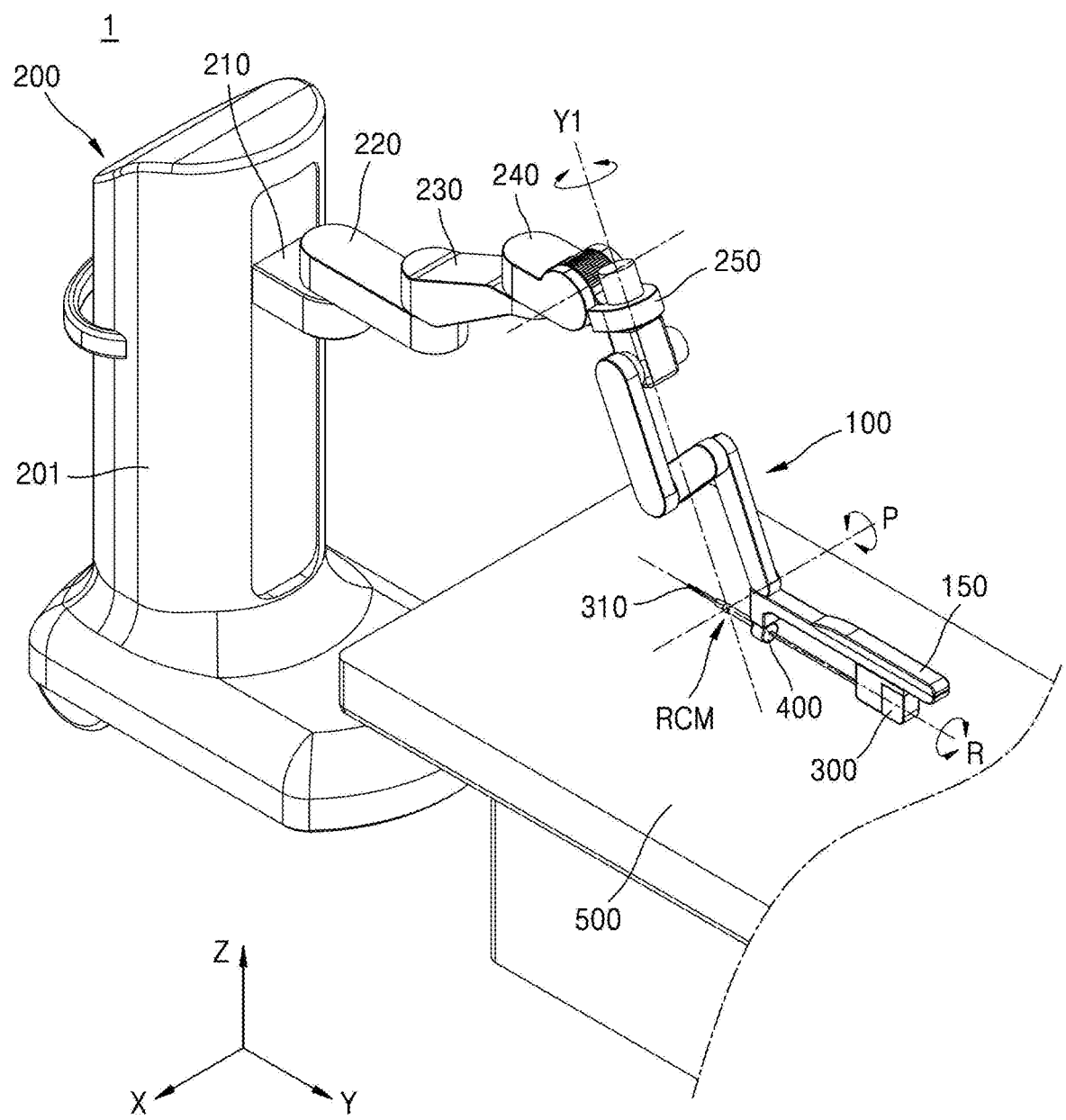
FIG. 17 is a perspective view illustrating a state in which a surgical instrument is disposed on the surgical robot arm to face a body.

FIG. 17 is a perspective view illustrating a state in which the surgical instrument is disposed on the surgical robot arm to face the body. FIG. 18 is a side view illustrating the surgical robot arm of FIG. 17. FIG. 19 is a plan view illustrating the surgical robot arm of FIG. 17.

Referring to FIG. 17, compared to FIG. 4 in which an end tool 310 of the surgical instrument 300 is disposed in a direction away from the body 201 of the setup arm 200, FIG. 17 illustrates a state in which the end tool 310 of the surgical instrument 300 is disposed in a direction facing the body 201.

As shown in FIG. 17, when the motor (not shown) is driven, the active arm 100, specifically the first link 110, which is coupled to the setup arm 200, specifically, the fifth setup link 250, rotates around the yaw axis Y1 with respect to the fifth setup link 250.

The first link 110 may be rotated 180° around the yaw axis Y1 compared to FIG. 6. At this time, since the yaw axis Y1 passes through the RCM, the RCM remains constant even though the first link 110 has rotated with respect to the fifth setup link 250.

FIG. 17 is a view illustrating, similar to FIG. 6, a state in which the fifth link 150 of the active arm 100 of the surgical robot arm 1 and the surgical instrument 300 coupled thereto are disposed parallel to the horizontal plane (or the XY plane).

Referring to FIG. 17, the fifth setup link 250 is rotatable around a central axis of rotation, which is parallel to the X-axis, with respect to the fourth setup link 240, and may rotate with respect to the fourth setup link 240 to make a predetermined angle with the horizontal plane.

Referring to FIG. 17, similar to FIG. 6, the fifth setup link 250 is rotated by a predetermined angle (e.g., 20°) relative to the horizontal plane with respect to the fourth setup link 240. In addition, the active arm 100, specifically, the first link 110, may be rotatably coupled to the fifth setup link 250, and the central axis of rotation of the first link 110 may be set as the yaw axis Y1 of the surgical robot arm 1.

The yaw axis Y1 may be positioned at a predetermined angle of 90° with respect to the fifth setup link 250, and accordingly, may be positioned at a predetermined angle (e.g., 70°) with respect to the horizontal plane. The RCM may be positioned on the yaw axis Y1, the second link 120, which is coupled to the first link 110, may be disposed parallel to the yaw axis Y1, and the extension line connecting the RCM to the third joint 135, through which the second link 120 and the third link 130 are axially coupled, may be positioned parallel to the yaw axis Y1.

Compared to FIG. 6, in which the fifth link 150 to which the surgical instrument 300 is coupled is disposed on the same side as the setup arm 200, specifically the body 201, with respect to the RCM, in FIG. 17, the fifth link 150 to which the surgical instrument 300 is coupled is disposed on the opposite side of the setup arm 200, specifically the body 201, with respect to the RCM. Accordingly, the end tool 310 of the surgical instrument 300 coupled to the fifth link 150 may be disposed in a direction facing the body 201.

Accordingly, in performing surgery on a patient, when it is necessary to move or enter the surgical instrument 300 in a different direction after positioning the surgical robot arm 1 on one side of the bed 500, only the active arm 100 connected to the setup arm 200 can be driven to move the fifth link 150 and the surgical instrument 300 connected to the fifth link 150 to the opposite side of the consistently maintained RCM, without needing to move the entire body 201, this eliminates the time required to move surgical equipment, such as the surgical robot arm 1, thereby reducing the overall surgery time.

In addition, the extension line connecting the third joint 135 to the RCM may be positioned parallel to the yaw axis Y1, and the yaw axis Y1 is positioned to be inclined at a predetermined angle with the roll axis R of the surgical instrument 300 that is connected to the fifth link 150, thereby preventing a gimbal lock phenomenon that may occur when the roll axis R and the yaw axis Y1 are positioned parallel or nearly parallel to each other when the surgical instrument 300 is disposed parallel to the horizontal plane.

Referring to FIGS. 17. to 19, the yaw axis Y1 of the surgical robot arm 1 may be configured to extend from the upper side to the lower side and to be inclined at a predetermined angle relative to the horizontal plane, and thus, when the surgical instrument 300 is disposed horizontally, the yaw axis Y1 can be configured to be inclined at a predetermined angle with respect to the roll axis R of the surgical instrument 300, thereby preventing a gimbal lock phenomenon that may occur when the angle between the yaw axis Y1 and the roll axis R is small, or when the yaw axis Y1 and the roll axis R are positioned parallel to each other.

FIGS. 42 to 50 are views illustrating an RCM motion of the surgical robot arm according to the first embodiment of the present disclosure around the pitch axis P at a predetermined angle.

Figure 42:
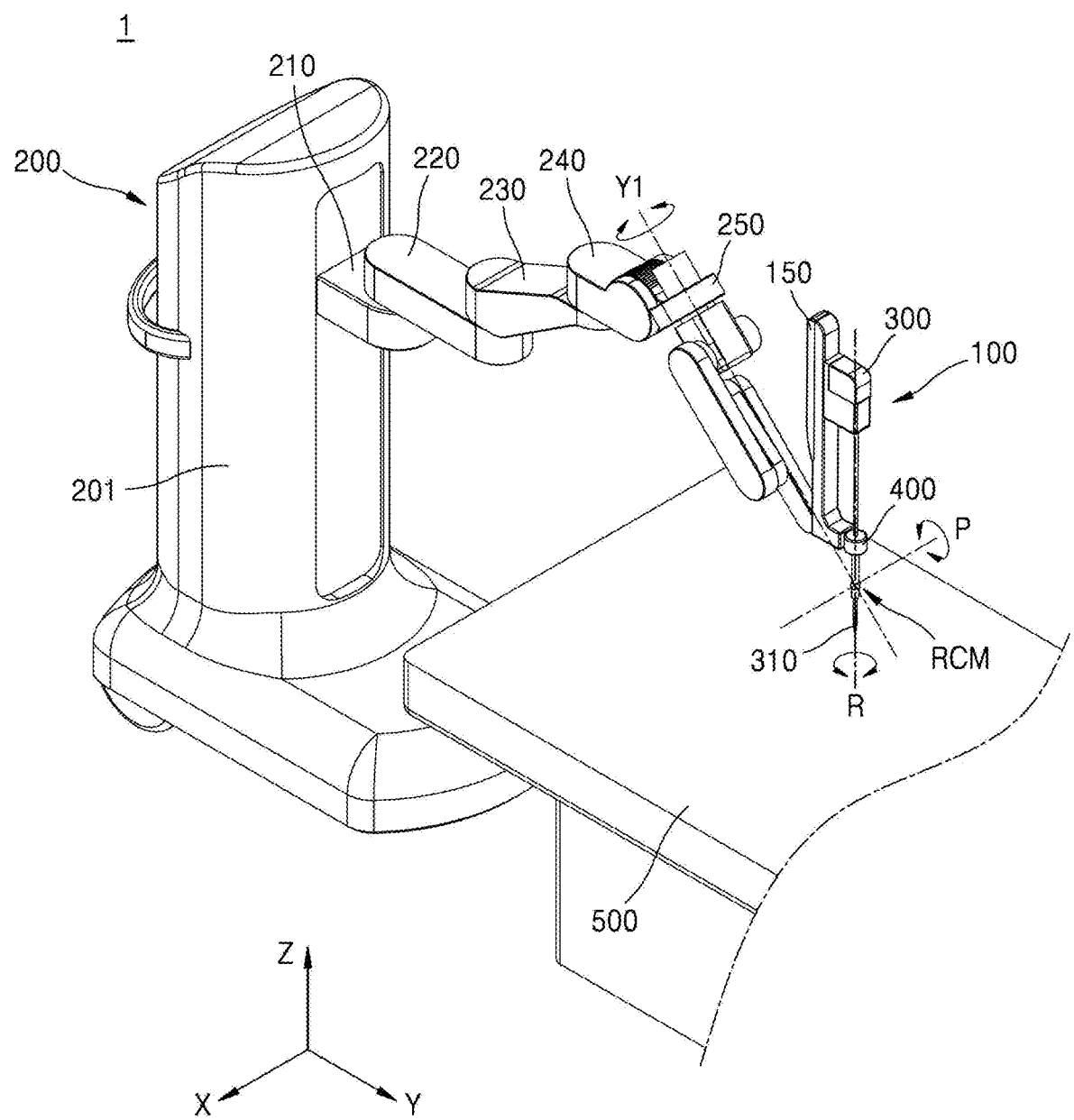
FIGS. 42 to 50 are views illustrating an RCM motion of the surgical robot arm according to the first embodiment of the present disclosure around the pitch axis at a predetermined angle.

Referring to FIG. 42, unlike FIG. 4, which illustrates a state in which the fifth setup link 250 forms a predetermined angle of 20° with respect to the fourth setup link 240, FIG. 42 illustrates a state in which the fifth setup link 250 forms an angle of 45° with respect to the fourth setup link 240.

That is, the angle formed by the fifth setup link 250 with the horizontal plane is 45°, and the yaw axis Y1, which is the central axis of rotation of the first link 110 of the active arm 100 rotatably coupled to the fifth setup link 250, forms an angle of 45° with the horizontal plane.

Referring to FIG. 42, in the active arm 100, as the first link 110 and the second link 120 are fixed in position and the third link 130, the fourth link 140, and the fifth link 150 rotate, the RCM can be maintained due to the RCM mechanism described above.

Referring to FIG. 42, the second link 120, the third link 130, and the fourth link 140 may be disposed to partially overlap each other, and the third joint 135, the fourth joint 145, and the fifth joint 155 may be disposed on the yaw axis Y1.

Figure 43:
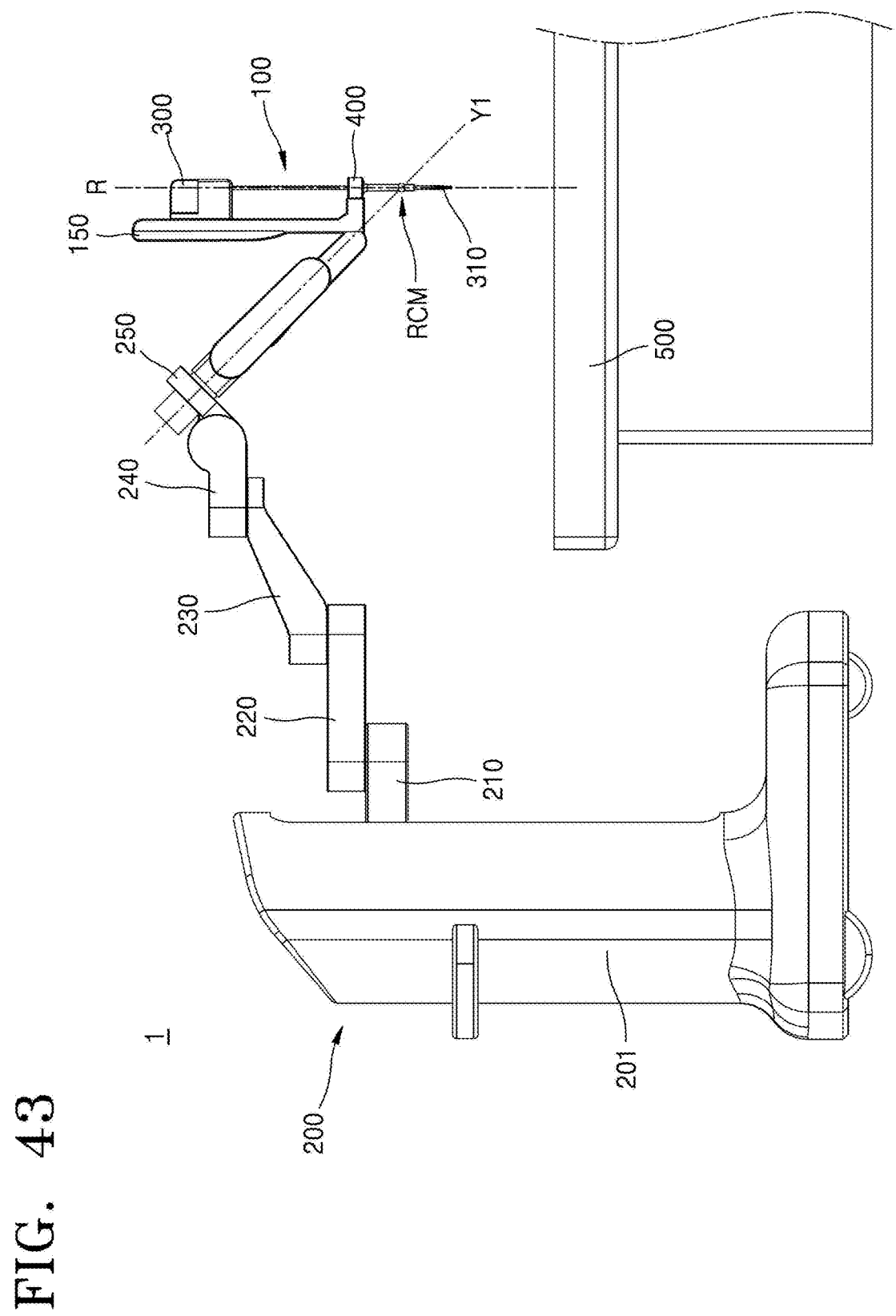
Figure 44:
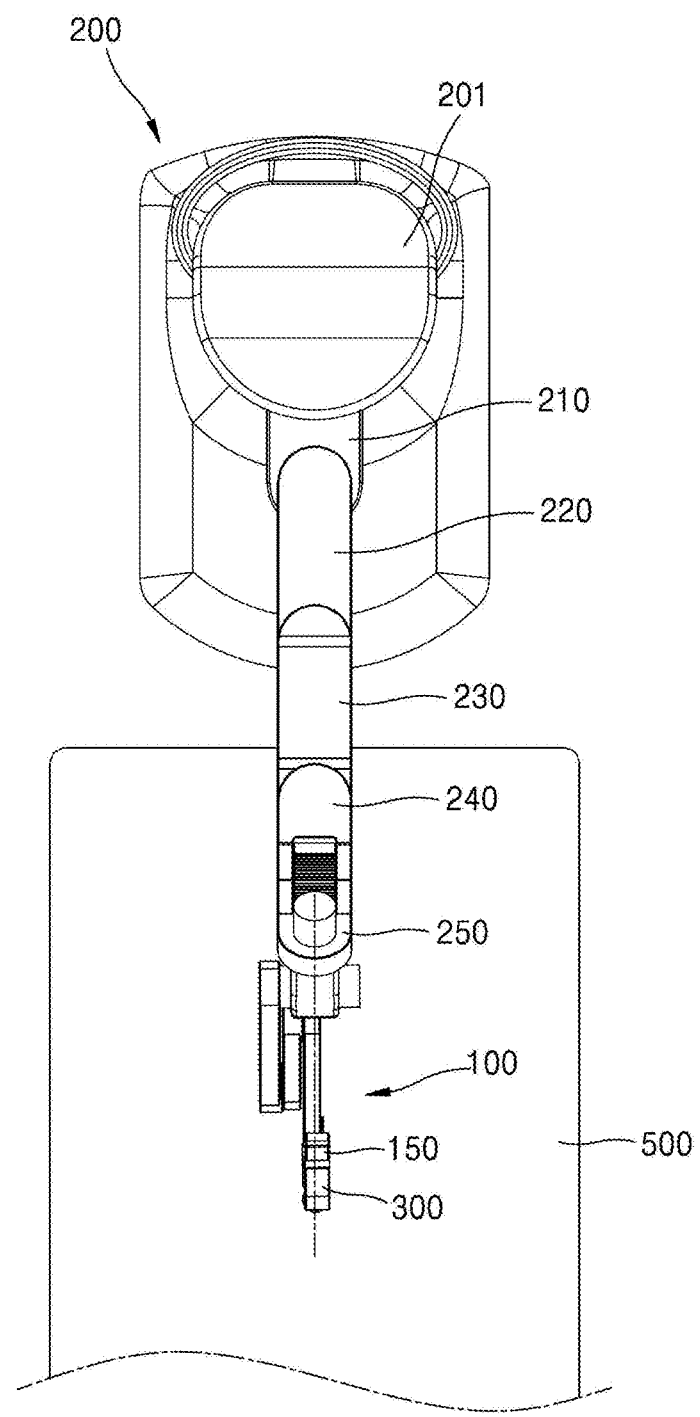

Referring to FIGS. 42 to 44, the fifth link 150 may be rotated with respect to the fourth link 140 so that a longitudinal central axis of the fifth link 150 may be configured parallel to the Z-axis. That is, the roll axis R of the surgical instrument 300 may be perpendicular to the bed 500 or the horizontal plane.

At this time, the yaw axis Y1 of the surgical robot arm 1 may be configured to extend from the upper side to the lower side and to be inclined at a predetermined angle of 45° with respect to the horizontal plane, and thus, when the surgical instrument 300 is disposed vertically, the yaw axis Y1 can be configured to be inclined with respect to the roll axis R of the surgical instrument 300, thereby preventing a gimbal lock phenomenon that may occur when the angle between the yaw axis Y1 and the roll axis R is small, or when the yaw axis Y1 and the roll axis R are positioned parallel to each other.

Figure 45:
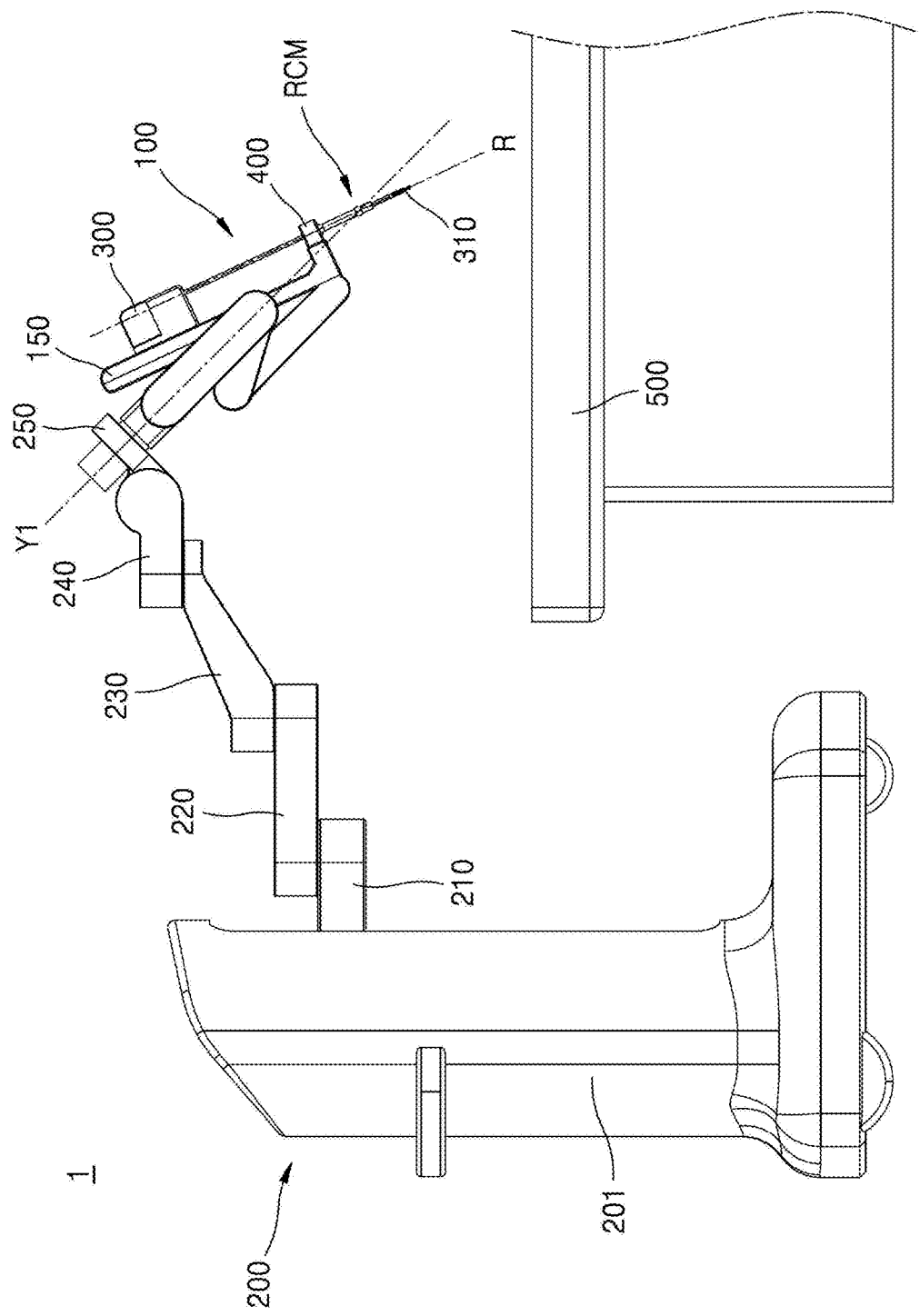
Figure 46:
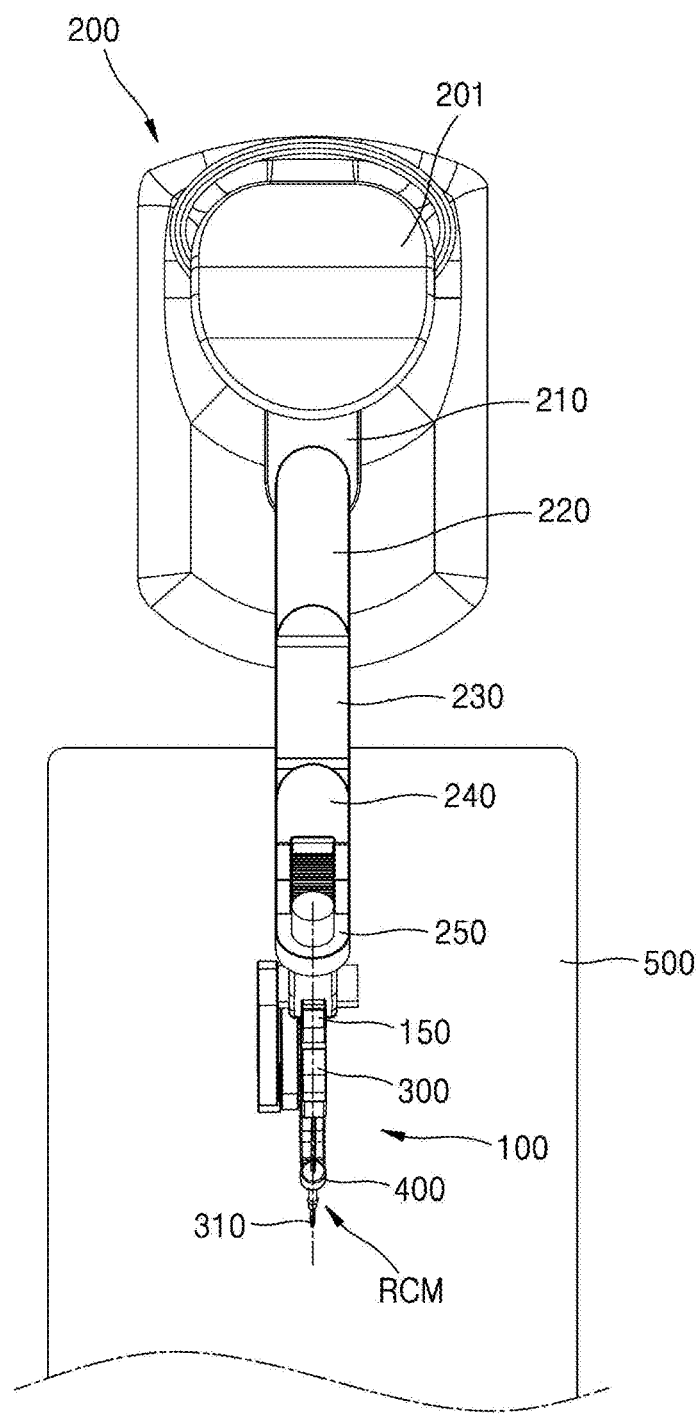

Referring to FIGS. 45 and 46, as the third link 130 in FIG. 43 receives a driving force from a motor (not shown) positioned in the second link 120 and rotates in a first direction (in a counterclockwise direction based on FIG. 45), the fourth link 140 and the fifth link 150 rotate. At this time, the third joint 135, the fourth joint 145, and the fifth joint 155 may form a parallelogram due to the RCM mechanism, and the active arm 100 of the surgical robot arm 1 may perform a pitch motion while the RCM is maintained.

That is, the pitch motion may be performed around the pitch axis P in a direction in which the angle between the roll axis R and the yaw axis Y1 decreases. Even in this case, the effect of preventing the gimbal lock phenomenon can be achieved because the yaw axis Y1 and the roll axis R of the surgical robot arm 1 are still positioned to be inclined.

Figure 47:
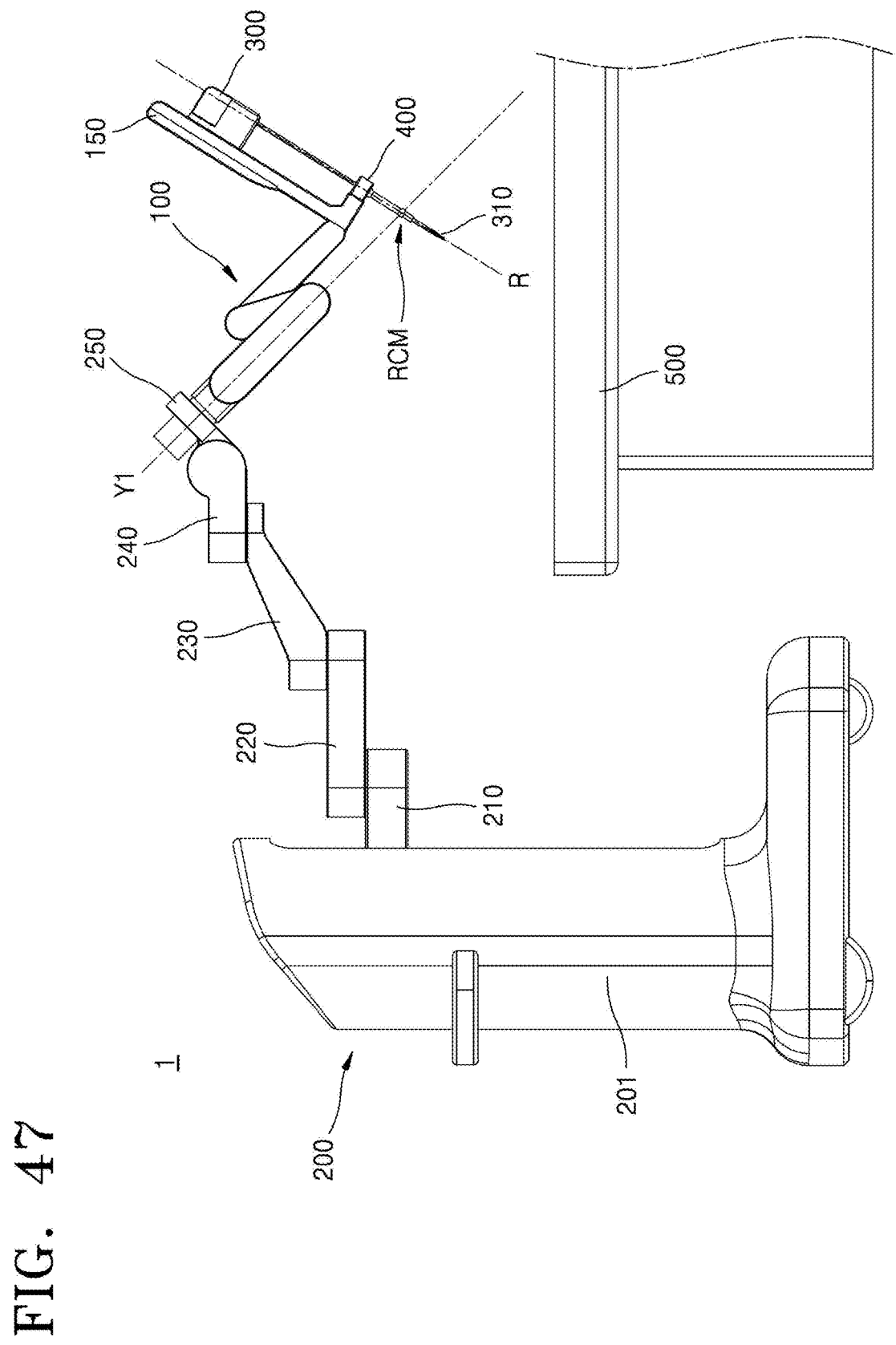
Figure 48:
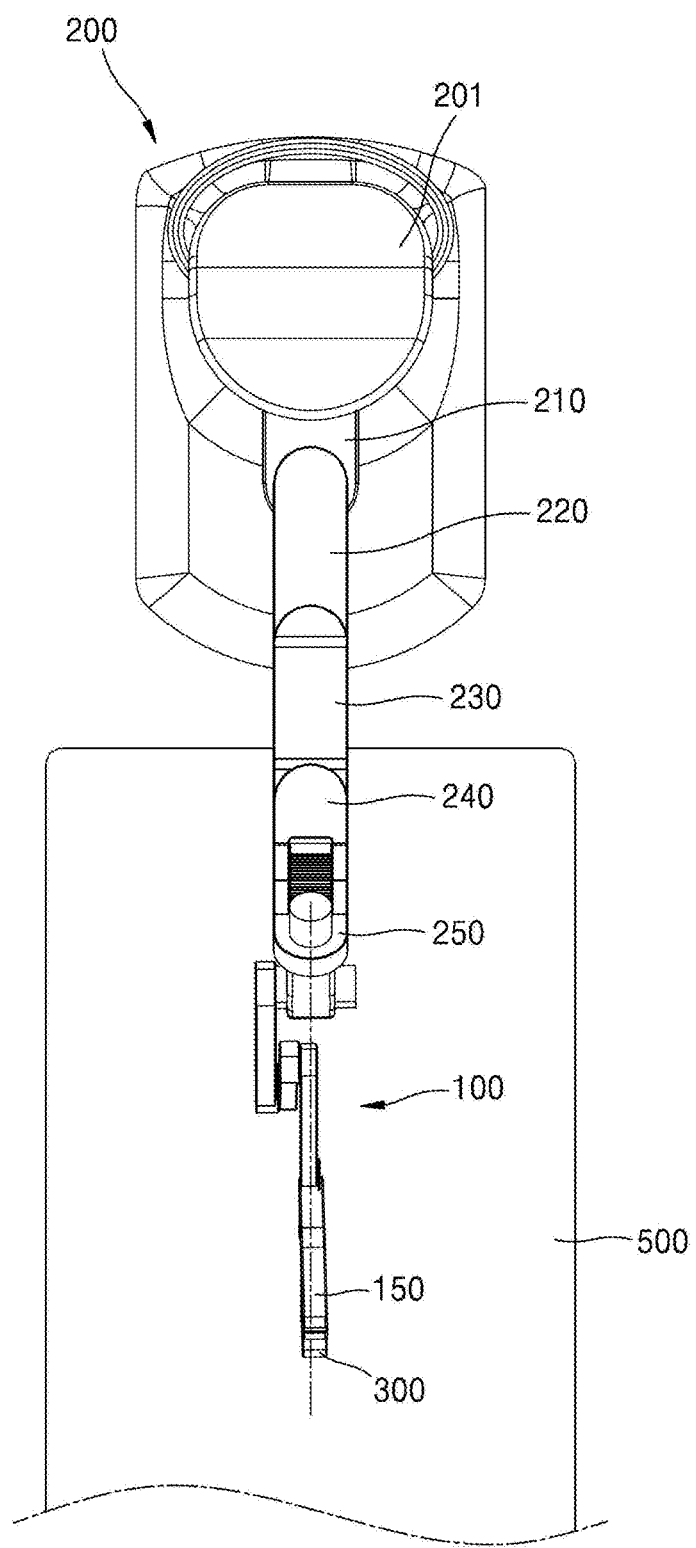

Referring to FIGS. 47 and 48, as the third link 130 in FIG. 43 receives a driving force from the motor (not shown) positioned in the second link 120 and rotates in a second direction (the clockwise direction based on FIG. 45), the fourth link 140 and the fifth link 150 rotate. At this time, the third joint 135, the fourth joint 145, and the fifth joint 155 may form a parallelogram due to the RCM mechanism, and the active arm 100 of the surgical robot arm 1 may perform a pitch motion in the opposite direction as shown in FIG. 45 while the RCM is maintained.

That is, the pitch motion may be performed around the pitch axis P in a direction in which the angle between the roll axis R and the yaw axis Y1 increases. Even in this case, the effect of preventing the gimbal lock phenomenon can be achieved because the yaw axis Y1 and the roll axis R of the surgical robot arm 1 are still positioned to be inclined.

Figure 49:
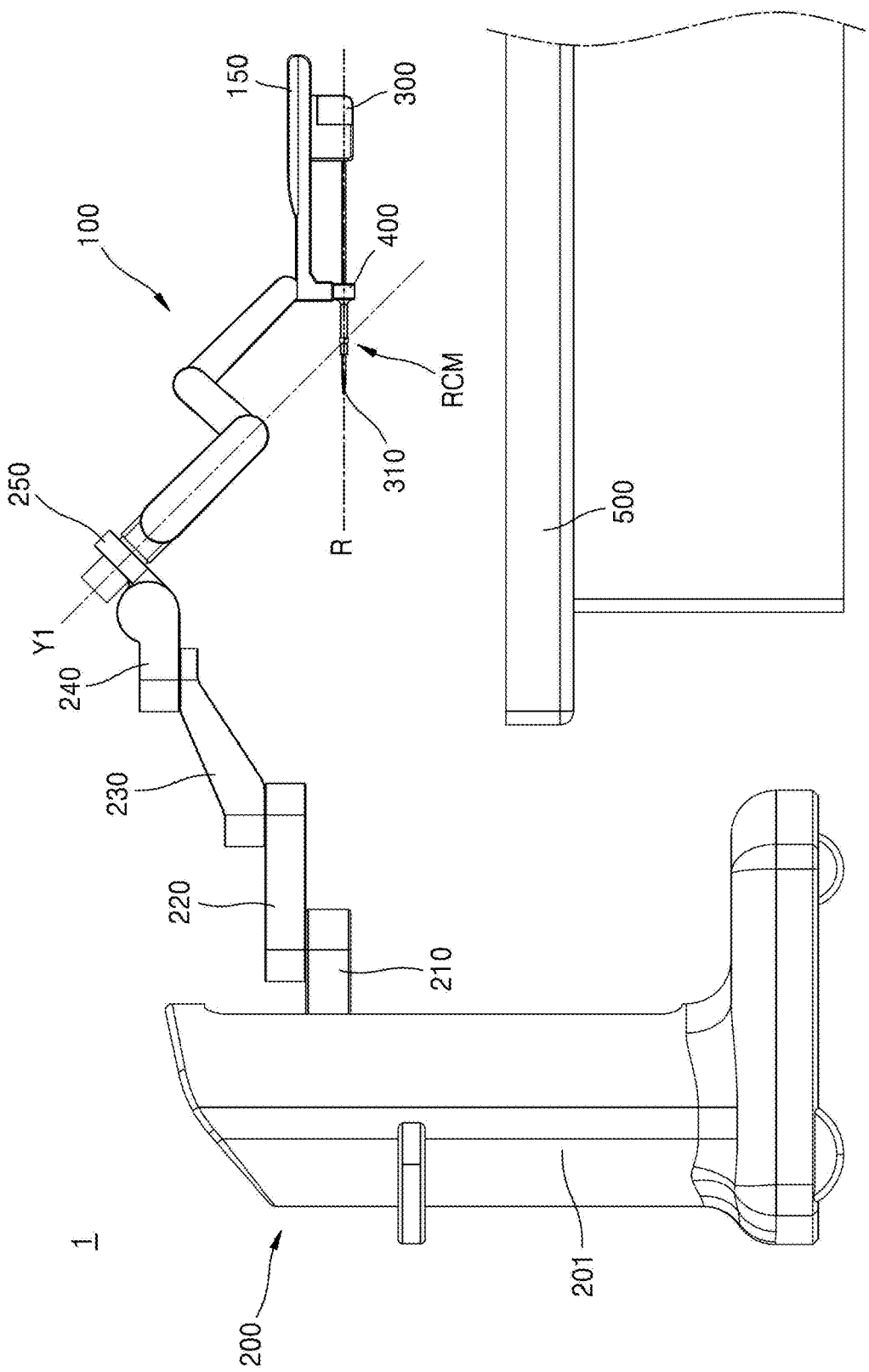
Figure 50:
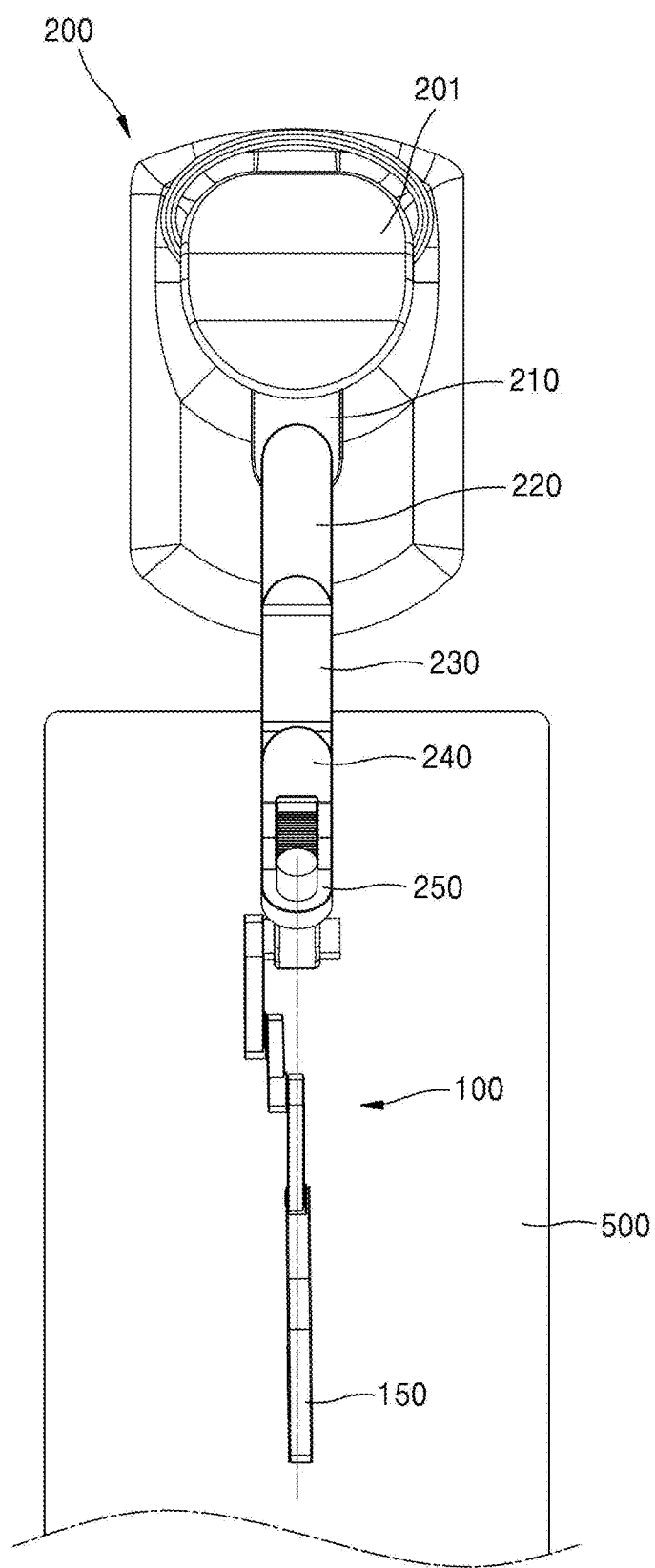

Referring to FIGS. 49 and 50, a state is illustrated in which the end tool 310 of the surgical instrument 300 is disposed in a direction facing the body 201 as the third link 130, the fourth link 140, and the fifth link 150 rotate.

Referring to FIG. 49, the fifth link 150 of the active arm 100 of the surgical robot arm 1 and the surgical instrument 300 coupled thereto may be disposed parallel to the horizontal plane (or the XY plane).

The fifth setup link 250 forms a predetermined angle of 45° with respect to the fourth setup link 240, and the yaw axis Y1, which is the central axis of rotation of the first link 110 rotatably coupled to the fifth setup link 250, forms a predetermined angle of 45° with respect to the horizontal plane.

At this time, as the third link 130 rotates around the pitch axis P, which serves as a rotation center, with respect to the second link 120 in a direction away from the body 201, and the fourth link 140 connected to the third link 130 and the fifth link 150 connected to the fourth link 140 rotate, the end tool 310 of the surgical instrument 300 may be disposed so as to face the body 201.

At this time, since the position of the third joint 135 is fixed, and the positions of the first link 110 and the second link 120 are also fixed, the yaw axis Y1 is maintained, and the RCM positioned on the yaw axis Y1 may also be maintained.

Referring to FIGS. 49 and 50, the surgical instrument 300 can enter parallel to the horizontal plane while the yaw axis Y1 of the surgical robot arm 1 according to the first embodiment of the present disclosure is configured to be inclined at a predetermined angle of 45° with respect to the horizontal plane, from the upper side to the lower side.

In addition, by positioning the yaw axis Y1 to be inclined to form a predetermined angle relative to the roll axis R of the surgical instrument 300 connected to the fifth link, a gimbal lock phenomenon, which may occur when the roll axis R and the yaw axis Y1 are positioned parallel or nearly parallel to each other when the surgical instrument 300 is disposed parallel to the horizontal plane, can be prevented.

FIGS. 51 to 56 are views illustrating the RCM motion of the surgical robot arm according to the first embodiment of the present disclosure around the yaw axis Y1 at a predetermined angle.

Figure 51:
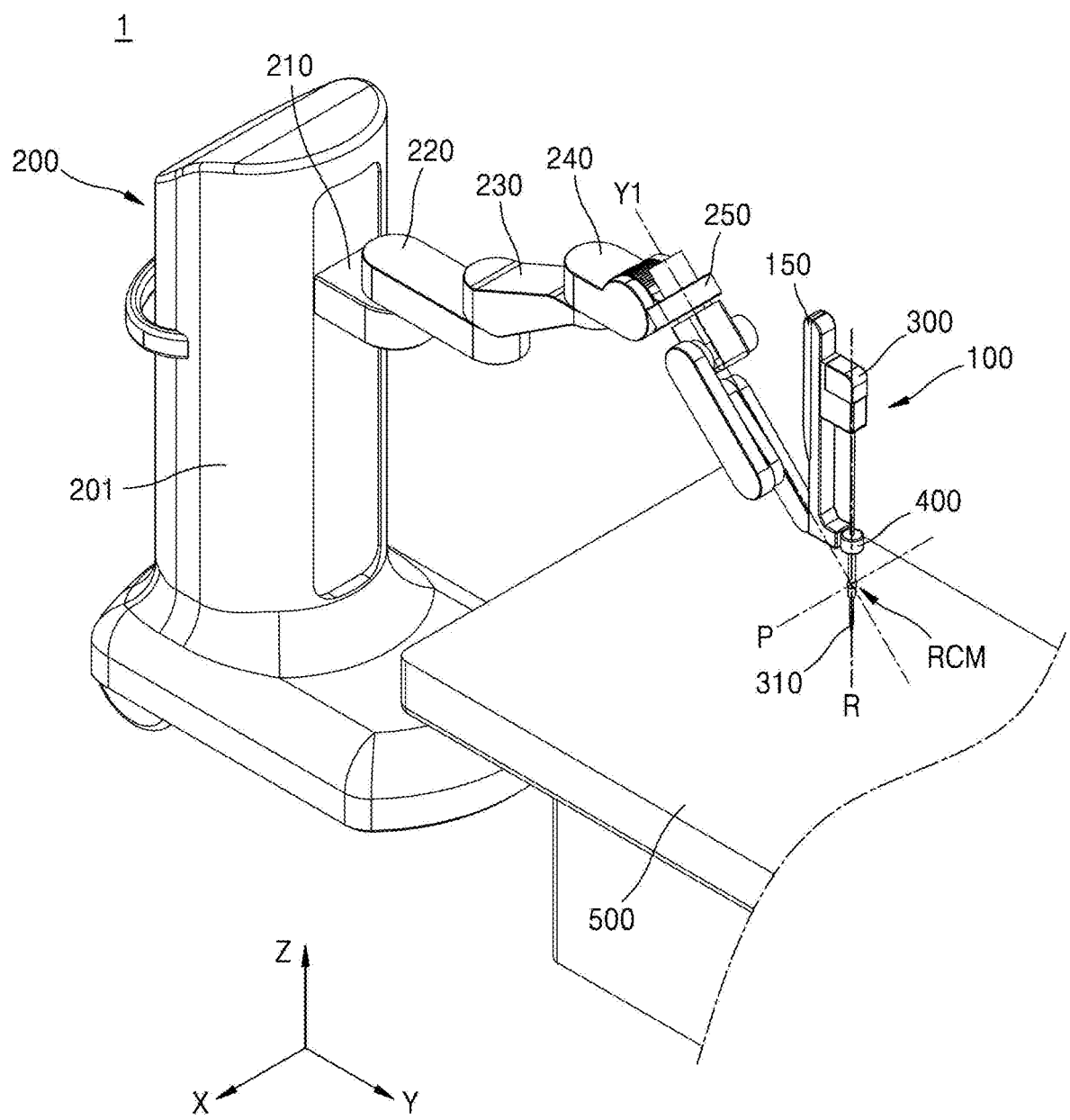
FIGS. 51 to 56 are views illustrating an RCM motion of the surgical robot arm according to the first embodiment of the present disclosure around the yaw axis at a predetermined angle.

Referring to FIG. 51, a state is illustrated in which the fifth setup link 250 forms a predetermined angle of 45° with respect to the fourth setup link 240.

That is, the angle formed by the fifth setup link 250 with respect to the horizontal plane is 45°, and the yaw axis Y1, which is the central axis of rotation of the first link 110 of the active arm 100 rotatably coupled to the fifth setup link 250, forms an angle of 45° with respect to the horizontal plane.

Referring to FIG. 51, in the active arm 100, as the first link 110 and the second link 120 are fixed in position and the third link 130, the fourth link 140, and the fifth link 150 rotate, the RCM can be maintained due to the RCM mechanism described above.

Referring to FIG. 51, the second link 120, the third link 130, and the fourth link 140 may be disposed to partially overlap each other, and the third joint 135, the fourth joint 145, and the fifth joint 155 may be disposed on the yaw axis Y1.

Figure 52:
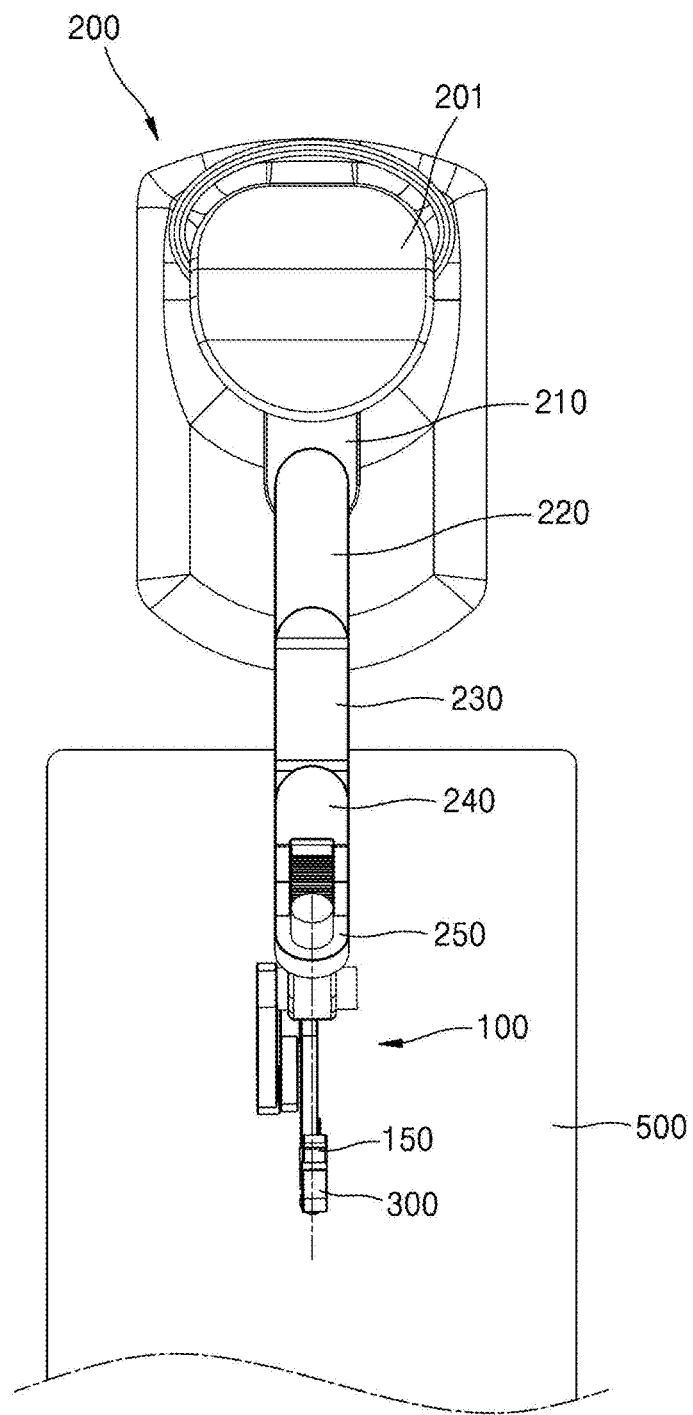

Referring to FIGS. 51 to 52, the fifth link 150 may be rotated with respect to the fourth link 140 so that the longitudinal central axis of the fifth link 150 may be configured parallel to the Z-axis. That is, the roll axis R of the surgical instrument 300 may be perpendicular to the bed 500 or the horizontal plane.

At this time, the yaw axis Y1 of the surgical robot arm 1 may be configured to extend from the upper side to the lower side and to be inclined at a predetermined angle of 45° with respect to the horizontal plane, and thus, when the surgical instrument 300 is disposed vertically, the yaw axis Y1 can be configured to be inclined with respect to the roll axis R of the surgical instrument 300, thereby preventing a gimbal lock phenomenon that may occur when the angle between the yaw axis Y1 and the roll axis R is small, or when the yaw axis Y1 and the roll axis R are positioned parallel to each other.

Figure 53:
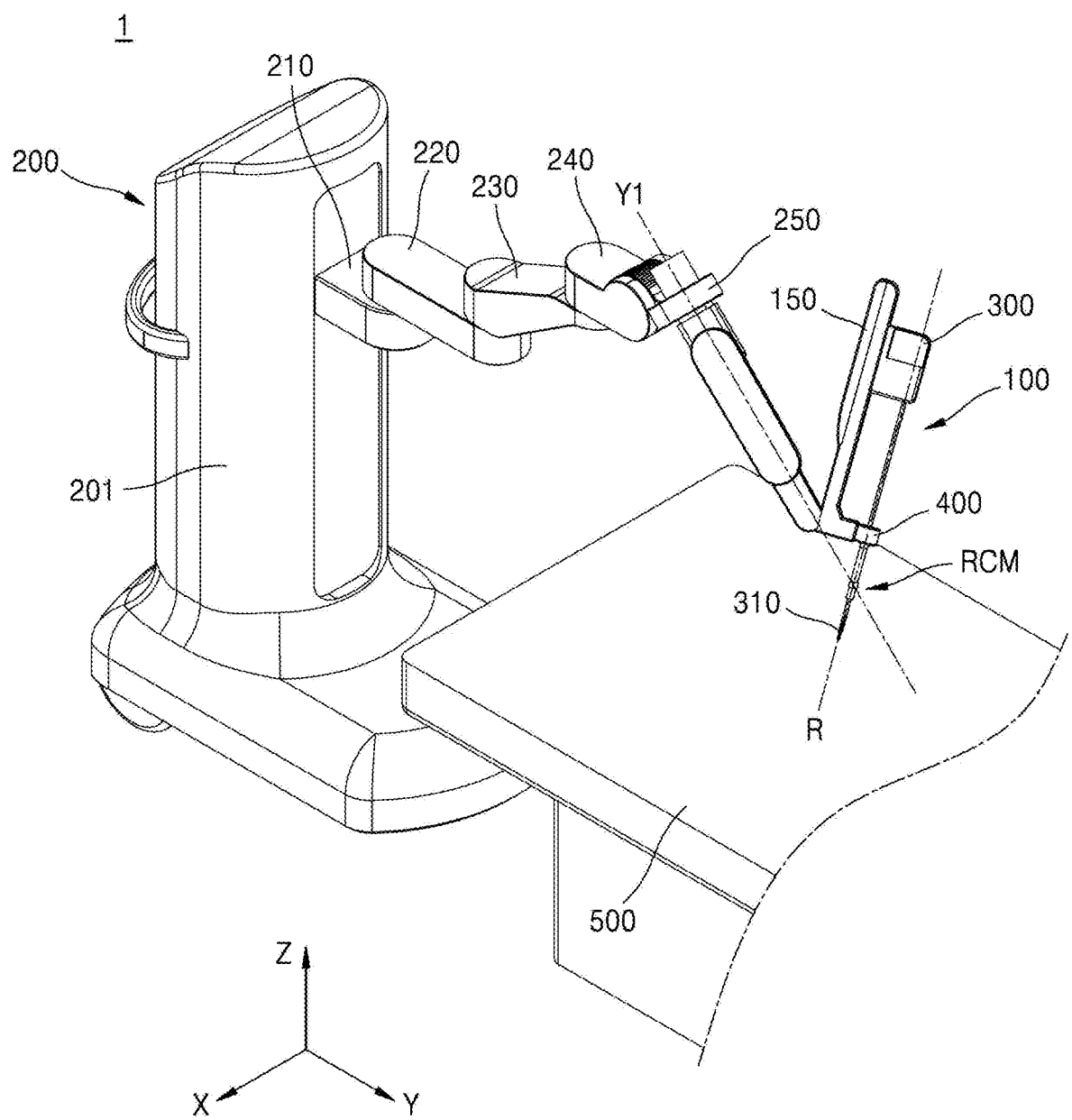
Figure 54:
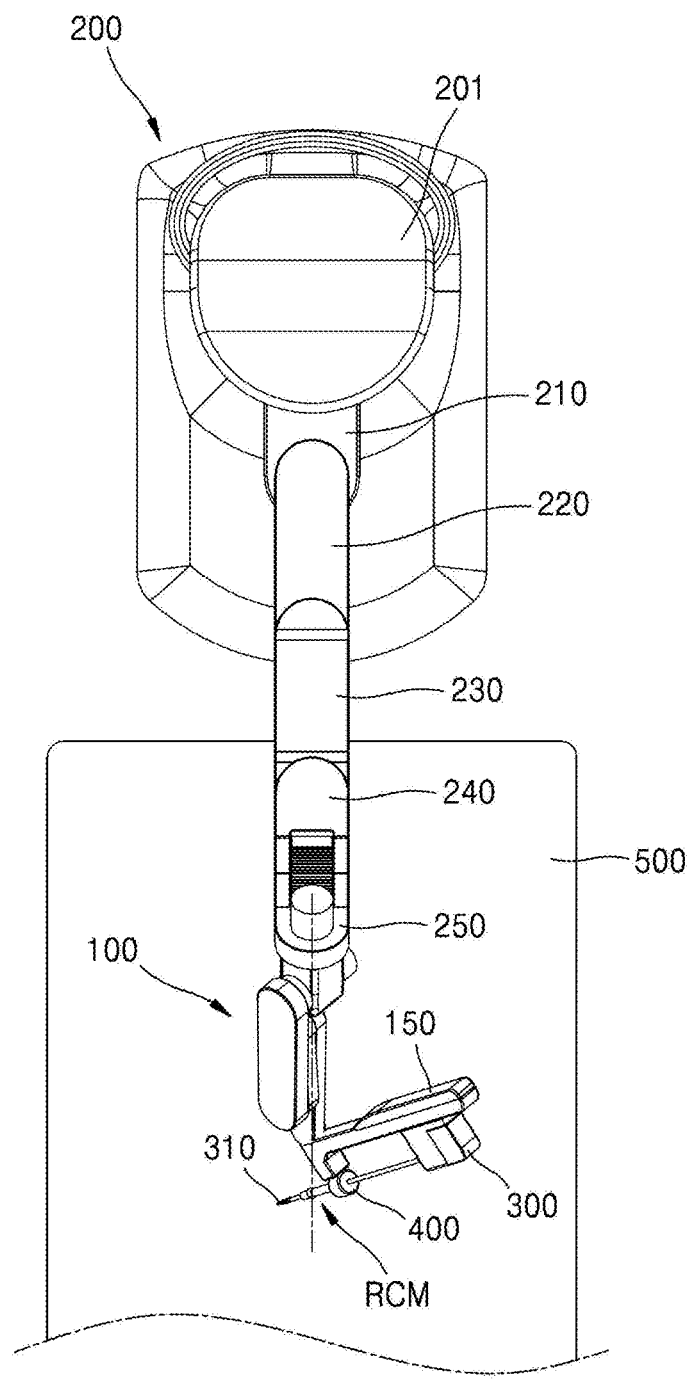

Referring to FIGS. 53 and 54, as the first link 110 rotatably coupled to the fifth setup link 250 in FIG. 51 is rotated around the yaw axis Y1, which serves as the central axis of rotation, in a first direction (in the clockwise direction based on FIG. 53), the second link 120, the third link 130, the fourth link 140, and the fifth link 150 that are directly or indirectly connected to the first link 110 may be rotated.

In this case, the third joint 135, the fourth joint 145, the fifth joint 155, and the RCM form a parallelogram, and the active arm 100 can perform the yaw motion while the RCM remains constant.

Figure 55:
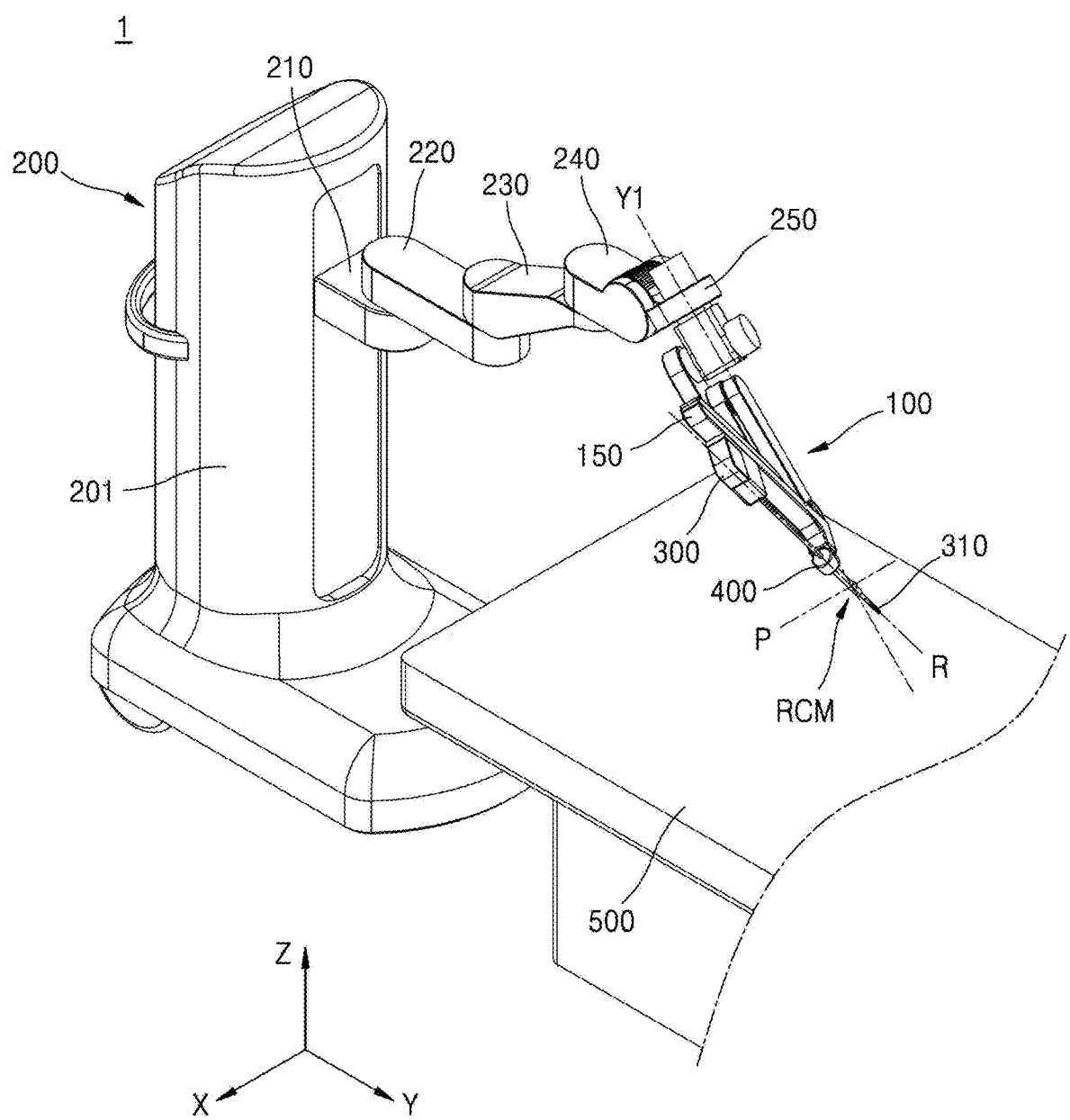
Figure 56:
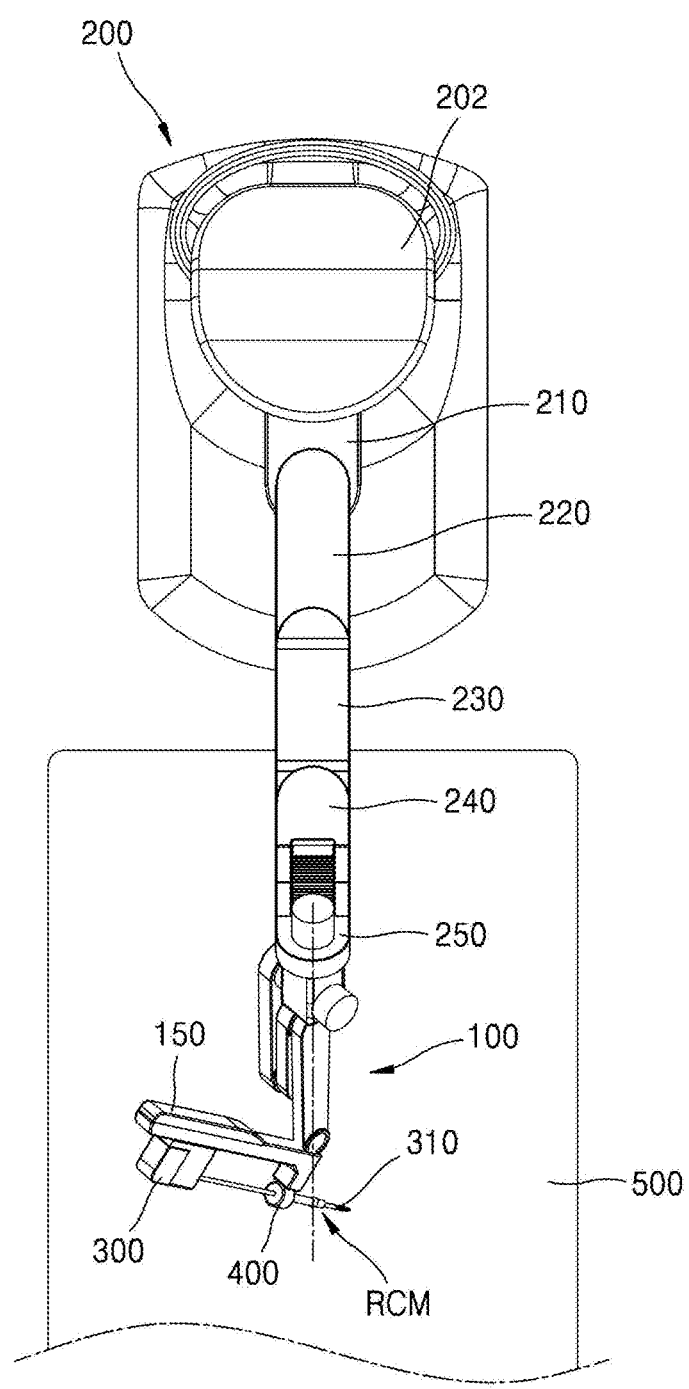
Figure 57:
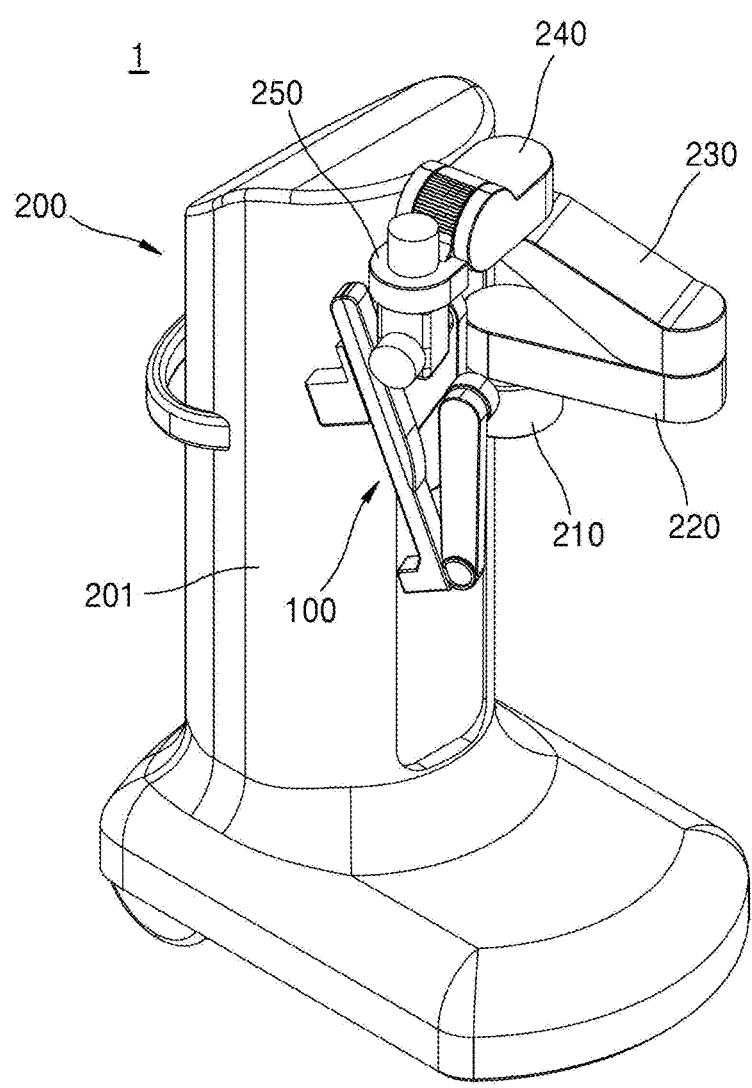
FIGS. 57 to 60 are views illustrating states in which the surgical robot arm according to the first embodiment of the present disclosure moves.
Figure 58:
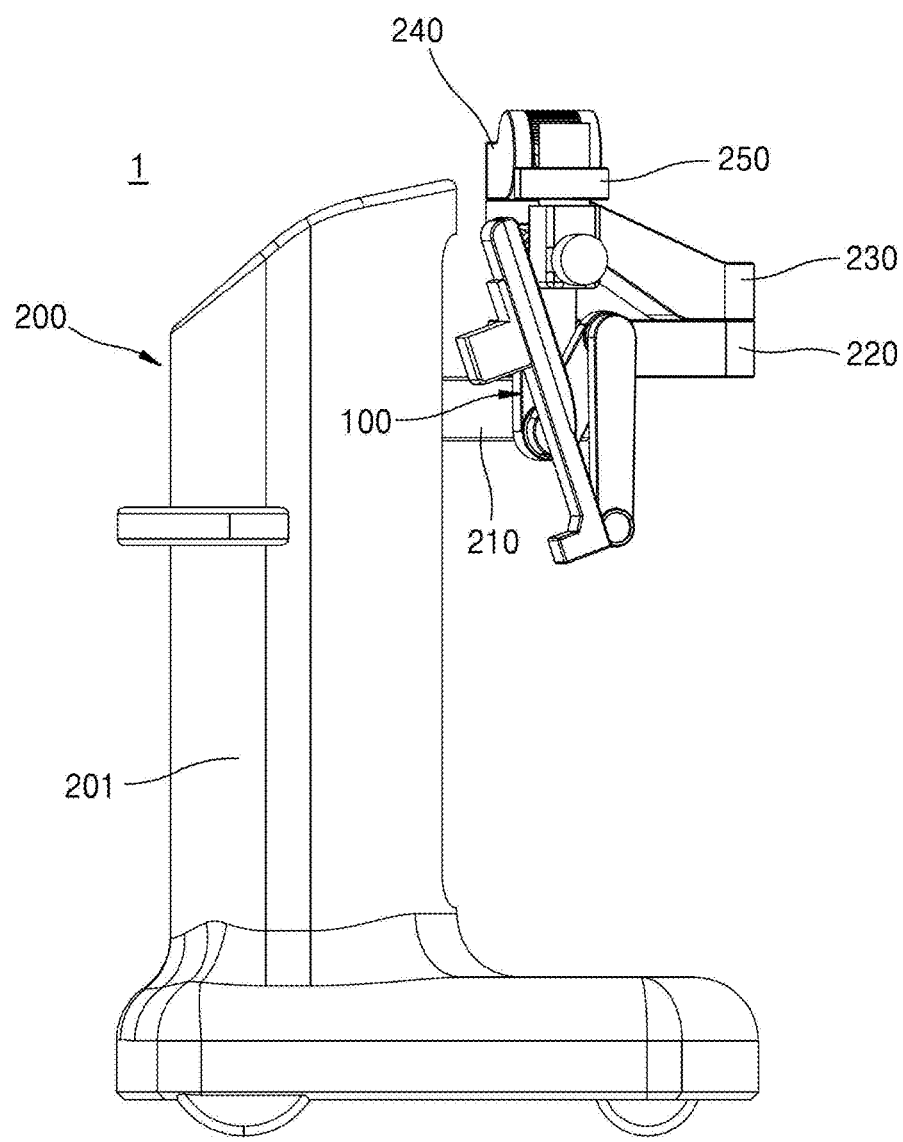
Figure 59:
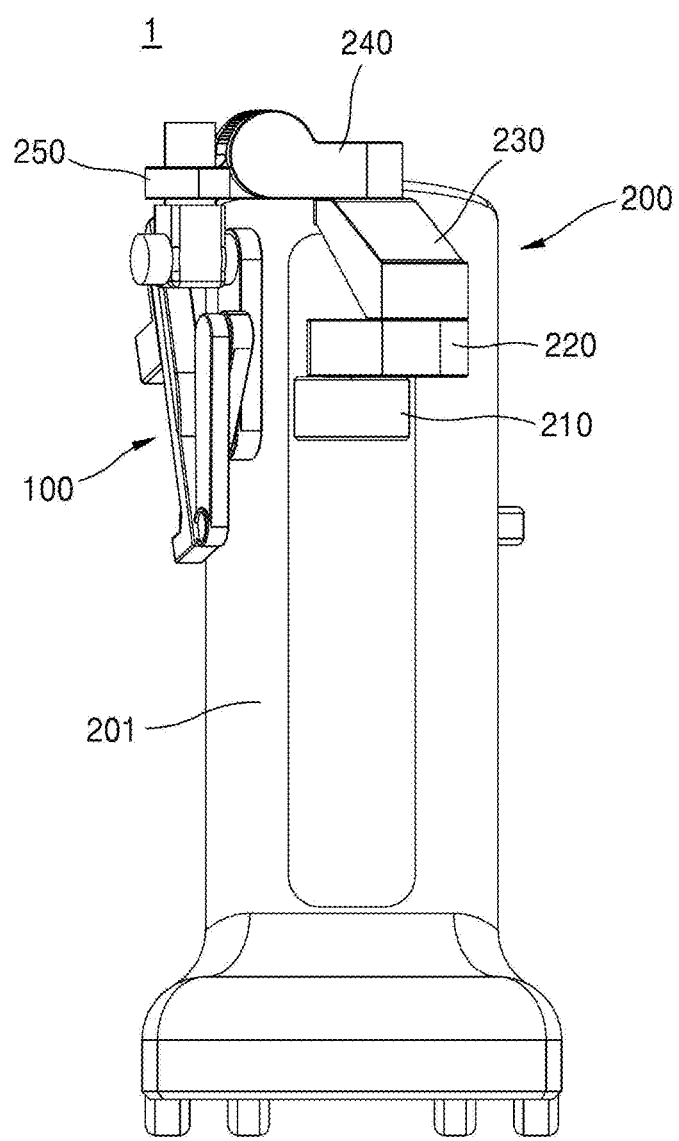
Figure 60:
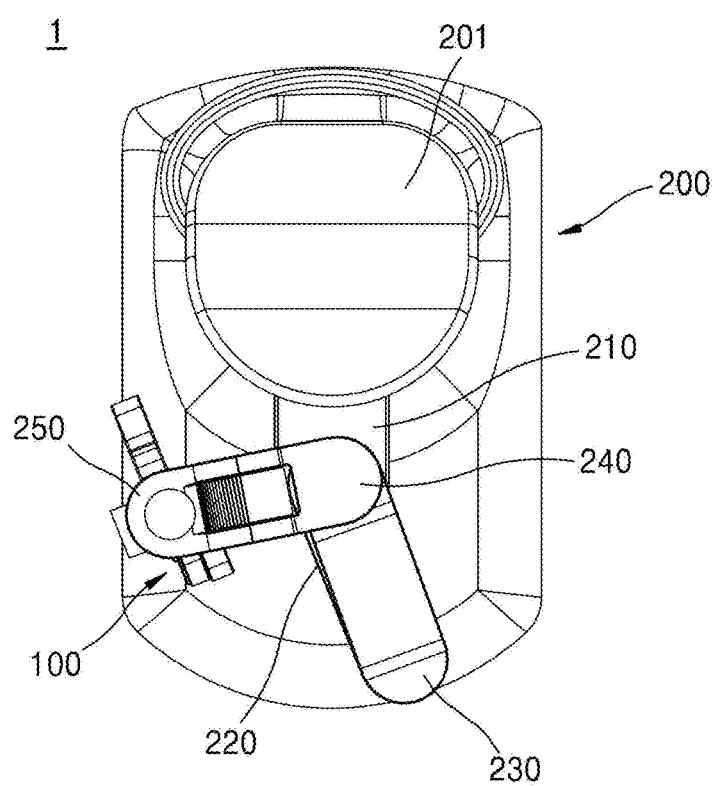

Referring to FIGS. 55 and 56, as the first link 110 rotatably coupled to the fifth setup link 250 in FIG. 51 is rotated around the yaw axis Y1, which serves as the central axis of rotation, in a second direction (in the counterclockwise direction based on FIG. 55), the second link 120, the third link 130, the fourth link 140, and the fifth link 150 that are directly or indirectly connected to the first link 110 may be rotated.

In this case, the third joint 135, the fourth joint 145, the fifth joint 155, and the RCM form a parallelogram, and the active arm 100 can perform the yaw motion while the RCM remains constant.

Referring to FIGS. 53 to 56, when the active arm 100 performs a yaw motion, the yaw axis Y1 and the roll axis R of the surgical instrument 300 are positioned to be inclined at a predetermined angle relative to each other, thereby preventing a gimbal lock phenomenon that may occur when the roll axis R and the yaw axis Y1 are positioned parallel or nearly parallel to each other when the surgical instrument 300 is disposed parallel to the horizontal plane.

FIGS. 57 to 60 are views illustrating arrangement states of the respective links during the movement of the surgical robot arm according to the first embodiment of the present disclosure.

The surgical robot arm 1 may include the setup arm 200 and the active arm 100. The setup arm 200 may include a plurality of setup arm links. In addition, the setup arm 200 may include a plurality of setup joints.

Specifically, the second setup link 220 is axially coupled to the first setup link 210 through the second setup joint 225 and is rotatable relative to the first setup link 210. The third setup link 230 is axially coupled to the second setup link 220 through the third setup joint 235 and is rotatable relative to the second setup link 220.

The fourth setup link 240 is rotatable relative to the third setup link 230 through the fourth setup joint 245. The fifth setup link 250 is rotatable relative to the fourth setup link 240 through the fifth setup joint 255.

Referring to FIGS. 57 to 60, the first setup link 210, the second setup link 220, the third setup link 230, and the fourth setup link 240 may be coupled so that the heights thereof increase relatively in the Z-axis, which is a height direction.

Accordingly, interference or collision between the first setup link 210, the second setup link 220, the third setup link 230, and the fourth setup link 240 can be prevented during relative rotation by ensuring that no other setup link is positioned within the rotation path, thereby allowing the links to rotate freely without restrictions on the range of rotation.

In addition, as there is no restriction on the range of rotation of the plurality of setup links, the first setup link 210, the second setup link 220, the third setup link 230, and the fourth setup link 240 can be disposed to overlap each other in the height direction, thereby minimizing the area occupied by the setup arm 200.

Meanwhile, the fifth setup link 250 is rotatably coupled to the fourth setup link 240. Specifically, the fifth setup link 250 is rotatably coupled to the fourth setup link 240 around the fifth setup joint 255, which serves as the rotation center, with the pitch axis P, formed parallel to the X-axis (based on FIG. 57), as the central axis of rotation.

At this time, when the fifth setup link 250 is rotated with respect to the fourth setup link 240 to be parallel to the fourth setup link 240 on the same plane, the yaw axis Y1, which is the central axis of rotation of the first link 110 coupled to the fifth setup link 250, forms an angle of 90° with the horizontal plane.

At this time, the motor may be driven to rotate the third link 130, the fourth link 140, and the fifth link 150, and the third link 130, the fourth link 140, and the fifth link 150 may overlap each other, thereby minimizing the area occupied by the active arm 100.

Referring to FIGS. 57 to 60, the area occupied by the surgical robot arm 1 can be minimized by minimizing the area occupied by the plurality of setup links connected to the body 201 and the active arms 100, that is, the area occupied when the surgical robot arm 1 is not in use can be minimized, thereby facilitating movement and storage.

FIGS. 61 to 63 are views illustrating a state in which the surgical robot arm according to the first embodiment of the present disclosure is disposed near a patient's surgical site and the surgical instrument is disposed directly facing a patient.

Referring to FIGS. 61 to 63, a patient may be lying on the bed 500, and a plurality of surgical robot arms may be disposed around the bed 500. The surgical instrument 300 and the trocar 400 may each be coupled to the active arm 100, specifically, the fifth link 150, of each of the plurality of surgical robot arms, and surgery may be performed by forming RCMs at different points on the patient's body.

In each of the plurality of surgical robot arms 1 disposed on the outer side of the bed 500, a user, such as medical staff, can reposition the active arm 100 by rotating the setup arm 200, specifically through the rotation of the plurality of setup links, and by repositioning the setup arm 200, the plurality of setup links 210, 220, 230, 240, and 250, and the plurality of links 110, 120, 130, 140, and 150 provided on each active arm 100, the surgical space can be used efficiently without needing to move the body 201, thereby reducing surgical time by minimizing the movement of surgical equipment such as the body 201.

<Surgical Method Using Surgical Robot>

Hereinafter, a surgical method using a surgical robot including the surgical robot arm according to the first embodiment of the present disclosure will be described. Here, a position through which the trocar 400 is inserted and the surgical instrument 300 passes is referred to as a port.

The surgical method using the surgical robot arm of the present disclosure may include disposing the body of the surgical robot arm having a modular configuration on one side of a port of a patient into which the surgical instrument is to be inserted, adjusting the setup arm that includes the body, disposing the fifth link of the active arm, on which the surgical instrument is mounted, in a substantially horizontal state, mounting the surgical instrument on the fifth link of the active arm, moving the surgical instrument mounted on the active arm so as to be inserted into the patient's body, and performing surgery while the surgical instrument maintains an RCM.

This will be described below in more detail.

Referring to FIGS. 1 and 4, the surgical robot arm 1 having a modular configuration is disposed on one side of the bed 500 on which a patient may be placed. At this time, the body 201 of the surgical robot arm 1 may be disposed on the same side as the surgical instrument 300, relative to the patient's port (the insertion location of the trocar 400). Alternatively, as illustrated in FIGS. 17 to 19, the body 201 may be disposed facing the surgical instrument 300 relative to the patient's port.

Next, in the adjusting of the setup arm 200, the position of an end portion of the active arm 100 coupled to the fifth setup link 250 may be determined by adjusting the plurality of setup links 210, 220, 230, 240, and 250 that are movable in a preset direction on the body 201.

Referring to FIGS. 20 to 23, the first setup link 210 movably coupled to the body 201 is movable in a preset direction (in a vertical direction based on FIG. 20), the second setup link 220 is rotatably and axially coupled to the first setup link 210, the third setup link 230 is rotatably and axially coupled to the second setup link 220, and the fourth setup link 240 is rotatably and axially coupled to the third setup link 230.

Referring to FIG. 1, the fifth setup link 250 is rotatably coupled to the fourth setup link 240 around a central axis of rotation parallel to the pitch axis P.

Referring to FIG. 1, the second setup link 220, the third setup link 230, and the fourth setup link 240 are connected to each other so as to rotate relative to each other around respective central axes of rotation parallel to the Z-axis (based on FIG. 1) in the height direction of the setup arm 200. Thus, the second setup link 220, the third setup link 230, the fourth setup link 240, and the fifth setup link may be rotated to determine the position of the setup arm 200.

After the adjusting of the setup arm 200, the position of the active arm 100, specifically, the positions of the plurality of links, coupled to the fifth setup link 250 may be adjusted. The links may be disposed to overlap each other by folding two or more links rather than having a plurality of links stretched out long.

Next, the surgical instrument 300 is mounted on the fifth link 150 of the active arm 100. In this case, no components, such as links, are positioned between the surgical instrument 300 and the patient. That is, as described above, when the surgical instrument 300 is mounted on the fifth link 150, the surgical instrument 300 may be configured to be mounted downward i.e., in the direction in which the links are positioned when all the links are folded rather than upward.

In other words, the surgical instrument 300 coupled to the fifth link 150 is disposed to face inwardly of the surgical robot arm 1. That is, in a state in which the surgical instrument 300 coupled to the fifth link 150 is horizontal and the end tool 310 thereof is disposed in a direction away from the body 201, the fifth link 150 is disposed such that a surface thereof to which the surgical instrument 300 is coupled faces downward. In other words, the surgical instrument 300 coupled to one side of the fifth link 150 is positioned lower than the fifth link 150.

With this configuration, even when the surgical robot arm 1 having a modular configuration is horizontally positioned in a state of being disposed adjacent to the patient's port, the fifth link 150, on which the surgical instrument 300 is mounted, is prevented from coming into direct contact with the patient, thereby having the advantage of reducing vibration and improving rigidity.

Next, the surgical instrument 300 mounted on the fifth link 150 is linearly moved to insert the end tool 310 of the surgical instrument 300 into the patient's body. Next, the surgical instrument 300 performs surgery while maintaining the RCM.

As described above, in the present disclosure, the extension line connecting the third joint 135 to the RCM is configured to be aligned with or parallel to the yaw axis Y1, and is configured to be inclined with respect to the roll axis R of the surgical instrument 300, which is coupled to the fifth link 150.

As a result, the roll axis R and the yaw axis Y1, which are formed when the surgical instrument 300 is positioned parallel to the bed 500 on which the patient is lying or to the horizontal plane, are configured to be inclined at a predetermined angle with respect to each other, thereby preventing a gimbal lock phenomenon that may occur when the angle between the yaw axis Y1 and the roll axis R is small, or when the yaw axis Y1 and the roll axis R are positioned parallel to each other.

In addition, since the active arm 100, which is rotatably connected to the setup arm 200, specifically the fifth setup link 250, and more specifically the yaw axis Y1, which is the central axis of rotation of the first link 110, is configured in the upper-to-lower direction (based on FIG. 1), the range of movement between the plurality of links is relatively reduced, thereby improving space utilization.

In addition, when a plurality of surgical robot arms are disposed on the outer side of the bed 500 on which the patient is lying, a driving range of each of the surgical robot arms is relatively small, thereby preventing interference between the plurality of surgical robot arms, and correspondingly making it easier to deploy the plurality of surgical robot arms.

In other words, these surgical robot arms are disposed in the vicinities of a plurality of ports of the patient, respectively, so that the overall length of the deployed surgical robot arms is shortened, thereby obtaining an effect of reducing vibration and increasing rigidity.

In addition, in the present disclosure, in a state in which the surgical instrument is disposed in parallel, the active arm 100 is coupled to the fifth setup link 250, which is an end portion of the setup arm 200 that is disposed above the active arm 100, and the yaw axis Y1 is disposed from the upper side to the lower side, so that one surface of the fifth link 150, to which the surgical instrument 300 is coupled, is disposed to face downward, and no components such as links are disposed between the surgical instrument 300 and the patient.

With this configuration, in the surgical robot arm, vibration can be reduced and rigidity can be improved.

MODE FOR INVENTION

Second Embodiment of Surgical Robot Arm

Hereinafter, a surgical robot arm according to a second embodiment of the present disclosure will be described. Here, the surgical robot arm according to the second embodiment of the present disclosure is different from the surgical robot arm 1 according to the first embodiment of the present disclosure described above in that the configuration of the setup links is changed. The configuration changed from the first embodiment as described above will be described in detail later.

Figure 64:
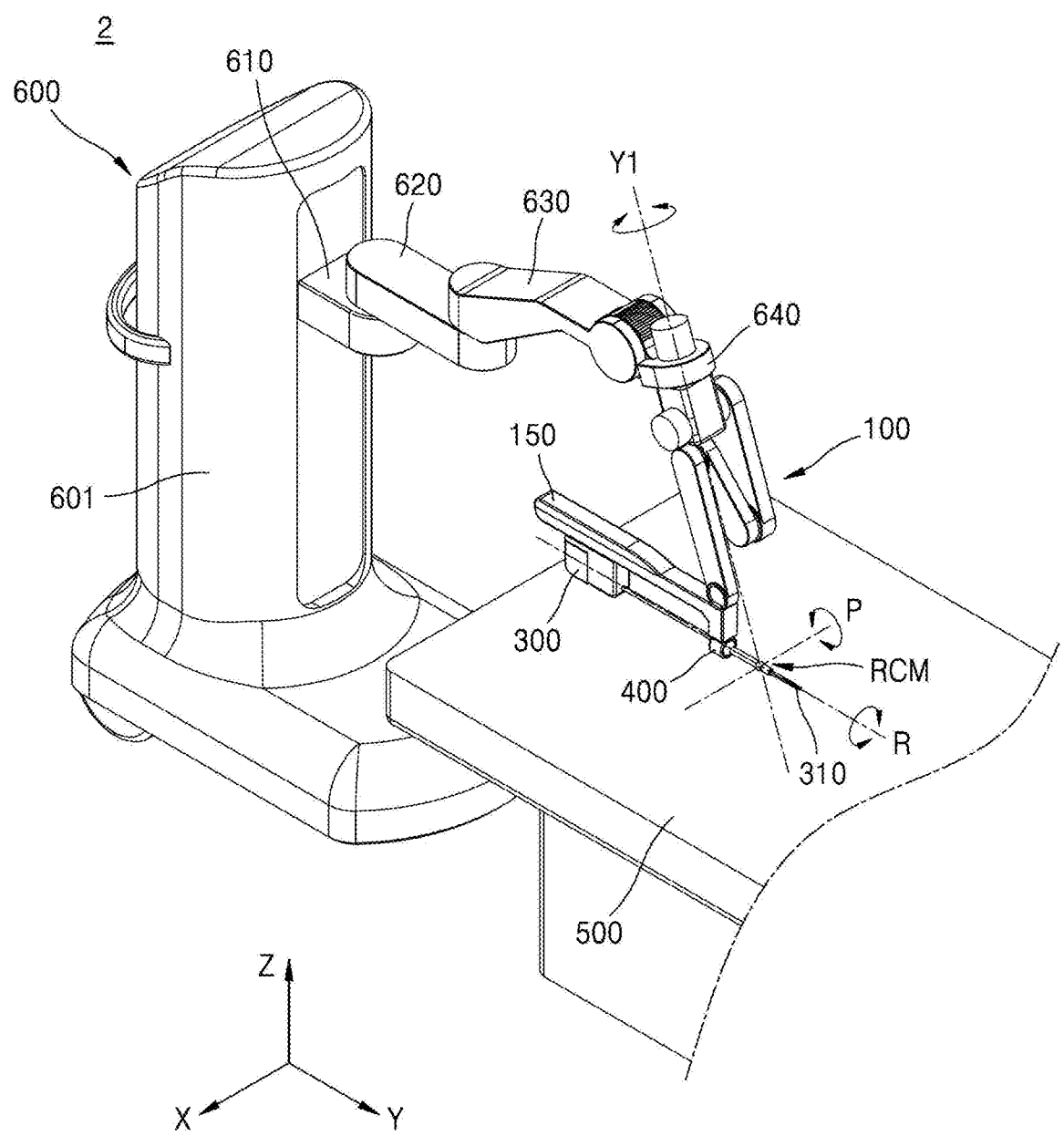
FIGS. 64 to 66 are views illustrating a first arrangement state of a surgical robot arm according to a second embodiment of the present disclosure.
Figure 65:
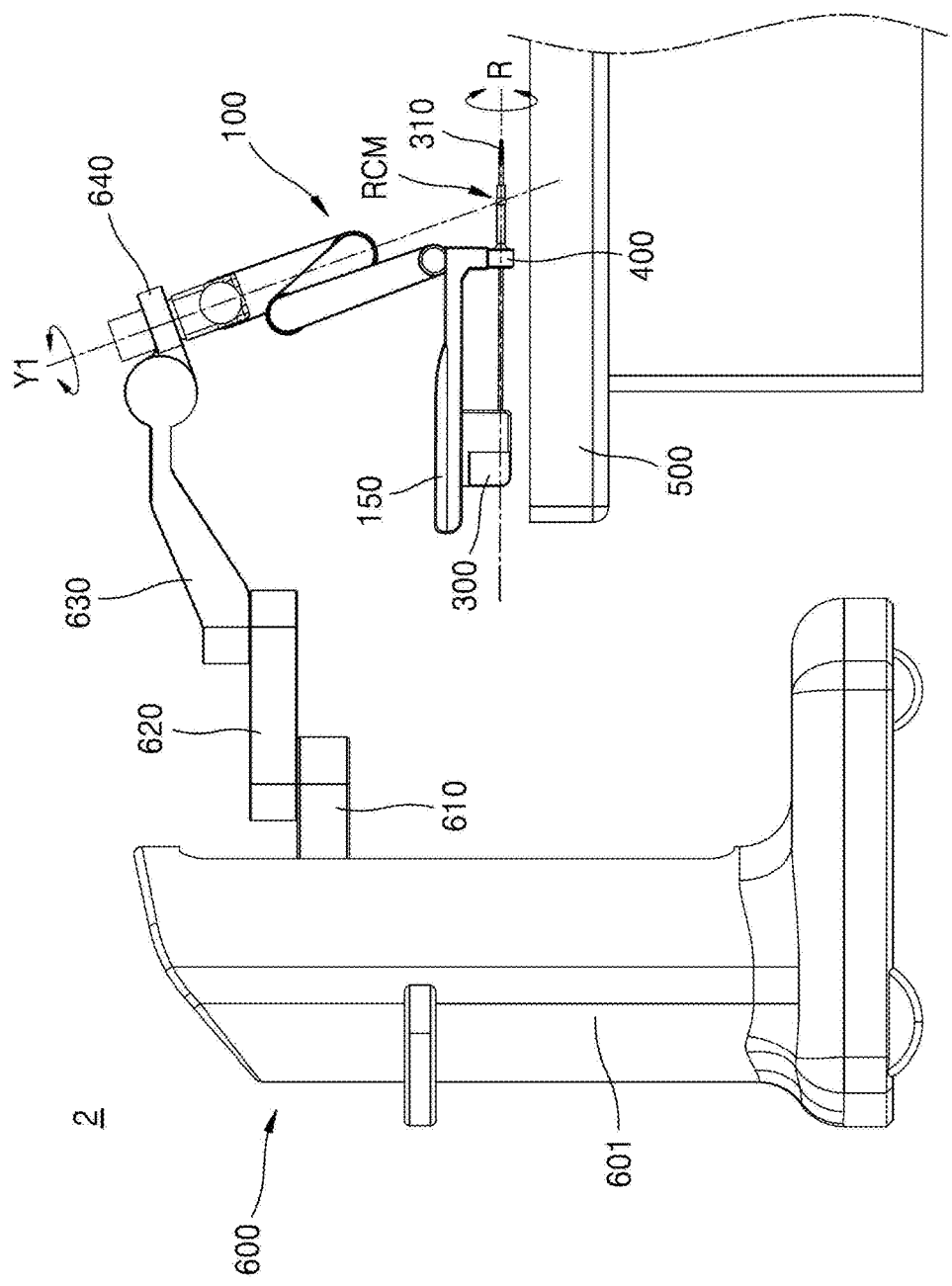
Figure 66:
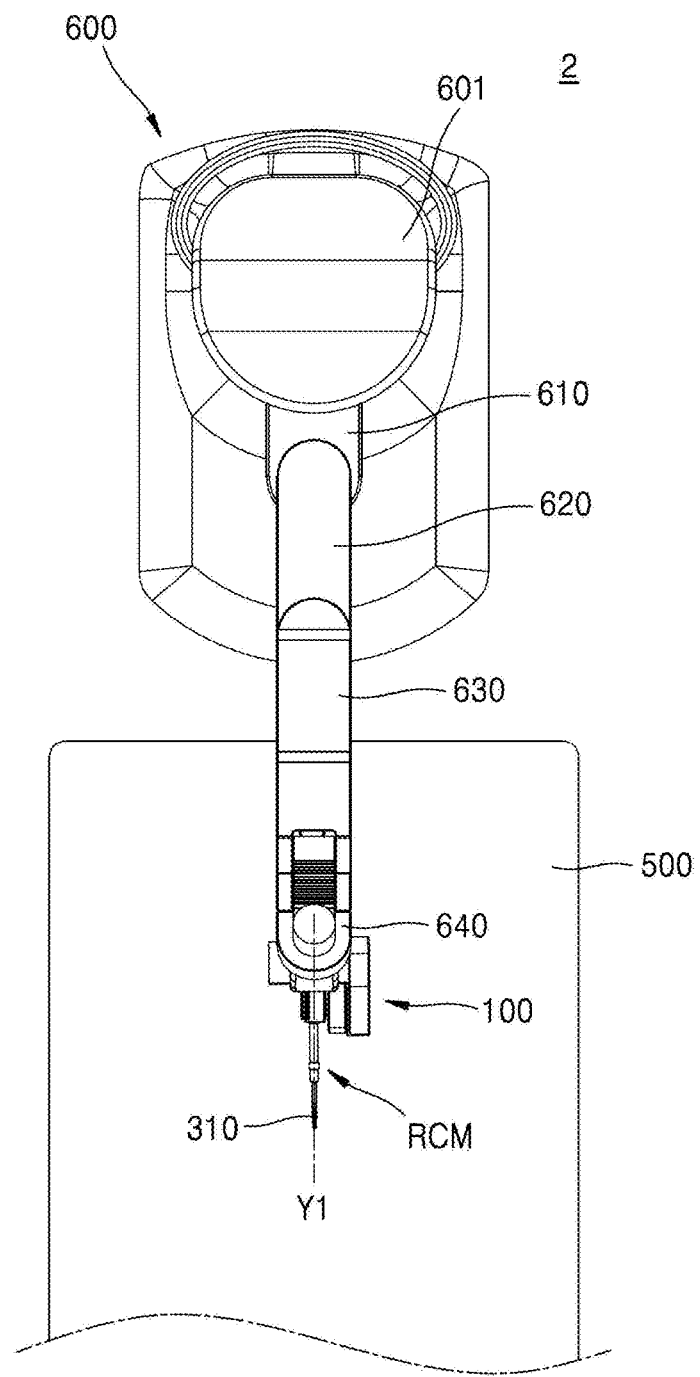

FIGS. 64 to 66 are views illustrating a first arrangement state of the surgical robot arm according to the second embodiment of the present disclosure.

A surgical robot arm 2 according to the second embodiment of the present disclosure may include a setup arm 600 and the active arm 100. The setup arm 600 is rotatably coupled to the active arm 100 and may include a body 601, a first setup link 610, a second setup link 620, a third setup link 630, and a fourth setup link 640.

The surgical robot arm 2 according to the second embodiment of the present disclosure is the same as the surgical robot arm 1 according to the first embodiment of the present disclosure in terms of the configuration, operating principle, and effect of the body 201, the plurality of setup links, and the active arm 100, except that, in relation to the configuration of the setup arm 600, the third setup link 630 is included as a single configuration that integrates the third setup link 230 and the fourth setup link 240 of the surgical robot arm 1 according to the first embodiment of the present disclosure, resulting in a reduction of one degree of freedom, and thus a detailed description thereof will be omitted in the overlapping range.

Figure 67:
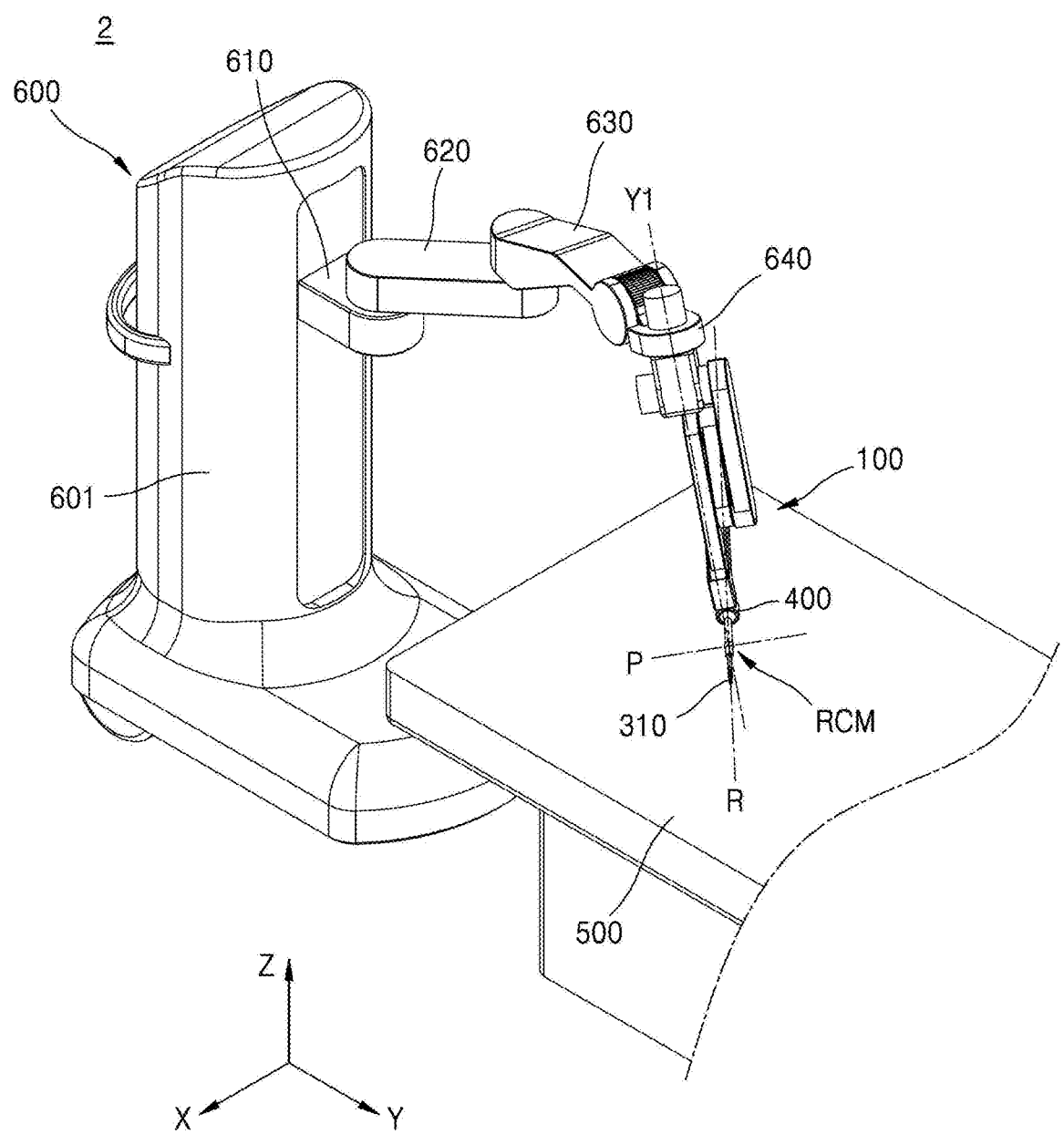
FIGS. 67 to 69 are views illustrating a second arrangement state of the surgical robot arm according to the second embodiment of the present disclosure.
Figure 68:
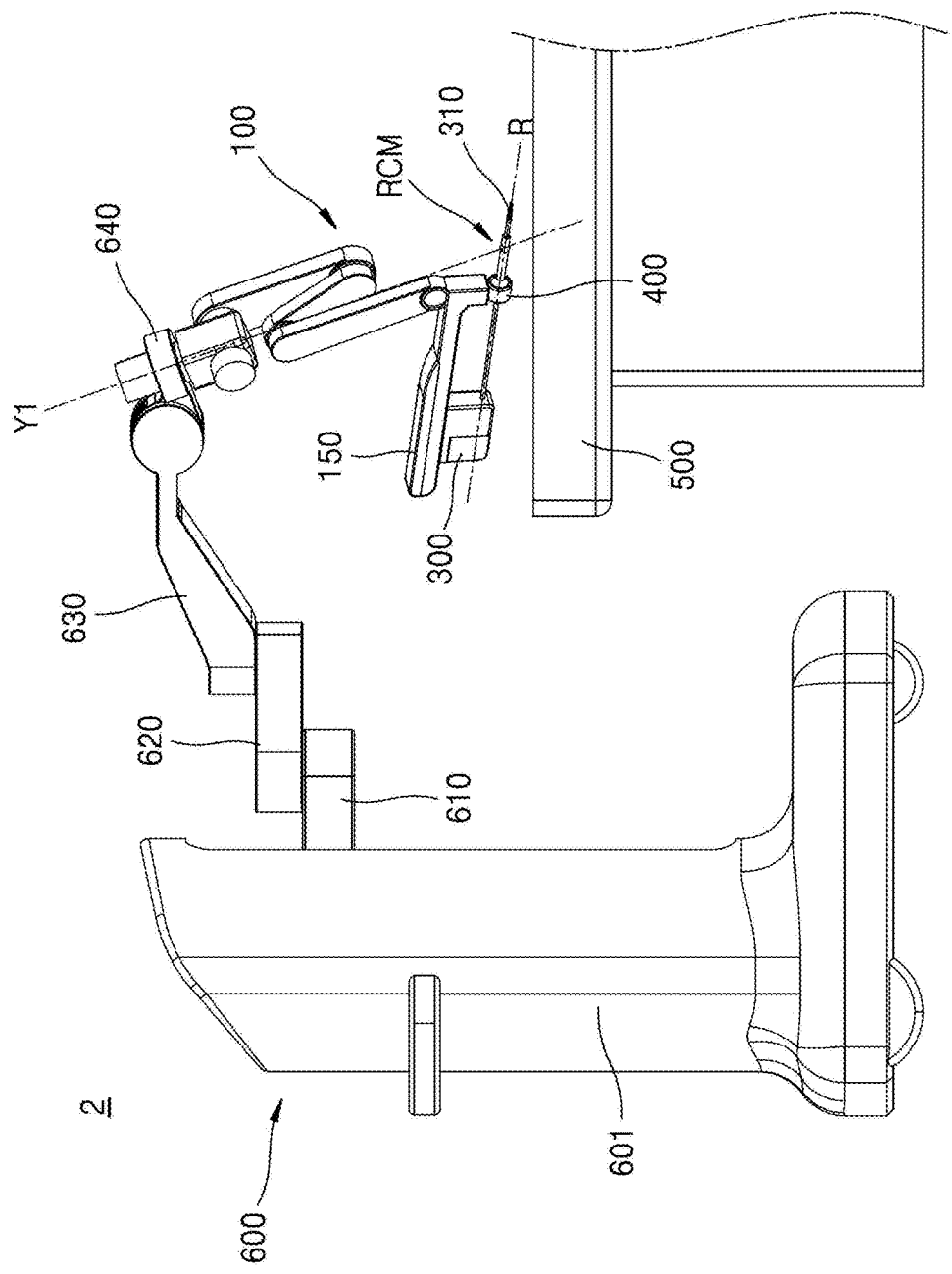
Figure 69:
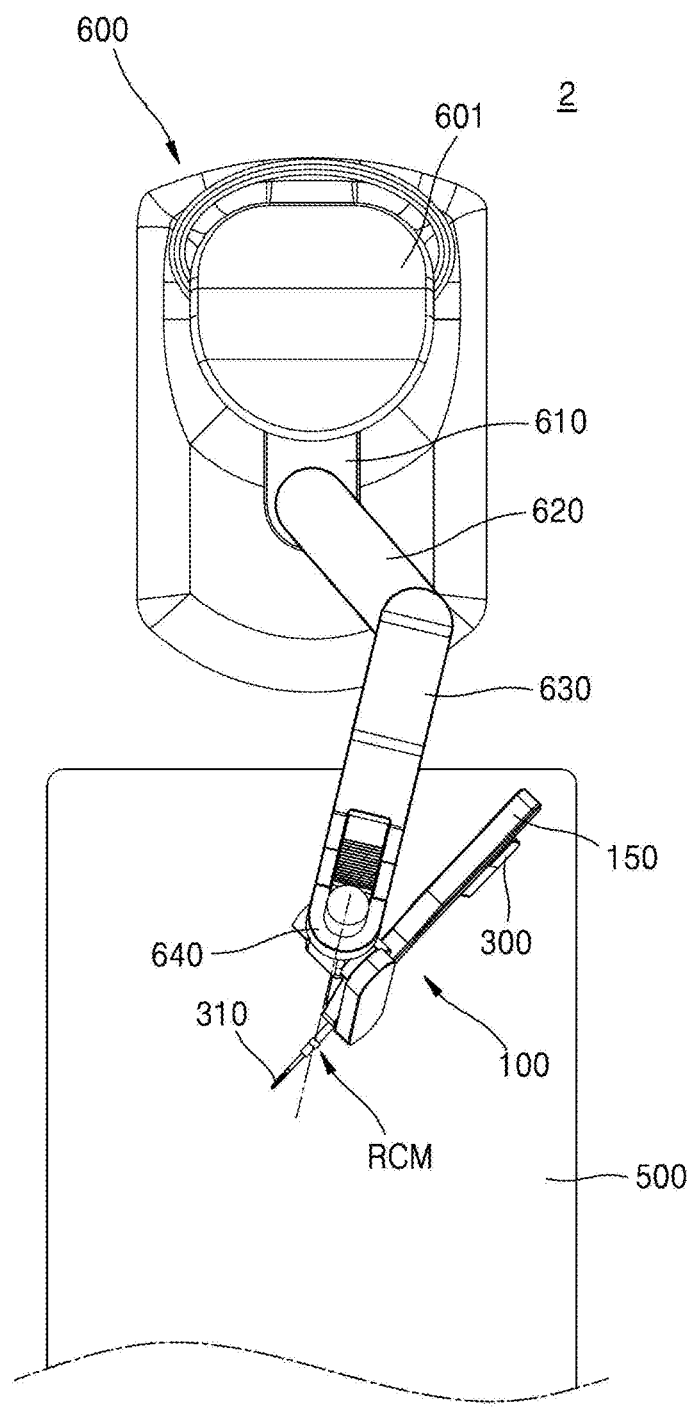

FIGS. 67 to 69 illustrate a second arrangement state of the surgical robot arm 2 according to the second embodiment of the present disclosure, in which the second setup link 620 and the third setup link 630 are rotated compared to the first arrangement state described above.

By rotating the second setup link 620 and the third setup link 630, a gap, i.e., a distance in the Y-axis direction, between the body 601 and the active arm 100, is reduced, allowing an RCM to move in a direction parallel to the Y-axis.

In addition, as the active arm 100, specifically the first link 110, which is rotatably coupled to the fourth setup link 640, rotates around the yaw axis Y1, the position of the surgical instrument 300 may be changed while the RCM remains constant. That is, an entry angle of the surgical instrument 300 into the RCM and the roll axis R can be set differently.

Figure 70:
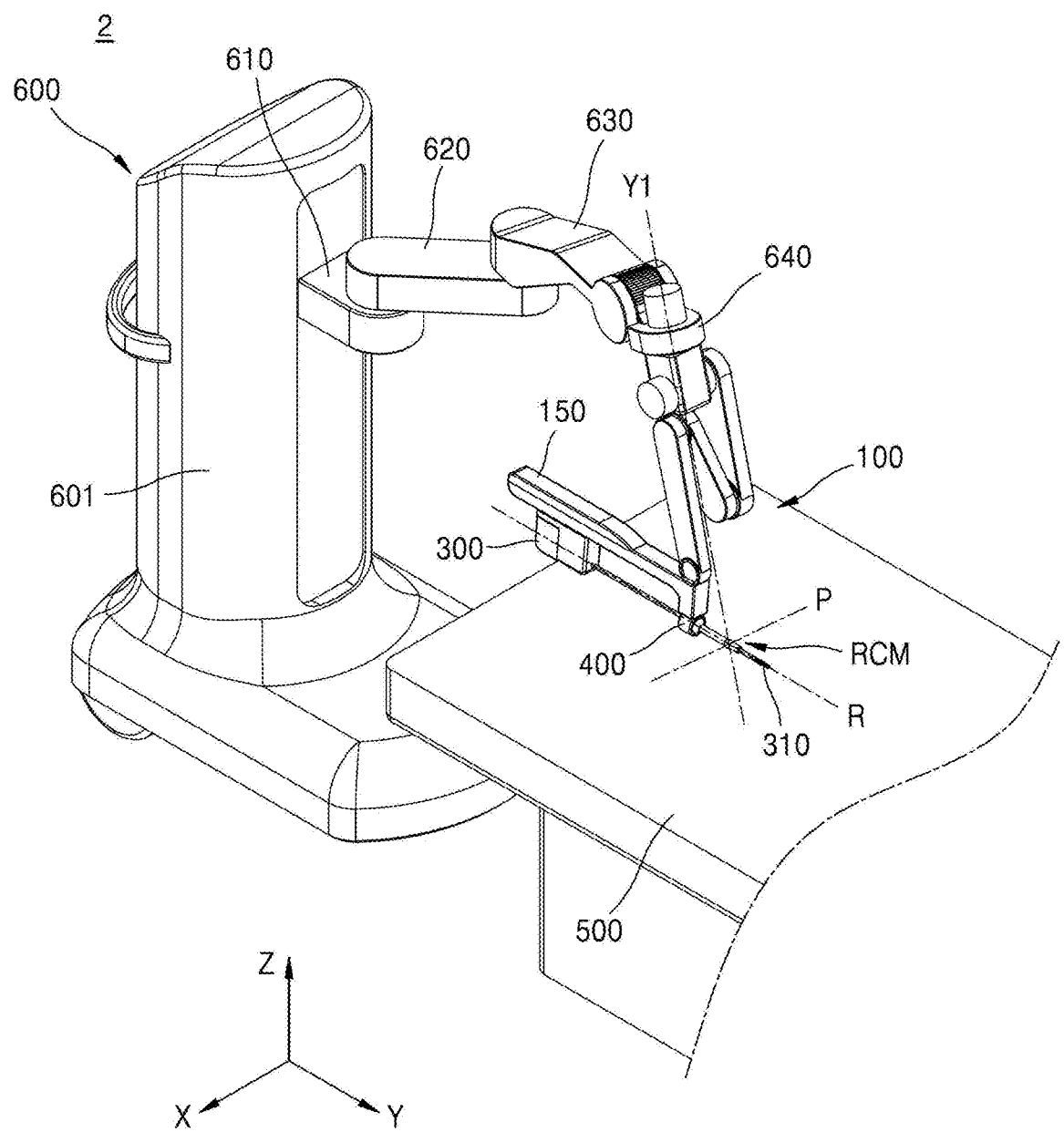
FIGS. 70 to 72 are views illustrating a third arrangement state of the surgical robot arm according to the second embodiment of the present disclosure.
Figure 71:
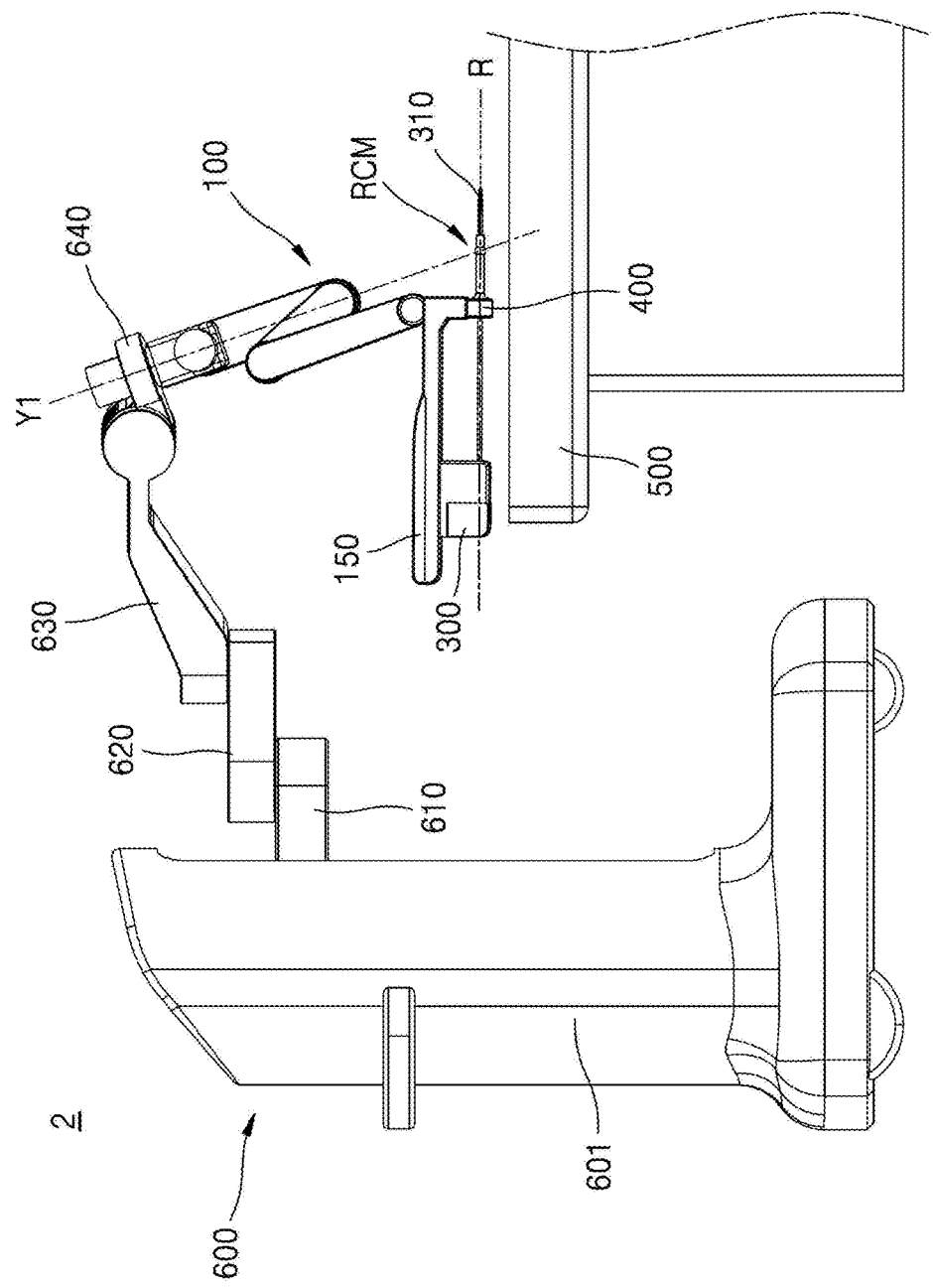
Figure 72:
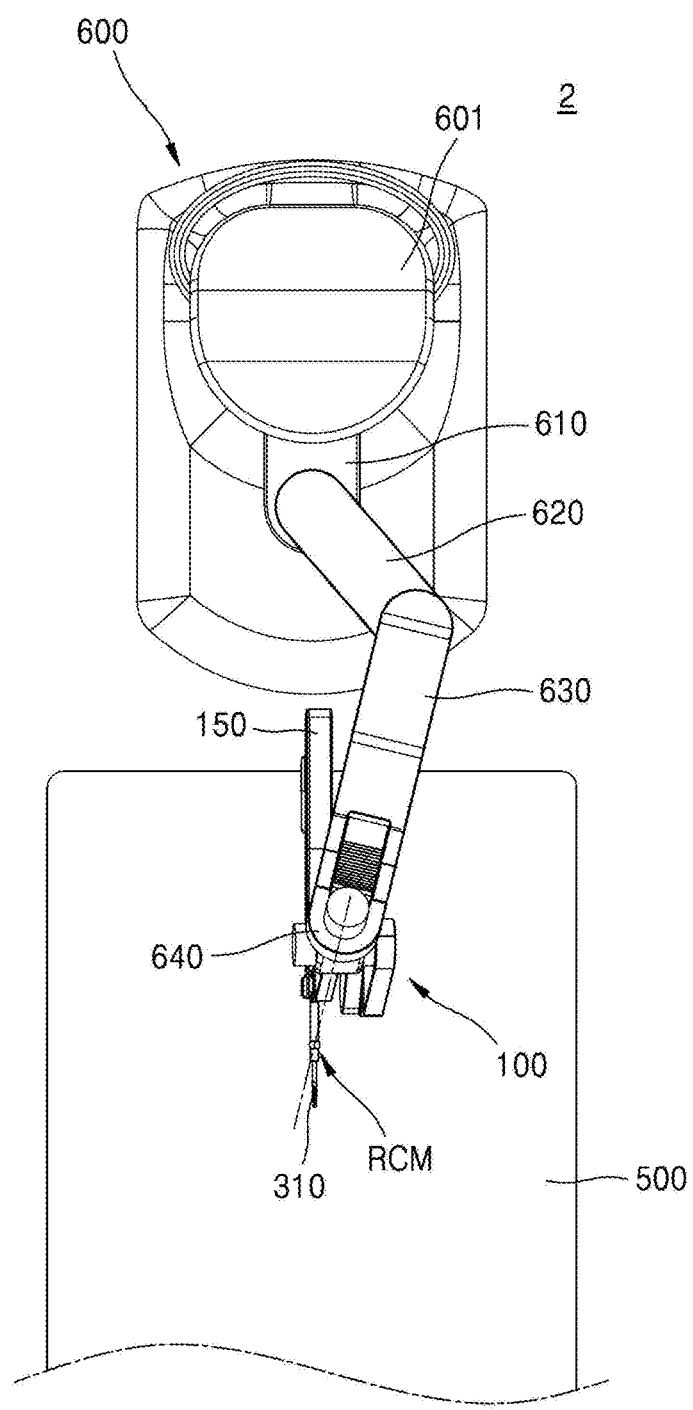
Figure 73:
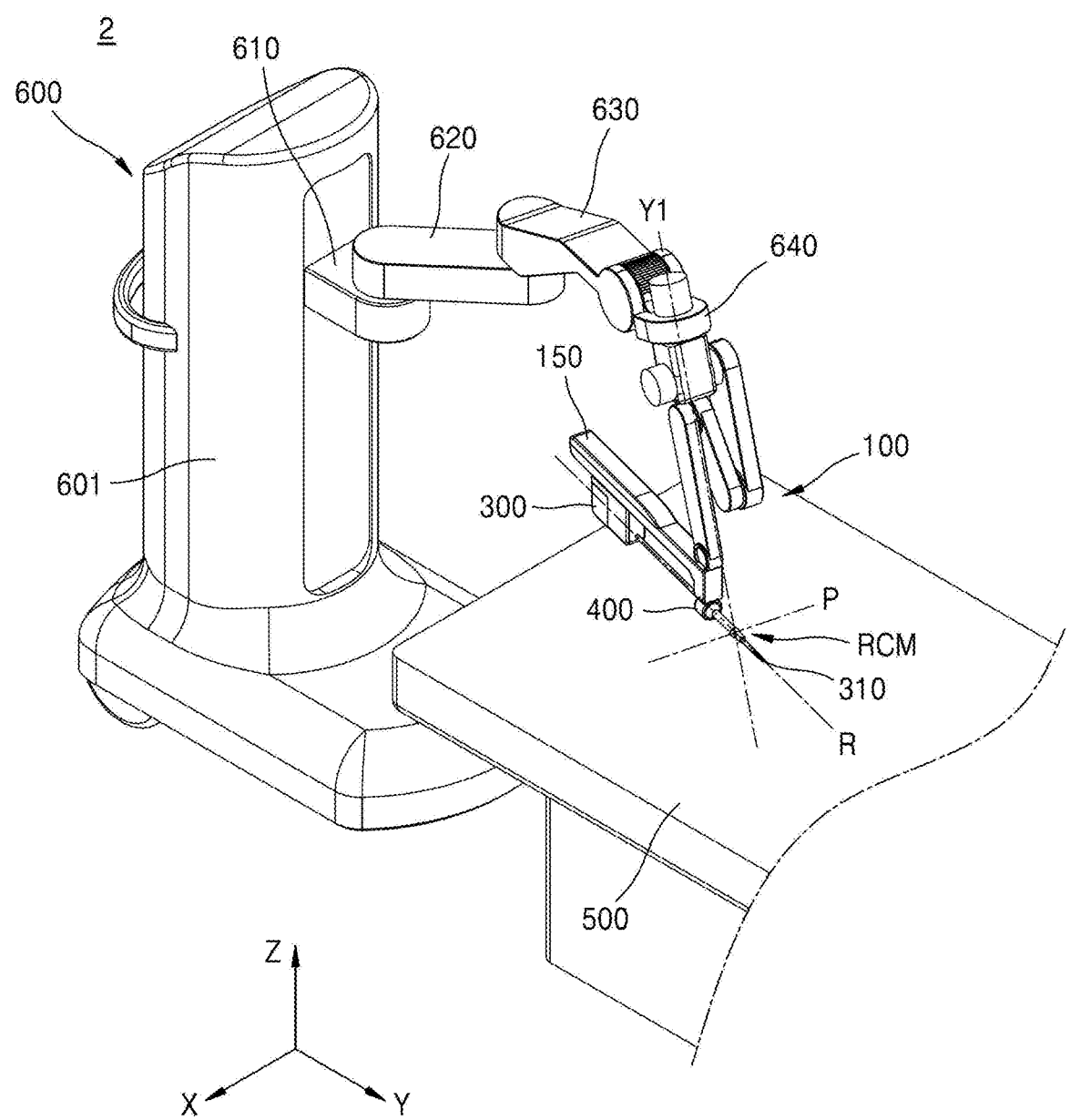
FIGS. 73 to 75 are views illustrating a fourth arrangement state of the surgical robot arm according to the second embodiment of the present disclosure.
Figure 74:
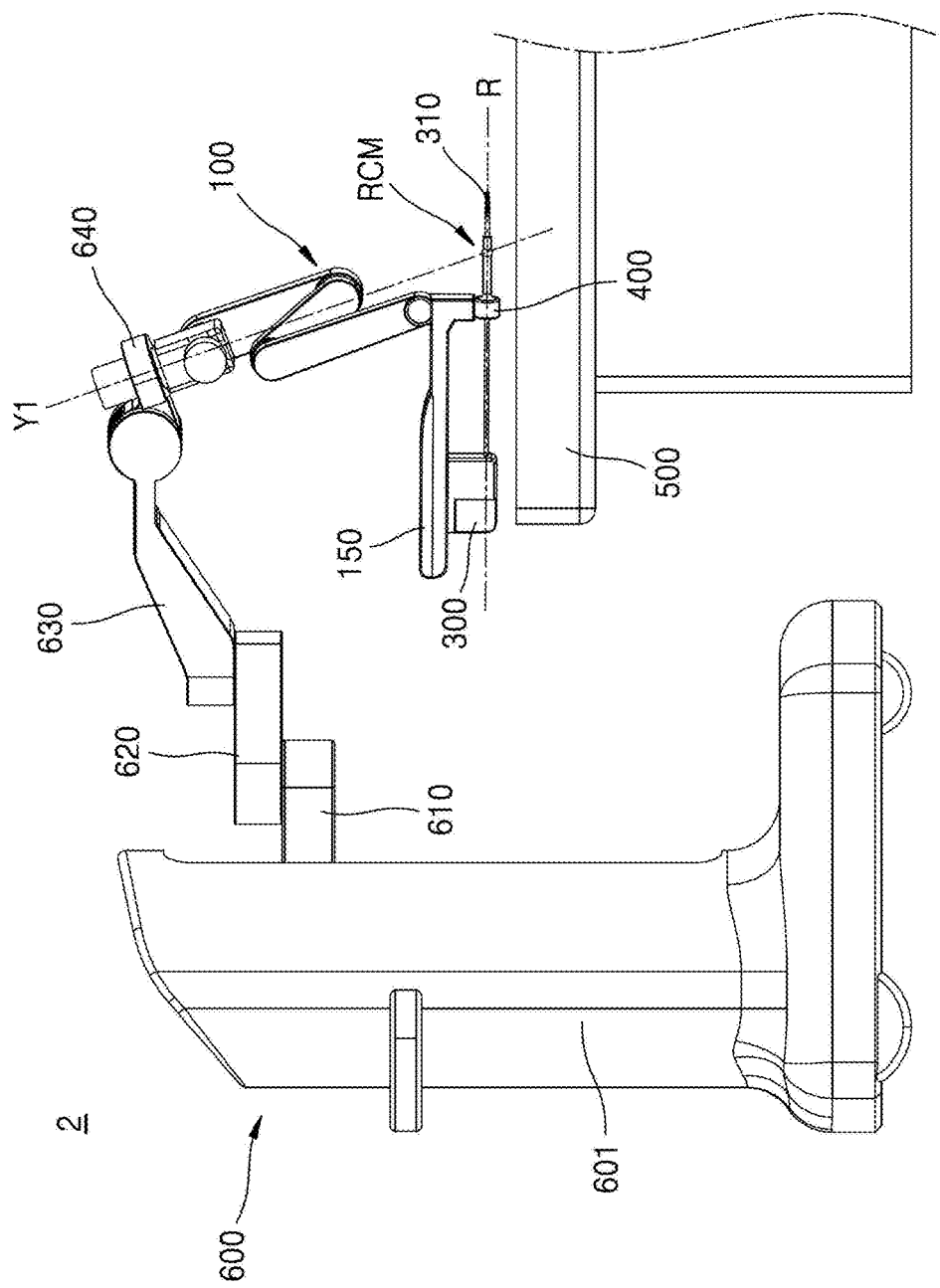
Figure 75:
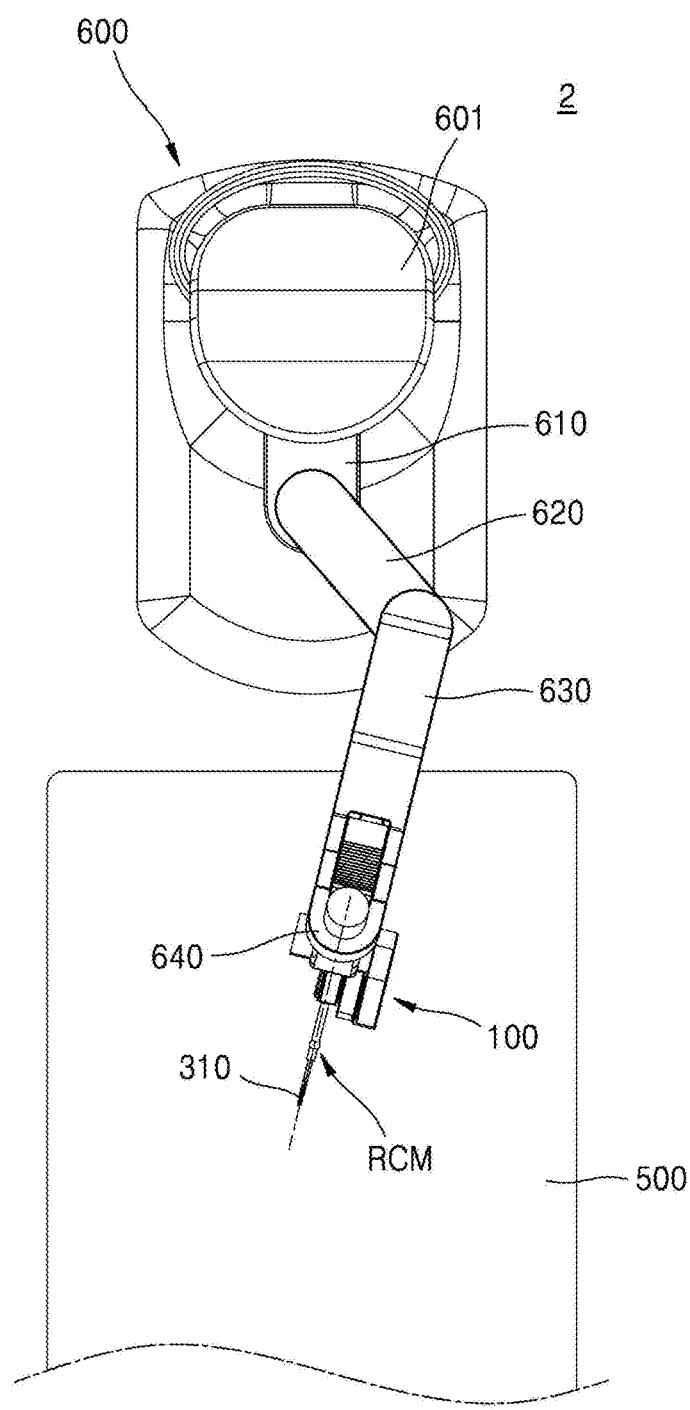
Figure 76:
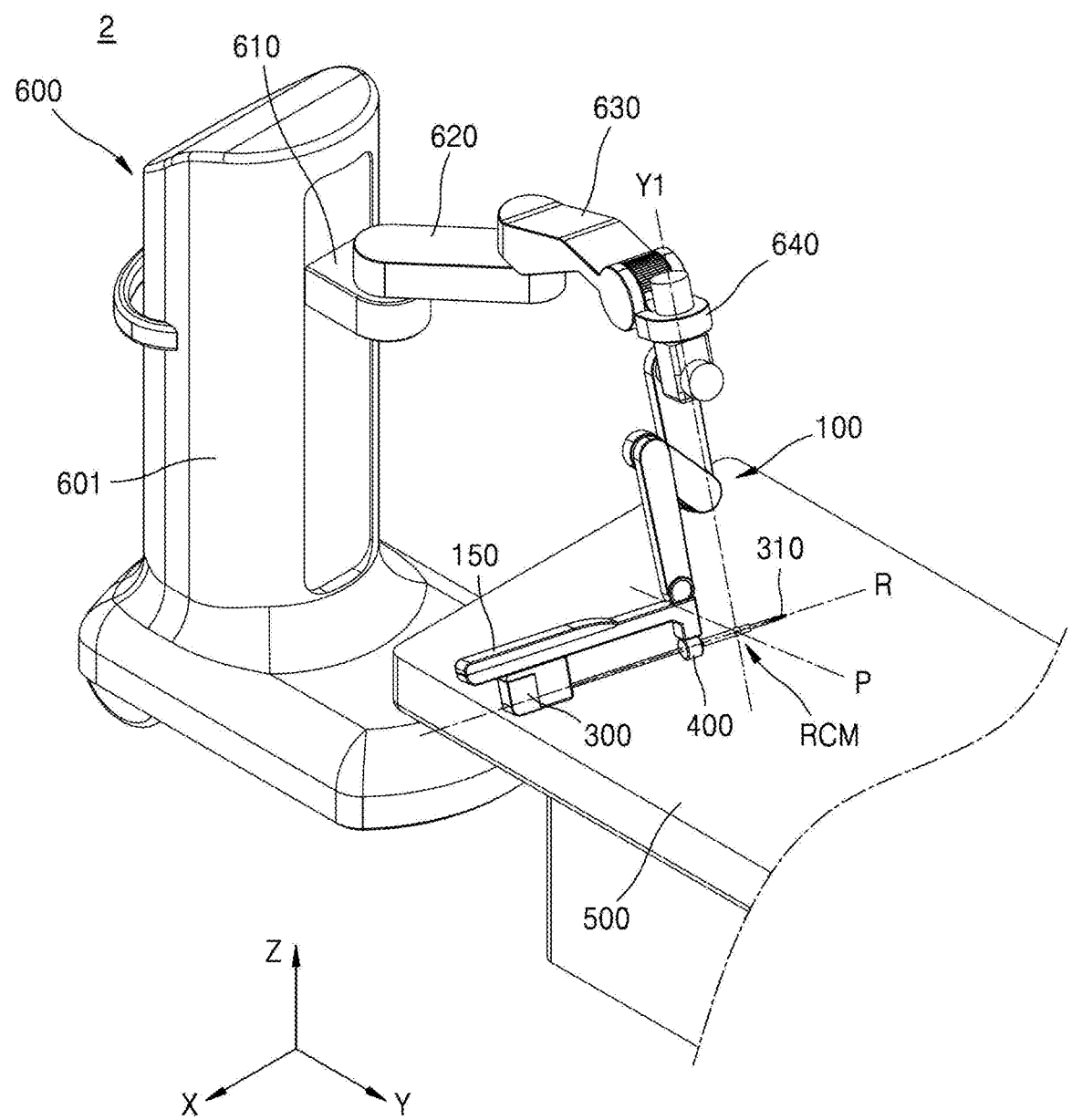
FIGS. 76 to 78 are views illustrating a fifth arrangement state of the surgical robot arm according to the second embodiment of the present disclosure.
Figure 77:
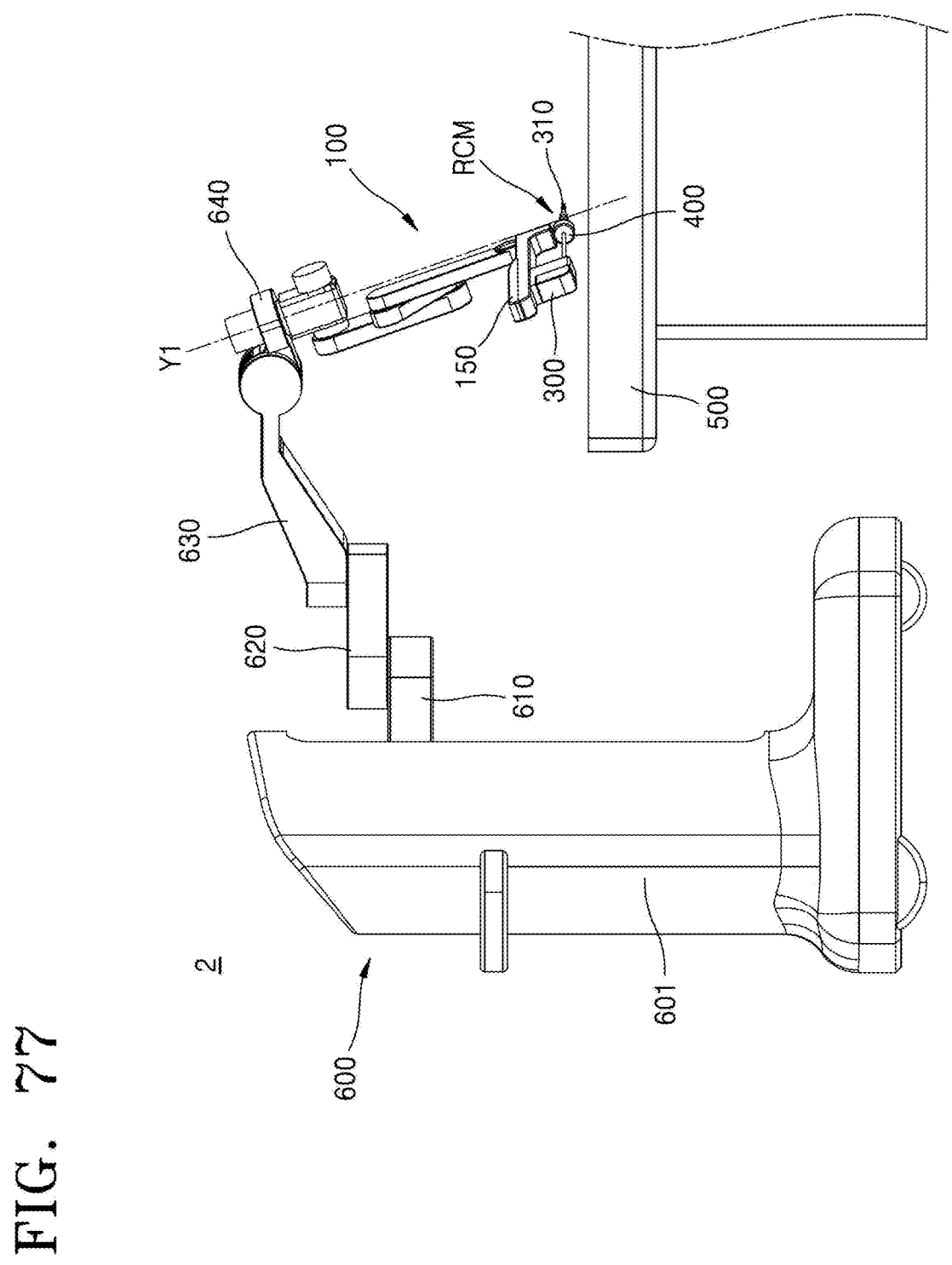
Figure 78:
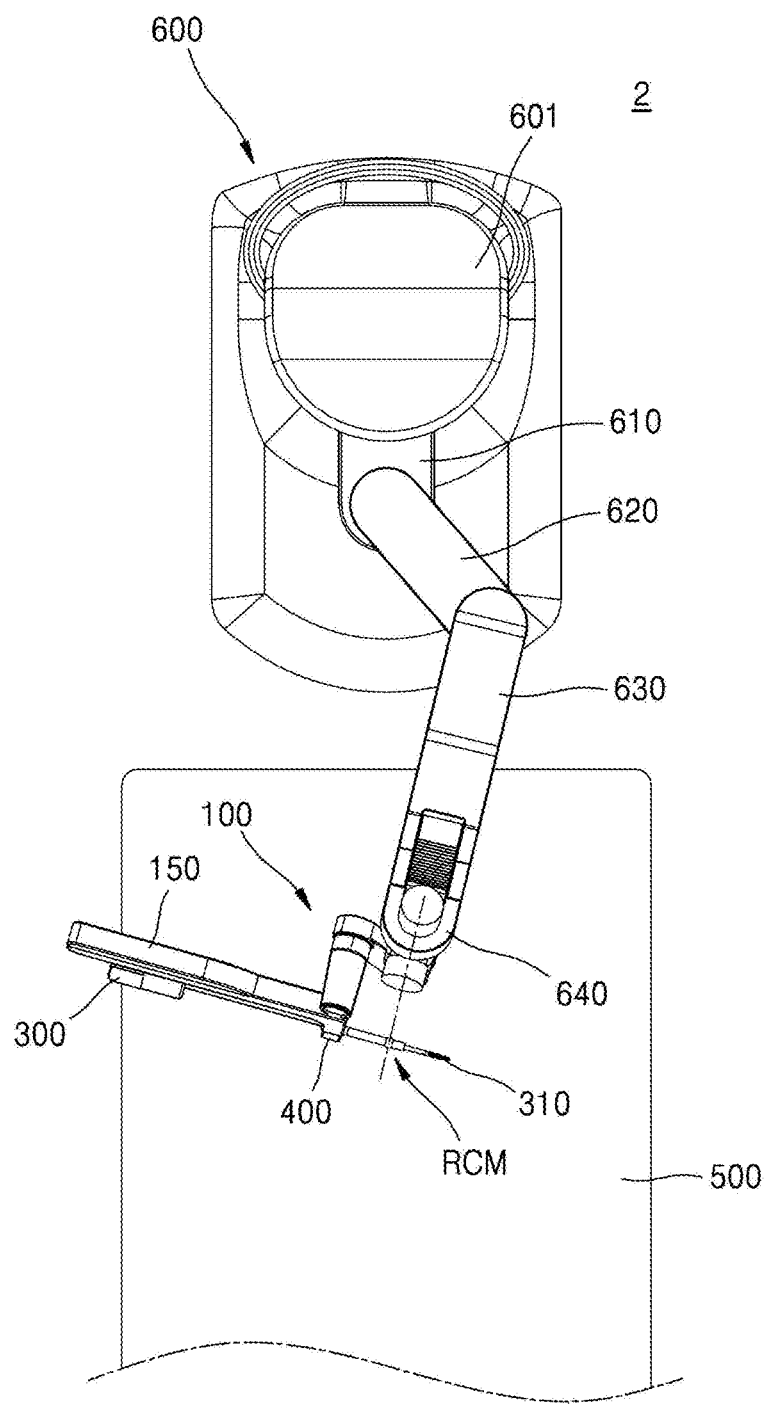

FIGS. 70 to 72 are views illustrating a third arrangement state of the surgical robot arm according to the second embodiment of the present disclosure.

Referring to FIG. 70, compared to the first arrangement state of the surgical robot arm 2 according to the second embodiment of the present disclosure illustrated in FIG. 64, the second setup link 620 and the third setup link 630 may be rotated, and the active arm 100, specifically the first link 110, may be rotated around the yaw axis Y1 with respect to the fourth setup link 640.

Referring to FIG. 72, as the second setup link 620 and the third setup link 630 rotate, the RCM may move in a direction parallel to the Y-axis. At this time, by rotating the active arm 100, specifically the first link 110, around the yaw axis Y1 with respect to the fourth setup link 640, only the RCM can be moved in a direction parallel to the Y-axis while maintaining the same entry angle into the RCM as in the state before rotating the second setup link 620 and the third setup link 630.

Referring to FIGS. 73 to 78, fourth and fifth arrangement states of the surgical robot arm 2 according to the second embodiment of the present disclosure are illustrated, the position of the RCM can be changed by rotating each of the second setup link 620 and the third setup link 630 while maintaining an angle formed between the third setup link 630 and the fourth setup link 640 unchanged.

That is, by maintaining the angle formed between the third setup link 630 and the fourth setup link 640 unchanged, the position of the RCM can be changed in various ways while maintaining the angle between the active arm 100, specifically the yaw axis Y1, which is a central axis of rotation of the first link 110, and the horizontal plane unchanged, and once the position of the RCM is determined, the entry angle of the surgical instrument 300 into the RCM can be changed in various ways by rotating the first link 110, which is rotatably coupled to the fourth setup link 640, around the yaw axis Y1, and by varying the active arm 100, specifically, the roll axis R of the surgical instrument 300 coupled to the fifth link 150.

The surgical robot arm 2 according to the second embodiment of the present disclosure is the same as the surgical robot arm 1 according to the first embodiment in terms of the configuration, operating principle, and effect of the body 601 and the active arm 100, except that one setup link is reduced, and thus a detailed description thereof will be omitted in the overlapping range.

Third Embodiment of Surgical Robot Arm

Hereinafter, a surgical robot arm according to a third embodiment of the present disclosure will be described.

Here, the surgical robot arm according to the third embodiment of the present disclosure is different from the surgical robot arm 1 according to the embodiment of the present disclosure described above in that the configuration of the setup links is changed. The configuration changed from the first embodiment as described above will be described in detail later.

Figure 79:
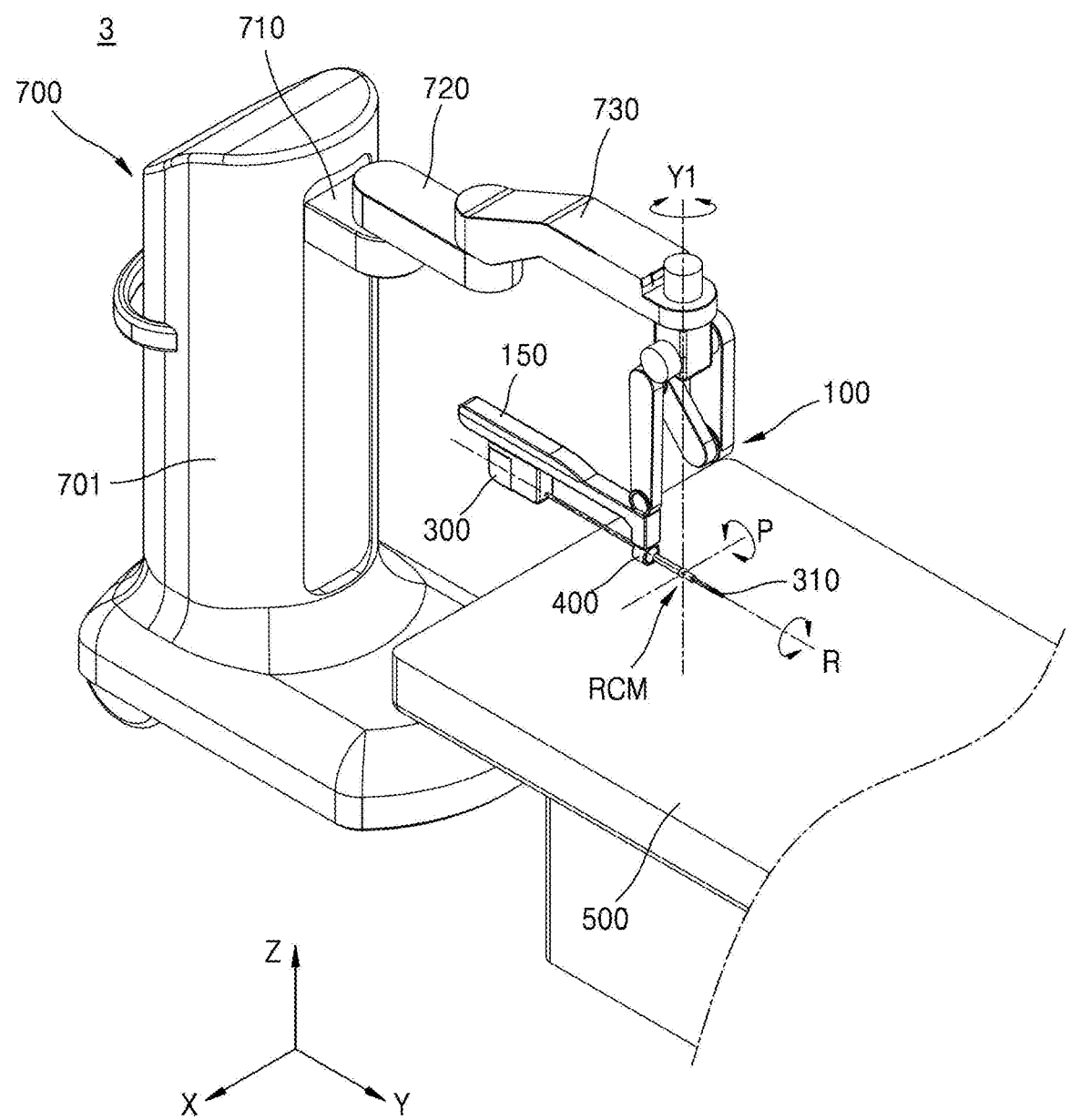
FIGS. 79 to 81 are views illustrating a first arrangement state of a surgical robot arm according to a third embodiment of the present disclosure.
Figure 80:
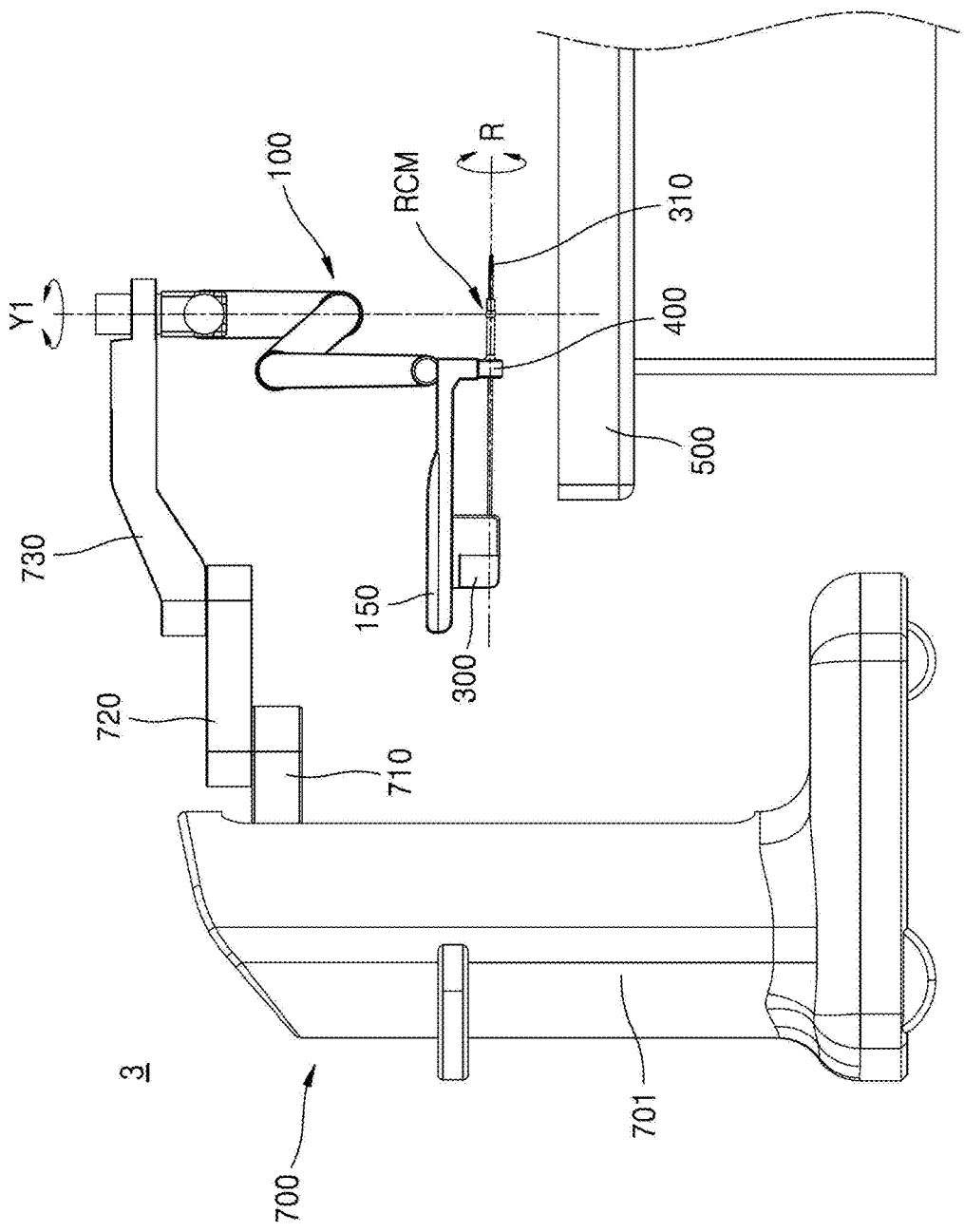
Figure 81:
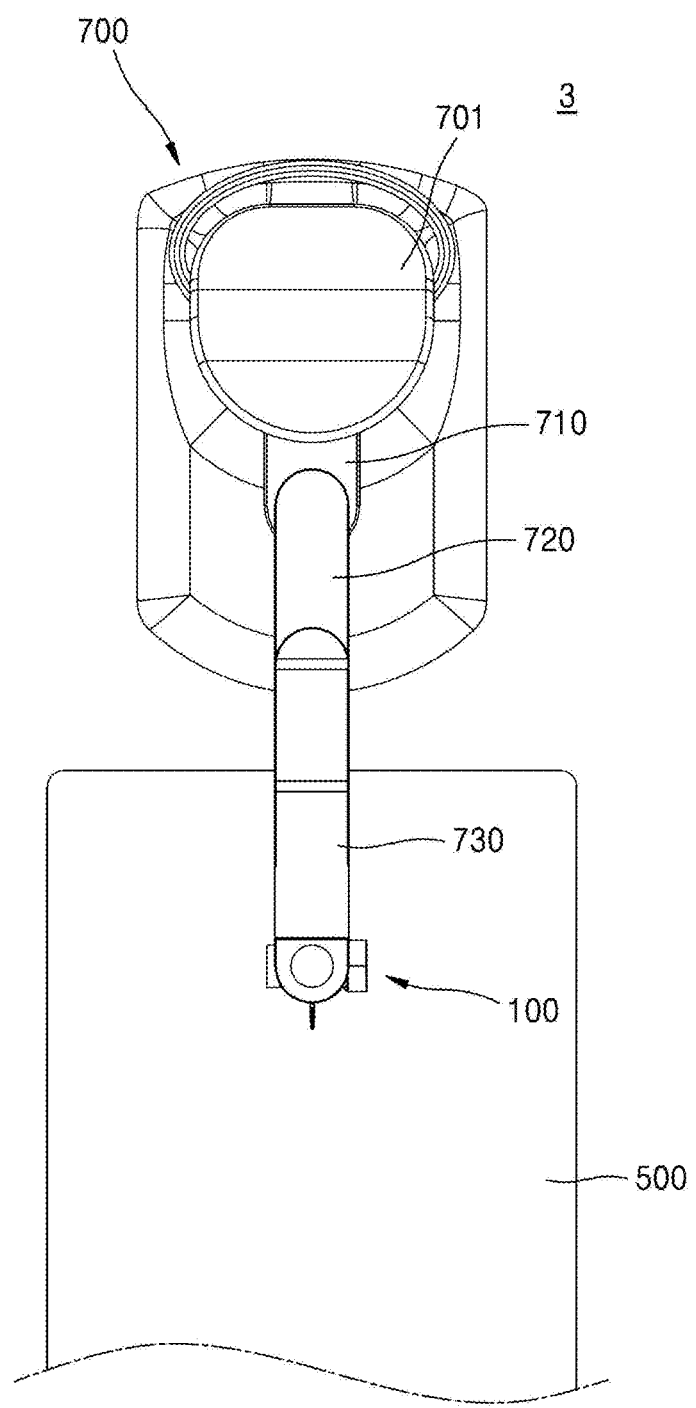

FIGS. 79 to 81 are views illustrating a first arrangement state of the surgical robot arm according to the third embodiment of the present disclosure.

A surgical robot arm 3 according to the third embodiment of the present disclosure may include a setup arm 700 and the active arm 100. The setup arm 700 is rotatably coupled to the active arm 100 and may include a body 701, a first setup link 710, a second setup link 720, and a third setup link 730.

A central axis of rotation of the second setup link 720 with respect to the first setup link 710 and a central axis of rotation of the third setup link 730 with respect to the second setup link 720 may be configured parallel to each other. Specifically, the central axis of rotation may be configured parallel to the Z-axis.

The third setup link 730 is rotatably coupled to the active arm 100, specifically, the first link 110. At this time, the yaw axis Y1, which is the central axis of rotation of the first link 110 that is rotatably coupled to the third setup link 730, may be positioned at a fixed angle relative to the third setup link 730.

Referring to FIG. 79, the first link 110 is coupled to the third setup link 730 such that the yaw axis Y1, which is the central axis of rotation of the first link 110, forms a predetermined angle, for example, 90°, with the horizontal plane. That is, the surgical robot arm 3 according to the third embodiment is formed such that the yaw axis Y1 of the active arm 100 forms a constant angle with the horizontal plane.

The surgical robot arm 3 according to the third embodiment of the present disclosure is the same as the surgical robot arm 1 according to the first embodiment in terms of the configuration, operating principle, and effect of the body 701, the plurality of setup links, and the active arm 100, except that, in relation to the configuration of the setup arm 700, the third setup link 730 is included as a single configuration that integrates the third setup link 230, the fourth setup link 240, and the fifth setup link 250 of the surgical robot arm 1 according to the first embodiment of the present disclosure, resulting in a reduction of two degrees of freedom and maintaining a constant angle between the yaw axis Y1 of the active arm 100 and the horizontal plane, and thus a detailed description thereof will be omitted in the overlapping range.

Figure 82:
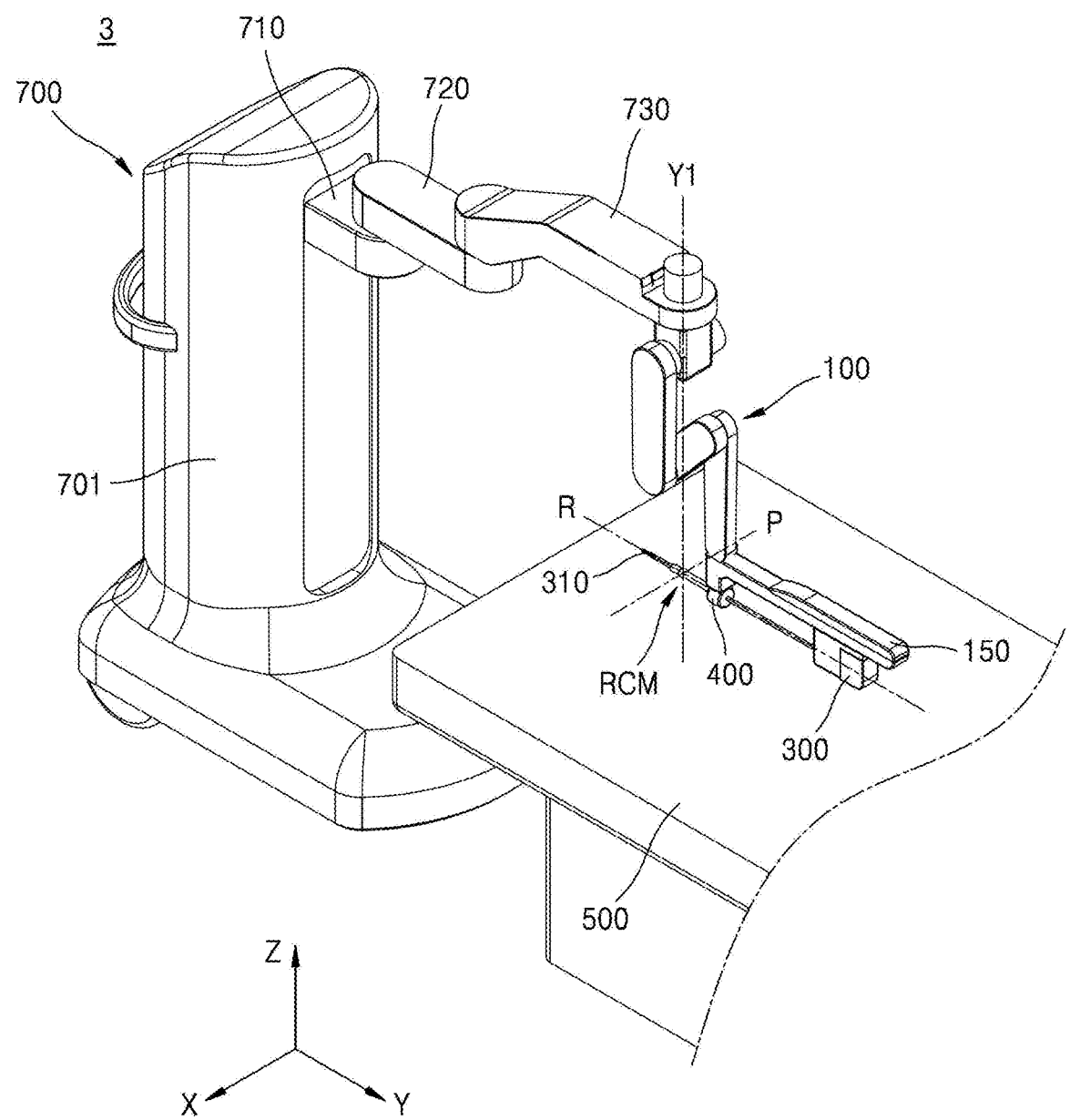
FIGS. 82 to 84 are views illustrating a second arrangement state of a surgical robot arm according to the third embodiment of the present disclosure.
Figure 83:
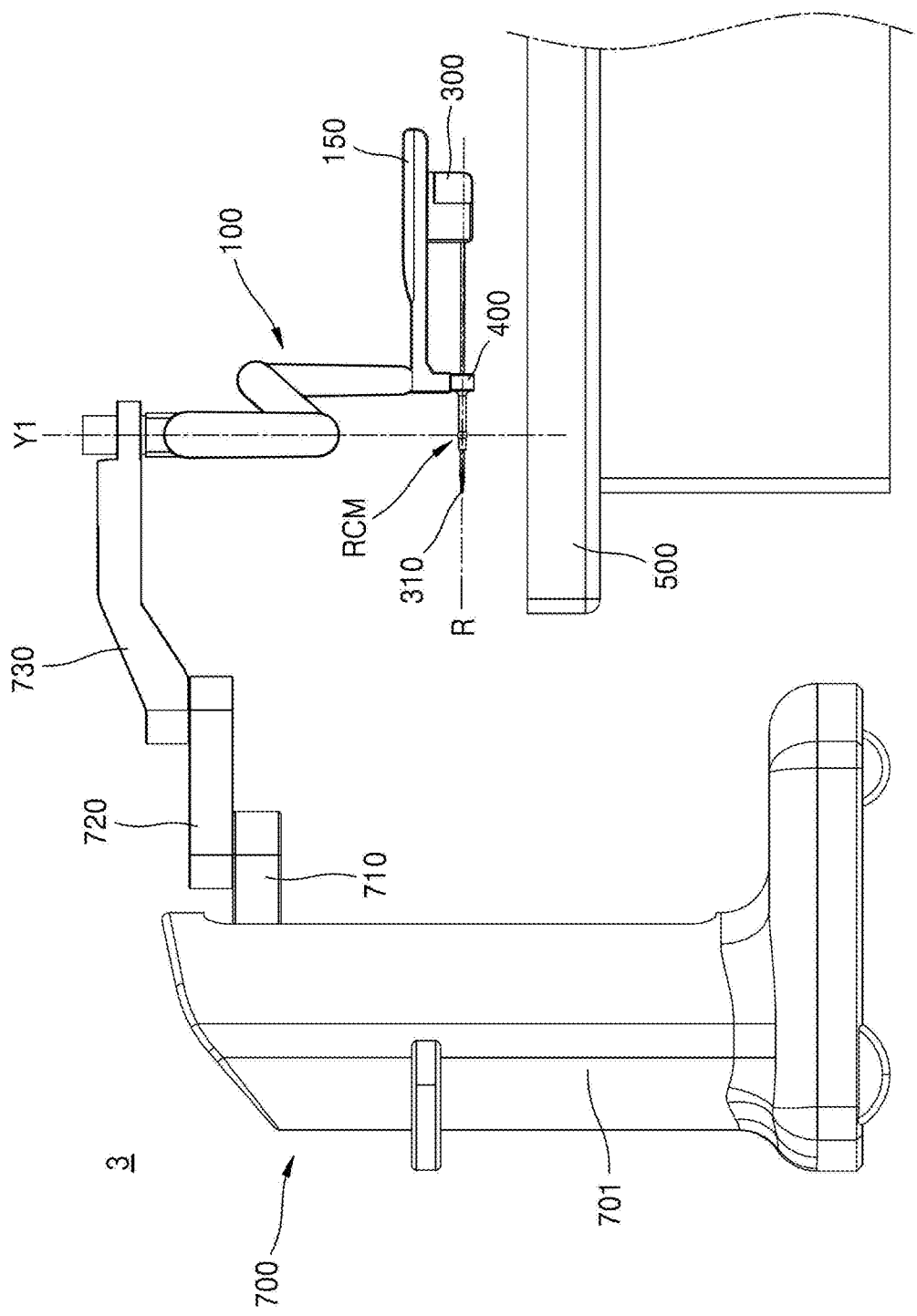
Figure 84:
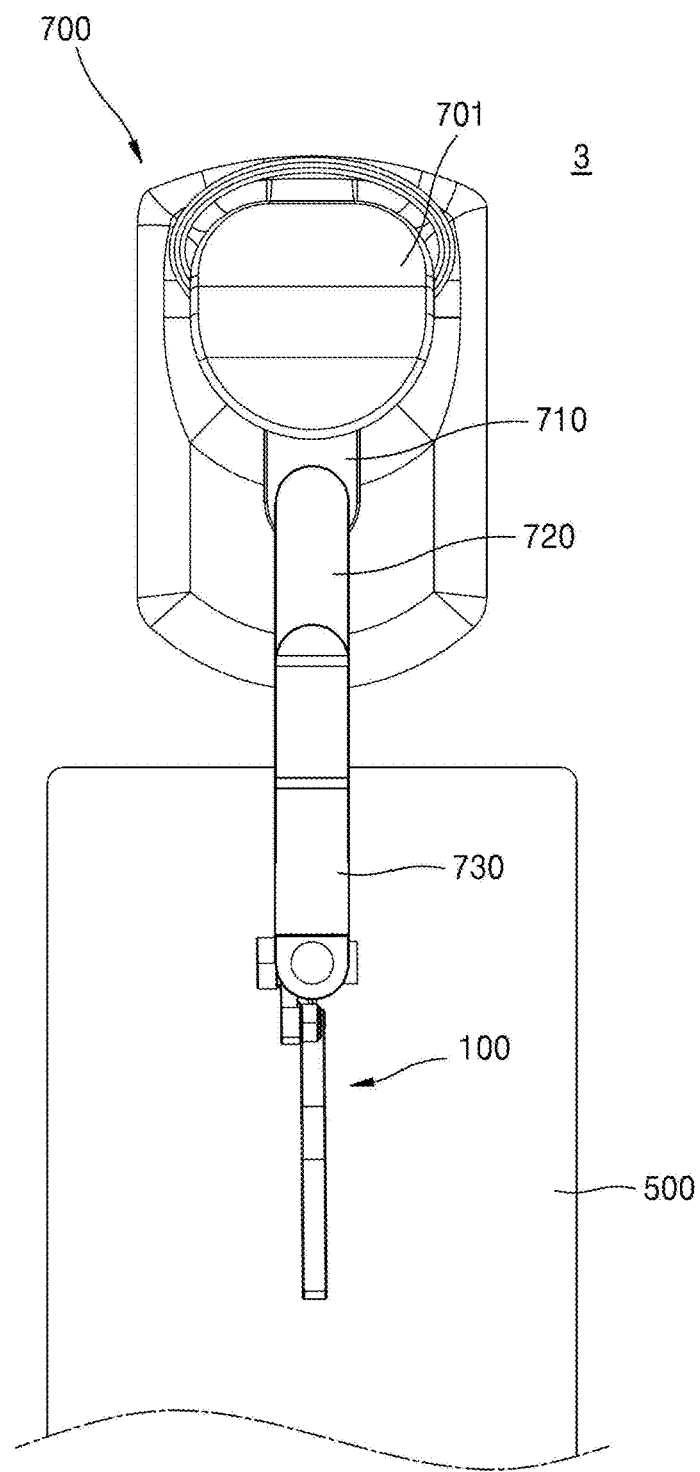

FIGS. 82 to 84 illustrate a second arrangement state of the surgical robot arm 3 according to the third embodiment of the present disclosure, in which, compared to the first arrangement state described above, the active arm 100, specifically the first link 110, is rotated relative to the third setup link 730 around the yaw axis Y1 (i.e., yaw-rotated).

Since the positions of the second setup link 720 and the third setup link 730 are the same, the RCM remains constant. At this time, by rotating the third link 130, the fourth link 140, and the fifth link 150 of the active arm 100, the entry angle of the surgical instrument 300 can be adjusted so that the end tool 310 of the surgical instrument 300 faces the body 701 to position the surgical instrument 300 in a direction opposite to that of the first arrangement state shown in FIG. 79.

Figure 85:
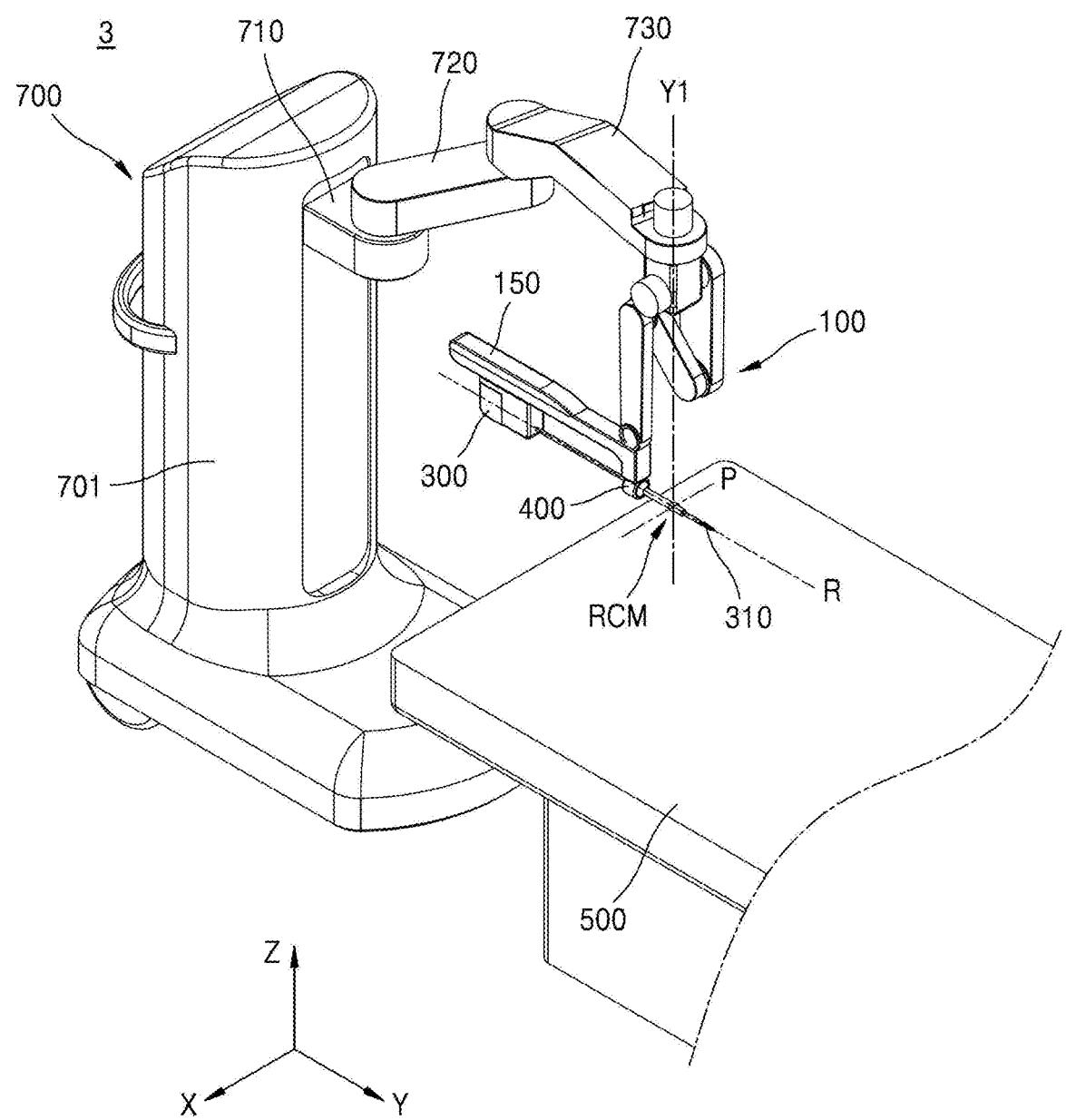
FIGS. 85 to 87 are views illustrating a third arrangement state of the surgical robot arm according to the third embodiment of the present disclosure.
Figure 86:
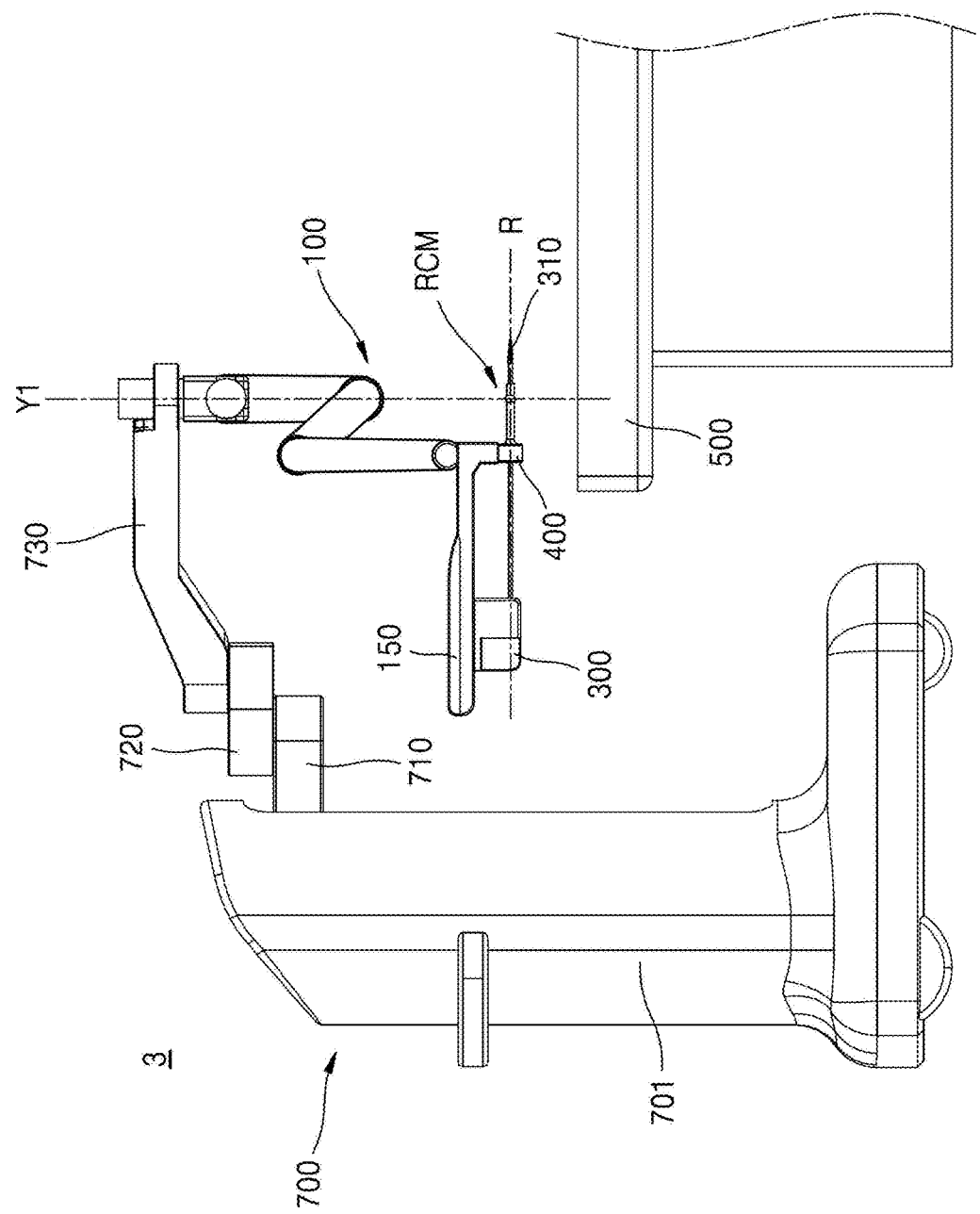
Figure 87:
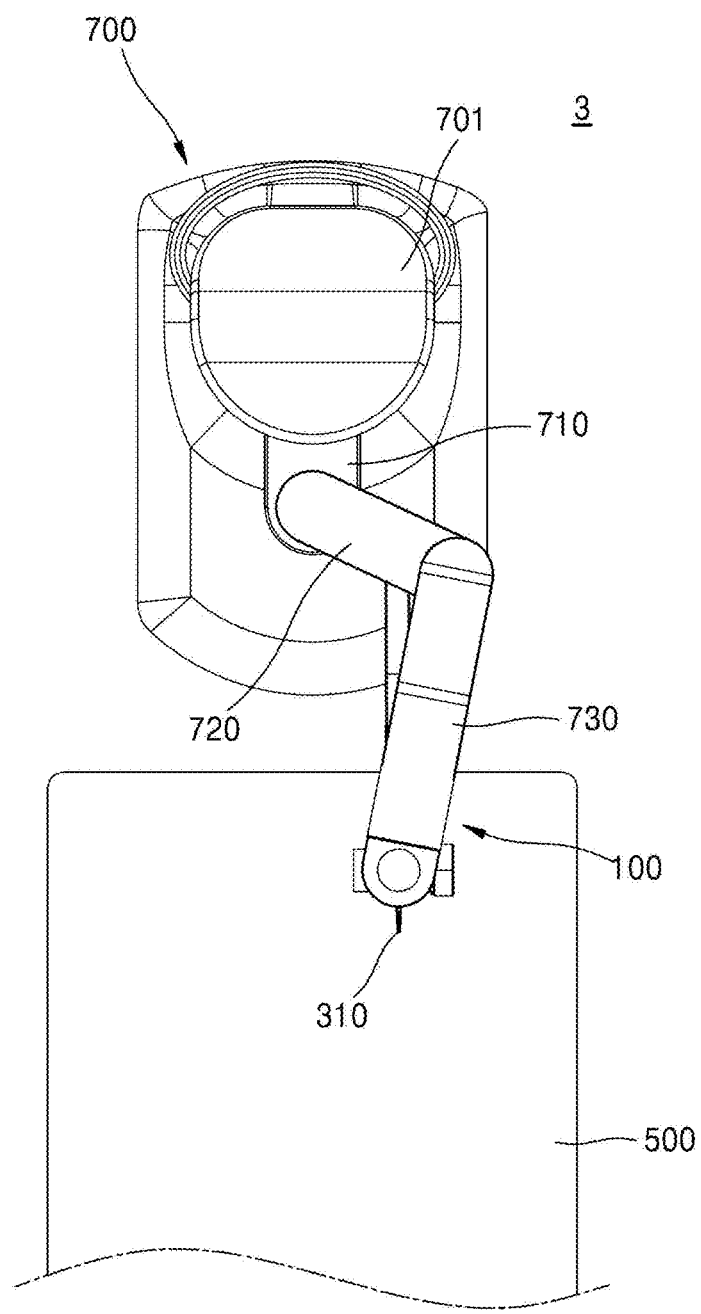
Figure 88:
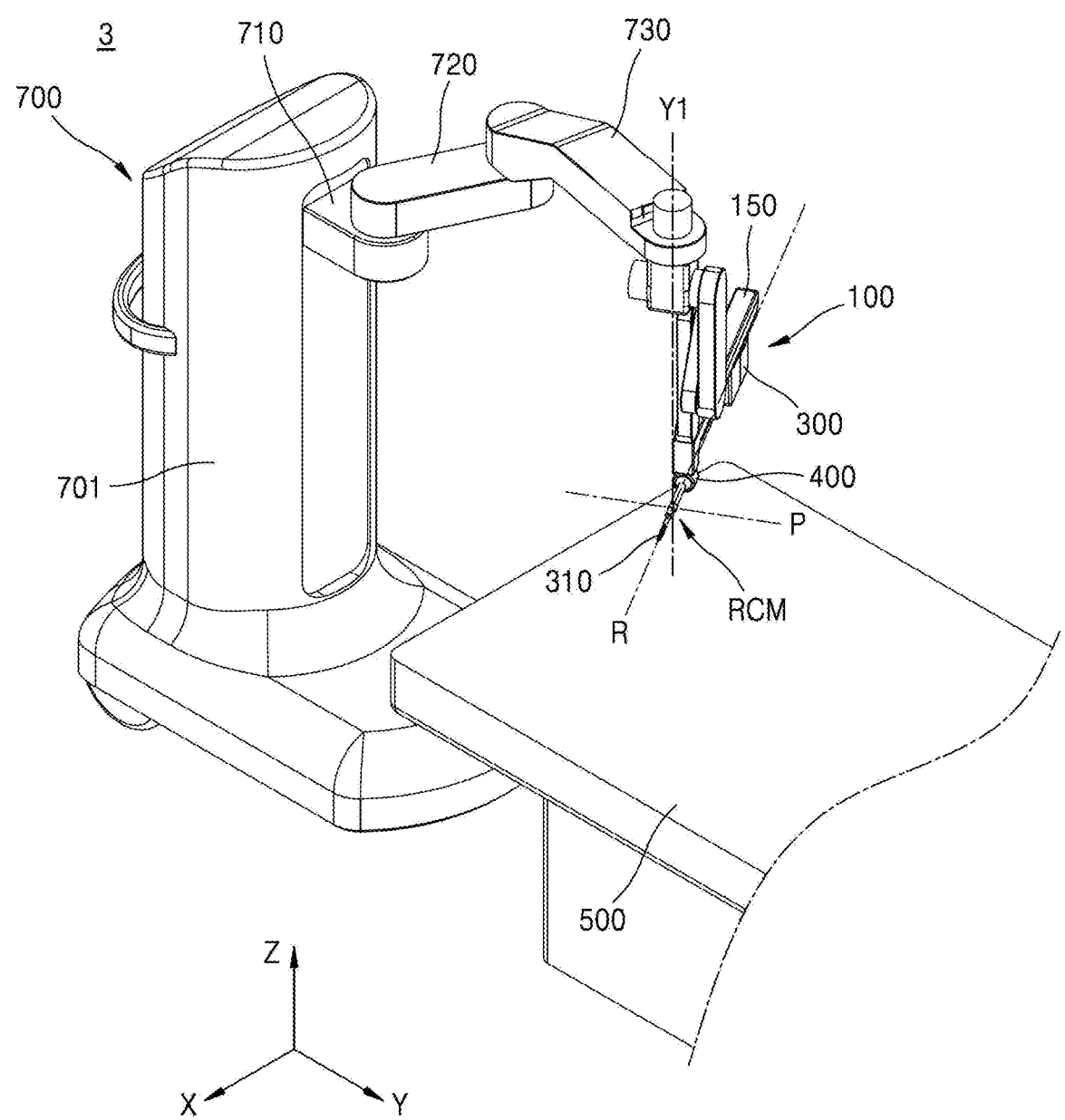
FIGS. 88 to 90 are views illustrating a fourth arrangement state of the surgical robot arm according to the third embodiment of the present disclosure.
Figure 89:
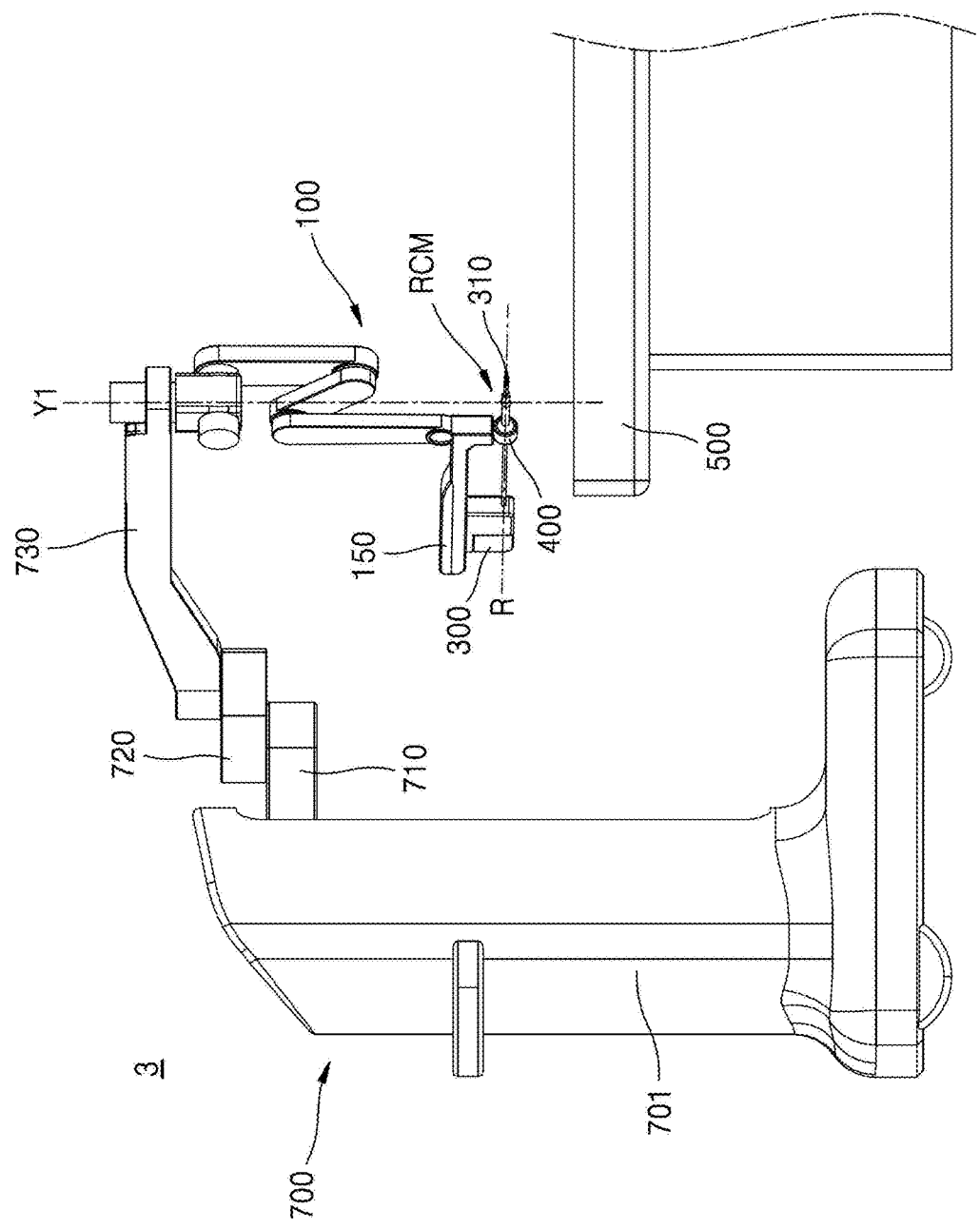
Figure 90:
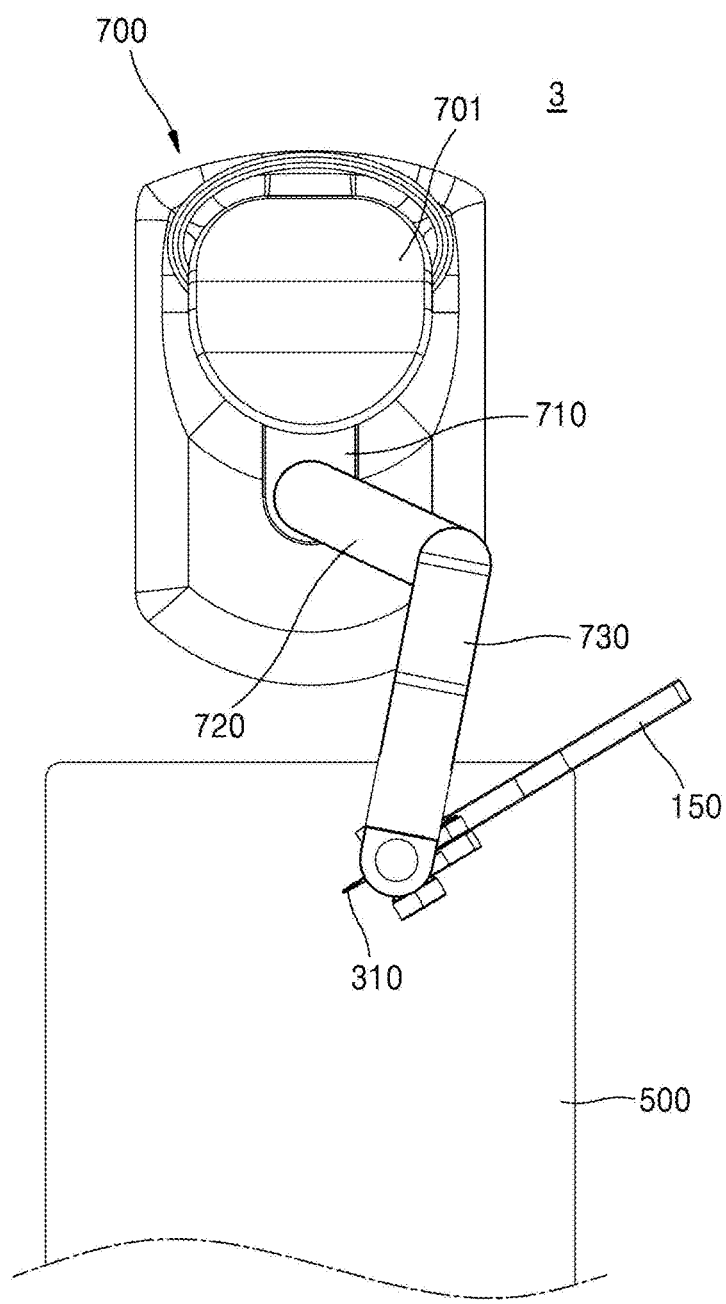

FIGS. 85 to 87 are views illustrating a third arrangement state of the surgical robot arm according to the third embodiment of the present disclosure.

Referring to FIG. 85, compared to the first arrangement state of the surgical robot arm 3 according to the third embodiment of the present disclosure illustrated in FIG. 79, the second setup link 720 and the third setup link 730 may be rotated, and the active arm 100, specifically the first link 110, may be rotated around the yaw axis Y1 with respect to the third setup link 730.

As the second setup link 720 and the third setup link 730 rotate, the RCM moves in a direction parallel to the Y-axis by a certain degree. When the first link 110, which is rotatably coupled to the third setup link 730, does not rotate around the yaw axis Y1, as the third setup link 730 rotates, the position of the surgical instrument 300 may change, that is, the roll axis R and the entry angle of the surgical instrument 300 may be changed.

At this time, by rotating the active arm 100, specifically the first link 110, around the yaw axis Y1, only the RCM can be moved in a direction parallel to the Y-axis while maintaining the same entry angle of the surgical instrument 300 into the RCM even when the second setup link 720 and third setup link 730 are rotated.

The surgical robot arm 3 according to the third embodiment of the present disclosure is the same as the surgical robot arm 1 according to the first embodiment in terms of the configuration, operating principle, and effect of the body 701 and the active arm 100, except that two setup links are reduced, and thus a detailed description thereof will be omitted in the overlapping range.

As such, the present disclosure has been described with reference to one embodiment shown in the views, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present disclosure relates to a surgical robot arm, and may be used in a surgical robot arm for minimally invasive surgery, which is formed in a modular manner for use in a laparoscopic surgery or other various surgeries.

The invention claimed is:

1. A surgical robot arm to which a surgical instrument is mounted, the surgical robot arm comprising:
   a setup arm including a body and a setup link assembly movably disposed on the body; and
   an active arm rotatably coupled to one end portion of the setup arm,
   wherein the setup link assembly includes:
      a first setup link linearly movable in a height direction on the body;
      a second setup link rotatably and axially coupled to the first setup link around a first shaft configured to serve as a central axis of rotation; and
      a third setup link rotatably and axially coupled to the second setup link around a second shaft, the second shaft being different from the first shaft and configured to serve as a central axis of rotation,
   wherein the active arm includes:
      a first link coupled to the setup arm by a first joint, the first link being yaw-rotatable around a yaw axis with respect to the setup arm;
      a second link coupled to the first link by a second joint;
      a third link axially coupled to the second link to be rotatable around a third joint with respect to the second link;
      a fourth link axially coupled to the third link to be rotatable around a fourth joint with respect to the third link; and
      a fifth link that is axially coupled to the fourth link to be rotatable around a fifth joint with respect to the fourth link, the fifth link being configured to allow the surgical instrument to be mounted thereto,
   wherein a remote center of motion (RCM) is defined at a remaining vertex of a parallelogram with the third joint, the fourth joint, and the fifth joint constituting other vertices of the parallelogram, and
   wherein the first joint is disposed relatively above the RCM.

2. The surgical robot arm of claim 1, wherein the yaw axis and a roll axis of the surgical instrument are different from each other.

3. The surgical robot arm of claim 2, wherein in a state in which the roll axis of the surgical instrument is positioned parallel to a horizontal plane, the yaw axis and the roll axis are configured to form a predetermined angle rather than being parallel to each other.

4. The surgical robot arm of claim 1, wherein the setup link assembly includes one or more setup links connecting the active arm to the body, the one or more setup links being rotatable around a Z-axis with respect to the body.

5. The surgical robot arm of claim 1, wherein
   the yaw axis is perpendicular to one surface of the third setup link, and
   the first link is coupled to the third setup link and is rotatable around the yaw axis with respect to the third setup link.

6. The surgical robot arm of claim 1, wherein the second shaft is disposed perpendicular to the first shaft.

7. The surgical robot arm of claim 1, wherein the setup link assembly further includes one or more setup links disposed between the second setup link and the third setup link, the one or more setup links being rotatable around respective one or more shafts that are substantially parallel to the first shaft.

8. The surgical robot arm of claim 1, wherein a height, in a Z-axis direction, of a point at which the yaw axis passes through the setup arm is higher than a height of the RCM in the Z-axis direction.

9. The surgical robot arm of claim 1, wherein a height, in a Z-axis direction, of a proximal end of the yaw axis relative to the first joint is higher than a height, in the Z-axis direction, of a distal end of the yaw axis relative to the first joint.

10. The surgical robot arm of claim 1, wherein the setup arm is operable only during a setup period in which the surgical robot arm is disposed on one side of a patient.

11. The surgical robot arm of claim 1, wherein the RCM is positioned on an extension line of the yaw axis.

12. The surgical robot arm of claim 1, wherein,
   when the third link rotates around the third joint,
   the fourth link and a line segment connecting the third joint to the RCM are configured to rotate while maintaining a parallel state, and
   the third link and a line segment connecting the fifth joint to the RCM are configured to rotate while maintaining a parallel state.

13. The surgical robot arm of claim 1, wherein the RCM remains constant in position regardless of the rotation of the third link.

14. The surgical robot arm of claim 1, wherein
the third link and a line segment connecting the fifth joint to the RCM maintain a parallel state in any state of motion of the surgical robot arm, and
the fourth link and a line segment connecting the third joint to the RCM maintain a parallel state in any state of motion of the surgical robot arm.

15. The surgical robot arm of claim 1, wherein each of the third link, the fourth link, and the fifth link is offset by a certain degree in a direction of a rotational axis thereof.

16. The surgical robot arm of claim 1, wherein, the fourth link is disposed on one side of the third link in a direction of a rotational axis of the third link.

17. The surgical robot arm of claim 1, wherein the third link and the fourth link are configured to allow at least partial overlap with each other in a direction of the yaw axis.

18. The surgical robot arm of claim 1, wherein the fourth link and the fifth link are configured to allow at least partial overlap with each other in a direction of the yaw axis.

19. The surgical robot arm of claim 1, wherein, in a state in which the surgical instrument coupled to the fifth link is horizontal and an end tool of the surgical instrument is disposed in a direction away from the body, a first surface of the fifth link, to which the surgical instrument is coupled, is disposed to face downward in a Z-axis direction.

20. The surgical robot arm of claim 19, wherein, in the state, the surgical instrument is configured to be disposed below the fifth link.

21. The surgical robot arm of claim 19, wherein, in the state, the first, second, third, fourth, and fifth links are configured to be not disposed between the surgical instrument and a bed.

22. The surgical robot arm of claim 1, wherein a longitudinal central axis of the yaw axis and a longitudinal central axis of the fifth link form a predetermined angle.

* * * * *